(12) United States Patent
Huster et al.

(10) Patent No.: US 8,460,223 B2
(45) Date of Patent: Jun. 11, 2013

(54) HIGH FREQUENCY CHEST WALL OSCILLATION SYSTEM

(75) Inventors: Keith A. Huster, Sunman, IN (US); Gregory W. Branson, Batesville, IN (US); Todd P. O'Neal, Fairfield, OH (US); Mayur Yermaneni, Cincinnati, OH (US); Daniel G. Chase, Menomonie, WI (US); Karen M. Gove, Maple Grove, MN (US); Timothy J. Ikeler, Mount Pleasant, SC (US); Stephen R. Schulte, Harrison, OH (US); Rachel Hopkins King, Lawrenceburg, IN (US); Teresa Maria Mirabella, Daniel Island, SC (US)

(73) Assignee: Hill-Rom Services Pte. Ltd., Singapore (SG)

( * ) Notice: Subject to any disclaimer, the term of this patent is extended or adjusted under 35 U.S.C. 154(b) by 720 days.

(21) Appl. No.: 11/685,285

(22) Filed: Mar. 13, 2007

(65) Prior Publication Data
US 2008/0000477 A1    Jan. 3, 2008

Related U.S. Application Data

(60) Provisional application No. 60/782,383, filed on Mar. 15, 2006.

(51) Int. Cl.
*A61H 31/00*    (2006.01)
(52) U.S. Cl.
USPC ............. 601/44; 601/41; 601/43; 601/149; 601/151; 601/152

(58) Field of Classification Search
USPC ............. 128/200.24, 202.19, 202.16; 601/41, 601/43, 48, 11, 14, 44, 46, 78, 79, 81, 84, 601/107, 108, 148, 149, 150, 151, 152
See application file for complete search history.

(56) References Cited

U.S. PATENT DOCUMENTS

| | | | |
|---|---|---|---|
| 402,779 | A | 5/1889 | Steinhoff |
| 481,527 | A | 8/1892 | Fasoldt |

(Continued)

FOREIGN PATENT DOCUMENTS

| | | |
|---|---|---|
| CA | 1225889 | 8/1987 |
| EP | 0026799 A1 | 4/1981 |

(Continued)

OTHER PUBLICATIONS

The International Search Report and The Written Opinion of the International Searching authority from PCT/US07/63864, dated Feb. 22, 2008 (13 pages).

(Continued)

*Primary Examiner* — Justine Yu
*Assistant Examiner* — LaToya M Louis
(74) *Attorney, Agent, or Firm* — Barnes & Thornburg LLP

(57) ABSTRACT

An therapy system is operable to deliver a plurality of respiratory therapies to the patient and has an assessment system operable to assess the efficacy of at least one of the respiratory therapies. The therapy system may be operable to deliver any one or more of the following therapies: a positive expiratory pressure (PEP) therapy, a nebulizer therapy, an intermittent positive pressure breathing (IPPB) therapy, a cough assist therapy, a suction therapy, a bronchial dilator therapy, and the like. The assessment system may comprise any one or more of the following devices: a flow meter, a spirometer, an electronic stethoscope, a tympanic thermometer, a pulse oximeter, a respiration rate monitor, and the like.

20 Claims, 39 Drawing Sheets

U.S. PATENT DOCUMENTS

| | | | |
|---|---|---|---|
| 602,950 A | 4/1898 | Lau |
| 798,457 A | 8/1905 | Schmidt |
| 872,126 A | 11/1907 | Hart |
| 1,367,420 A | 2/1921 | Munter |
| 1,646,590 A | 10/1927 | Mildenberg |
| 1,898,652 A | 2/1933 | Williams |
| 2,079,694 A | 5/1937 | Lovell et al. |
| 2,223,570 A | 12/1940 | McMillin |
| 2,338,535 A | 1/1944 | Pfleumer |
| 2,354,397 A | 7/1944 | Miller |
| 2,436,853 A | 3/1948 | Coleman |
| 2,486,667 A | 11/1949 | Meister |
| 2,529,258 A | 11/1950 | Lobo |
| 2,543,284 A | 2/1951 | Gleason |
| 2,575,398 A | 11/1951 | Schroeder |
| 2,588,192 A | 3/1952 | Akerman et al. |
| 2,626,601 A | 1/1953 | Riley |
| 2,707,948 A | 5/1955 | Emerson |
| 2,762,200 A | 9/1956 | Huxley, III |
| 2,762,366 A | 9/1956 | Huxley, III et al. |
| 2,772,673 A | 12/1956 | Huxley, III |
| 2,779,329 A | 1/1957 | Huxley, III et al. |
| 2,780,222 A | 2/1957 | Polzin et al. |
| 2,818,853 A | 1/1958 | Huxley, III et al. |
| 2,832,335 A | 4/1958 | Huxley, III et al. |
| 2,869,537 A | 1/1959 | Chu |
| 2,899,955 A | 8/1959 | Huxley, III et al. |
| 2,918,917 A | 12/1959 | Emerson |
| 3,029,743 A | 4/1962 | Johns |
| 3,043,292 A | 7/1962 | Mendelson |
| 3,063,444 A | 11/1962 | Jobst |
| 3,068,856 A | 12/1962 | Bird et al. |
| 3,078,842 A | 2/1963 | Gray |
| 3,120,228 A | 2/1964 | Huxley, III |
| 3,164,100 A | 1/1965 | Hughes |
| 3,179,106 A | 4/1965 | Meredith |
| 3,191,596 A | 6/1965 | Bird et al. |
| 3,266,070 A | 8/1966 | O'Link |
| 3,288,132 A | 11/1966 | Meredith |
| 3,307,533 A | 3/1967 | Meredith et al. |
| 3,310,050 A | 3/1967 | Goldfarb |
| 3,333,581 A | 8/1967 | Robinson et al. |
| 3,424,165 A | 1/1969 | Moss |
| 3,454,000 A | 7/1969 | Bird et al. |
| 3,460,531 A | 8/1969 | Gardner |
| 3,481,327 A | 12/1969 | Drennen |
| 3,490,442 A | 1/1970 | Streu |
| 3,507,297 A | 4/1970 | Dann |
| 3,536,063 A | 10/1970 | Werding |
| 3,545,017 A | 12/1970 | Cohn |
| 3,556,088 A | 1/1971 | Leonardini |
| 3,566,862 A | 3/1971 | Schuh |
| 3,577,977 A | 5/1971 | Ritzinger, Jr et al. |
| 3,584,621 A | 6/1971 | Bird et al. |
| 3,630,196 A | 12/1971 | Bird et al. |
| 3,664,329 A | 5/1972 | Naylor |
| 3,664,337 A | 5/1972 | Lindsey et al. |
| 3,672,354 A | 6/1972 | Weber |
| 3,683,655 A | 8/1972 | White et al. |
| 3,742,899 A | 7/1973 | Alperin et al. |
| 3,742,939 A | 7/1973 | Sayer |
| 3,760,801 A | 9/1973 | Borgeas |
| D229,111 S | 11/1973 | Avery |
| 3,802,417 A | 4/1974 | Lang |
| 3,857,385 A | 12/1974 | Hampl |
| 3,880,152 A | 4/1975 | Nohmura |
| 3,885,554 A | 5/1975 | Rockwell, Jr. |
| 3,896,794 A | 7/1975 | McGrath |
| 3,905,651 A | 9/1975 | Hornung |
| 3,945,041 A | 3/1976 | Rhee |
| D240,463 S | 7/1976 | Jordan |
| 3,993,053 A | 11/1976 | Grossan |
| 4,003,373 A | 1/1977 | Spelio |
| 4,004,579 A | 1/1977 | Dedo |
| 4,020,834 A | 5/1977 | Bird |
| 4,023,566 A | 5/1977 | Martinmaas |
| 4,051,843 A | 10/1977 | Franetzki et al. |
| 4,066,072 A | 1/1978 | Cummins |
| 4,079,733 A | 3/1978 | Denton et al. |
| 4,093,944 A | 6/1978 | Muncheryan |
| 4,112,923 A | 9/1978 | Tomecek |
| 4,120,297 A | 10/1978 | Rabischong et al. |
| 4,133,305 A | 1/1979 | Steuer |
| 4,135,503 A | 1/1979 | Romano |
| 4,155,356 A | 5/1979 | Venegas |
| 4,175,297 A | 11/1979 | Robbins et al. |
| 4,178,922 A | 12/1979 | Curlee |
| 4,186,732 A | 2/1980 | Christoffel |
| 4,195,044 A | 3/1980 | Miller |
| 4,232,661 A | 11/1980 | Christensen |
| 4,239,039 A | 12/1980 | Thompson |
| 4,263,907 A | 4/1981 | Lindsey |
| 4,296,743 A | 10/1981 | Lasley |
| 4,311,135 A | 1/1982 | Brueckner et al. |
| 4,326,507 A | 4/1982 | Barkalow |
| 4,344,620 A | 8/1982 | Debski |
| 4,349,015 A | 9/1982 | Alferness |
| 4,397,306 A | 8/1983 | Weisfeldt et al. |
| 4,398,531 A | 8/1983 | Havstad |
| 4,413,357 A | 11/1983 | Sacks |
| 4,424,806 A | 1/1984 | Newman et al. |
| 4,429,688 A | 2/1984 | Duffy |
| 4,453,538 A | 6/1984 | Whitney |
| 4,464,172 A | 8/1984 | Lichtenstein |
| 4,471,773 A | 9/1984 | Bunnell et al. |
| 4,481,944 A | 11/1984 | Bunnell |
| 4,483,336 A | 11/1984 | Deitch |
| 4,507,816 A | 4/1985 | Smith, Jr. |
| 4,523,579 A | 6/1985 | Barry |
| 4,538,604 A | 9/1985 | Usry et al. |
| 4,546,764 A | 10/1985 | Gerber |
| 4,561,853 A | 12/1985 | Faulconer et al. |
| 4,577,626 A | 3/1986 | Marukawa et al. |
| 4,590,925 A | 5/1986 | Dillon |
| 4,592,349 A | 6/1986 | Bird |
| 4,621,621 A | 11/1986 | Marsalis |
| 4,624,244 A | 11/1986 | Taheri |
| 4,637,074 A | 1/1987 | Taheri |
| 4,637,386 A | 1/1987 | Baum |
| 4,646,366 A | 3/1987 | Nishida et al. |
| 4,676,232 A | 6/1987 | Olsson et al. |
| 4,682,588 A | 7/1987 | Curlee |
| 4,685,461 A | 8/1987 | Forssmann et al. |
| 4,693,256 A | 9/1987 | Talonn |
| 4,706,685 A | 11/1987 | Jones, Jr. et al. |
| 4,718,922 A | 1/1988 | Roffelsen |
| 4,736,750 A | 4/1988 | Valdespino et al. |
| 4,747,402 A | 5/1988 | Reese et al. |
| 4,753,226 A | 6/1988 | Zheng et al. |
| 4,762,302 A | 8/1988 | Bandou et al. |
| 4,779,615 A | 10/1988 | Frazier |
| 4,805,612 A | 2/1989 | Jensen |
| 4,805,613 A | 2/1989 | Bird |
| 4,809,706 A | 3/1989 | Watson et al. |
| 4,813,403 A | 3/1989 | Endo |
| 4,815,452 A | 3/1989 | Hayek |
| 4,823,784 A | 4/1989 | Bordoni et al. |
| 4,838,260 A | 6/1989 | Bird |
| 4,838,263 A | 6/1989 | Warwick et al. |
| 4,840,167 A | 6/1989 | Olsson et al. |
| 4,852,582 A | 8/1989 | Pell |
| 4,856,968 A | 8/1989 | Armbruster |
| 4,867,151 A | 9/1989 | Bird |
| 4,870,961 A | 10/1989 | Barnard |
| 4,873,937 A | 10/1989 | Binder et al. |
| 4,881,527 A | 11/1989 | Lerman |
| 4,886,057 A | 12/1989 | Nave |
| 4,908,895 A | 3/1990 | Walker |
| 4,921,408 A | 5/1990 | Kvinge et al. |
| 4,928,674 A | 5/1990 | Halperin et al. |
| 4,930,498 A | 6/1990 | Hayek |
| 4,930,501 A | 6/1990 | Bird |
| 4,944,306 A | 7/1990 | Alvino |
| 4,952,095 A | 8/1990 | Walters |
| 4,961,344 A | 10/1990 | Rodder |
| 4,966,141 A | 10/1990 | Bacaner et al. |
| 4,971,042 A | 11/1990 | Lerman |

| Patent No. | Date | Inventor |
|---|---|---|
| 4,977,889 A | 12/1990 | Budd |
| 4,982,735 A | 1/1991 | Yagata et al. |
| 4,986,269 A | 1/1991 | Hakkinen |
| 4,991,576 A | 2/1991 | Henkin et al. |
| 4,991,591 A | 2/1991 | Jones et al. |
| 5,007,412 A | 4/1991 | DeWall |
| 5,007,420 A | 4/1991 | Bird |
| 5,020,516 A | 6/1991 | Biondi et al. |
| 5,024,233 A | 6/1991 | Simecek et al. |
| 5,055,052 A | 10/1991 | Johnsen |
| 5,056,505 A | 10/1991 | Warwick et al. |
| 5,067,494 A | 11/1991 | Rienmueller et al. |
| 5,076,259 A | 12/1991 | Hayek |
| 5,097,821 A | 3/1992 | Eakin |
| 5,101,808 A | 4/1992 | Kobayashi et al. |
| 5,111,827 A | 5/1992 | Rantala |
| 5,113,852 A | 5/1992 | Murtonen |
| 5,116,088 A | 5/1992 | Bird |
| 5,117,819 A | 6/1992 | Servidio et al. |
| 5,137,026 A | 8/1992 | Waterson et al. |
| 5,158,094 A | 10/1992 | Miller |
| 5,159,935 A | 11/1992 | Sackner et al. |
| 5,165,398 A | 11/1992 | Bird |
| 5,173,325 A | 12/1992 | Knobbe et al. |
| 5,183,038 A | 2/1993 | Hoffman et al. |
| 5,188,097 A | 2/1993 | Hansen |
| 5,193,745 A | 3/1993 | Holm |
| 5,222,478 A | 6/1993 | Scarberry et al. |
| 5,231,981 A * | 8/1993 | Schreiber et al. ........ 128/205.23 |
| 5,233,974 A | 8/1993 | Senoue et al. |
| 5,235,967 A | 8/1993 | Arbisi et al. |
| 5,241,469 A | 8/1993 | Nelson et al. |
| 5,261,394 A | 11/1993 | Mulligan et al. |
| 5,269,659 A | 12/1993 | Hampton et al. |
| 5,277,175 A | 1/1994 | Riggs et al. |
| 5,277,194 A | 1/1994 | Hosterman et al. |
| 5,277,195 A | 1/1994 | Williams |
| 5,277,196 A | 1/1994 | Hankinson et al. |
| 5,279,163 A | 1/1994 | D'Antonio et al. |
| 5,293,875 A | 3/1994 | Stone |
| 5,299,599 A | 4/1994 | Farmer et al. |
| 5,313,955 A | 5/1994 | Rodder |
| 5,320,107 A | 6/1994 | O'Brien |
| 5,337,739 A | 8/1994 | Lehman |
| 5,360,009 A | 11/1994 | Herskovitz |
| 5,360,323 A | 11/1994 | Hsieh |
| 5,366,437 A | 11/1994 | Graston |
| 5,370,603 A | 12/1994 | Newman |
| 5,378,122 A | 1/1995 | Duncan |
| 5,383,470 A | 1/1995 | Kolbly |
| 5,398,676 A | 3/1995 | Press et al. |
| 5,402,938 A | 4/1995 | Sweeney |
| 5,415,161 A | 5/1995 | Ryder |
| 5,419,326 A | 5/1995 | Harnoncourt |
| 5,431,154 A | 7/1995 | Seigel et al. |
| 5,437,615 A | 8/1995 | Pekar et al. |
| 5,453,081 A | 9/1995 | Hansen |
| 5,455,159 A | 10/1995 | Mulshine et al. |
| 5,479,920 A | 1/1996 | Piper et al. |
| 5,490,820 A | 2/1996 | Schock et al. |
| 5,492,115 A | 2/1996 | Abramov et al. |
| 5,496,262 A | 3/1996 | Johnson, Jr. et al. |
| 5,497,766 A | 3/1996 | Foster et al. |
| 5,508,908 A | 4/1996 | Kazama et al. |
| 5,522,380 A | 6/1996 | Dwork |
| 5,548,843 A | 8/1996 | Chase et al. |
| 5,562,101 A | 10/1996 | Hankinson et al. |
| 5,562,604 A | 10/1996 | Yablon et al. |
| 5,564,432 A | 10/1996 | Thomson |
| 5,569,122 A | 10/1996 | Cegla |
| 5,569,170 A | 10/1996 | Hansen |
| 5,570,682 A | 11/1996 | Johnson |
| 5,575,762 A | 11/1996 | Peeler et al. |
| 5,606,754 A | 3/1997 | Hand et al. |
| 5,617,844 A | 4/1997 | King |
| 5,624,384 A | 4/1997 | Chen |
| D379,396 S | 5/1997 | Rongo et al. |
| 5,642,735 A | 7/1997 | Kolbly |
| 5,647,370 A | 7/1997 | Harnoncourt |
| 5,673,687 A | 10/1997 | Dobson et al. |
| D386,564 S | 11/1997 | Mycroft |
| 5,694,919 A | 12/1997 | Rubsamen et al. |
| 5,715,812 A | 2/1998 | Deighan et al. |
| 5,715,831 A | 2/1998 | Johnson |
| 5,720,709 A | 2/1998 | Schnall |
| 5,735,287 A | 4/1998 | Thomson |
| 5,737,287 A | 4/1998 | Lee |
| 5,738,089 A | 4/1998 | Hoshi et al. |
| 5,738,637 A | 4/1998 | Kelly et al. |
| 5,743,270 A | 4/1998 | Gazzara et al. |
| 5,769,797 A | 6/1998 | Van Brunt et al. |
| 5,769,800 A | 6/1998 | Gelfand et al. |
| 5,806,512 A | 9/1998 | Abramov et al. |
| D400,239 S | 10/1998 | Miller et al. |
| 5,816,246 A | 10/1998 | Mirza |
| 5,817,037 A | 10/1998 | Zurbay |
| 5,827,179 A | 10/1998 | Lichter et al. |
| 5,830,164 A | 11/1998 | Cone et al. |
| 5,833,711 A | 11/1998 | Schneider, Sr. |
| 5,836,751 A | 11/1998 | De Villiers |
| 5,840,049 A | 11/1998 | Tumey et al. |
| 5,848,878 A | 12/1998 | Conti et al. |
| 5,862,802 A | 1/1999 | Bird |
| 5,871,008 A | 2/1999 | Poon et al. |
| 5,891,062 A | 4/1999 | Schock et al. |
| 5,910,071 A | 6/1999 | Hougen |
| 5,913,249 A | 6/1999 | Weckström |
| 5,924,994 A | 7/1999 | Harbrecht et al. |
| 5,938,627 A * | 8/1999 | Hickman ........................ 601/149 |
| 5,941,241 A | 8/1999 | Weinstein et al. |
| 5,980,466 A | 11/1999 | Thomson |
| 5,984,872 A | 11/1999 | Vriend |
| 5,984,873 A | 11/1999 | Crumb et al. |
| 5,988,166 A | 11/1999 | Hayek |
| 5,997,483 A | 12/1999 | Johnson |
| 5,997,488 A | 12/1999 | Gelfand et al. |
| 6,009,870 A | 1/2000 | Tkatchouk |
| 6,010,458 A | 1/2000 | Roberts |
| 6,010,469 A | 1/2000 | McAtee |
| 6,015,388 A | 1/2000 | Sackner et al. |
| D421,298 S | 2/2000 | Kenyon et al. |
| 6,019,731 A | 2/2000 | Harbrecht et al. |
| 6,030,353 A | 2/2000 | Van Brunt |
| 6,036,662 A | 3/2000 | Van Brunt et al. |
| 6,042,551 A | 3/2000 | Harbrecht et al. |
| 6,066,101 A | 5/2000 | Johnson et al. |
| 6,068,602 A | 5/2000 | Tham et al. |
| 6,077,239 A | 6/2000 | Lin |
| D427,675 S | 7/2000 | Hansel |
| 6,090,049 A | 7/2000 | Cha |
| 6,113,549 A | 9/2000 | Johnson |
| 6,123,076 A | 9/2000 | Roberts et al. |
| 6,126,613 A | 10/2000 | Edwards et al. |
| 6,142,148 A | 11/2000 | Weckström et al. |
| 6,155,996 A | 12/2000 | Van Brunt et al. |
| 6,174,295 B1 | 1/2001 | Cantrell et al. |
| 6,176,833 B1 | 1/2001 | Thomson |
| 6,179,793 B1 | 1/2001 | Rothman et al. |
| 6,193,677 B1 | 2/2001 | Cady |
| 6,210,345 B1 | 4/2001 | Van Brunt |
| 6,238,353 B1 | 5/2001 | Weinstein et al. |
| 6,241,683 B1 | 6/2001 | Macklem et al. |
| 6,254,555 B1 | 7/2001 | Sevier et al. |
| 6,254,556 B1 | 7/2001 | Hansen et al. |
| 6,269,810 B1 | 8/2001 | Brooker et al. |
| 6,283,132 B1 | 9/2001 | Stephens et al. |
| 6,283,923 B1 | 9/2001 | Finkelstein et al. |
| 6,340,025 B1 | 1/2002 | Van Brunt |
| D453,560 S | 2/2002 | Van Brunt |
| D454,393 S | 3/2002 | Lynch et al. |
| 6,355,002 B1 | 3/2002 | Faram et al. |
| 6,359,775 B1 * | 3/2002 | Revis ........................ 361/679.27 |
| 6,379,316 B1 | 4/2002 | Van Brunt et al. |
| 6,398,727 B1 | 6/2002 | Bui et al. |
| 6,415,791 B1 | 7/2002 | Van Brunt |
| 6,416,471 B1 | 7/2002 | Kumar et al. |
| 6,435,175 B1 | 8/2002 | Stenzler |
| 6,454,708 B1 | 9/2002 | Ferguson et al. |

| | | | |
|---|---|---|---|
| 6,466,133 B1 | 10/2002 | Skardon |
| 6,468,237 B1 | 10/2002 | Lina |
| 6,471,663 B1 | 10/2002 | Van Brunt et al. |
| D468,011 S | 12/2002 | Lithgow et al. |
| 6,488,641 B2 | 12/2002 | Hansen |
| 6,508,772 B2 | 1/2003 | Vilozni |
| 6,544,202 B2 | 4/2003 | McEwen et al. |
| 6,581,596 B1 | 6/2003 | Truitt et al. |
| 6,581,600 B2 | 6/2003 | Bird |
| 6,595,203 B1 | 7/2003 | Bird |
| 6,605,050 B2 | 8/2003 | Hansen |
| 6,609,016 B1 | 8/2003 | Lynn |
| 6,656,115 B1 | 12/2003 | Miyazaki et al. |
| 6,656,129 B2 | 12/2003 | Niles et al. |
| 6,676,614 B1 | 1/2004 | Hansen et al. |
| D487,311 S | 3/2004 | Lithgow et al. |
| 6,699,188 B2 | 3/2004 | Wessel |
| 6,729,327 B2 | 5/2004 | McFarland, Jr. |
| 6,731,970 B2 | 5/2004 | Schlossbauer et al. |
| 6,732,581 B1 | 5/2004 | Torresin |
| 6,736,785 B1 | 5/2004 | Van Brunt |
| 6,764,455 B2 | 7/2004 | Van Brunt et al. |
| 6,805,118 B2 | 10/2004 | Brooker et al. |
| D498,528 S | 11/2004 | Van Brunt et al. |
| 6,880,556 B2 | 4/2005 | Uchiyama et al. |
| 6,910,479 B1 | 6/2005 | Van Brunt |
| 6,916,298 B2 | 7/2005 | VanBrunt et al. |
| 6,958,046 B2 | 10/2005 | Warwick et al. |
| 7,013,894 B2 | 3/2006 | McFarland, Jr. |
| 7,018,348 B2 | 3/2006 | Van Brunt et al. |
| 7,077,133 B2 | 7/2006 | Yagi et al. |
| 7,115,104 B2 | 10/2006 | Van Brunt et al. |
| 7,121,808 B2 | 10/2006 | Van Brunt et al. |
| 7,131,439 B2 | 11/2006 | Blacker et al. |
| 7,191,780 B2 | 3/2007 | Faram |
| 7,455,062 B2* | 11/2008 | Roehl et al. ............ 128/204.21 |
| 7,654,261 B1* | 2/2010 | Rockhold ............... 128/204.18 |
| 2002/0016560 A1 | 2/2002 | Hansen |
| 2002/0077765 A1* | 6/2002 | Mault ........................ 702/127 |
| 2002/0082531 A1 | 6/2002 | Van Brunt et al. |
| 2002/0087097 A1 | 7/2002 | Van Brunt et al. |
| 2002/0111571 A1 | 8/2002 | Warwick et al. |
| 2003/0028131 A1 | 2/2003 | Van Brunt et al. |
| 2003/0140921 A1 | 7/2003 | Smith et al. |
| 2003/0145849 A1 | 8/2003 | Drinan et al. |
| 2003/0183226 A1 | 10/2003 | Brand et al. |
| 2003/0212350 A1 | 11/2003 | Tadlock |
| 2004/0017709 A1 | 1/2004 | Braceras |
| 2004/0064076 A1 | 4/2004 | Bilgi |
| 2004/0097842 A1 | 5/2004 | Van Brunt et al. |
| 2004/0097843 A1 | 5/2004 | Van Brunt et al. |
| 2004/0097844 A1 | 5/2004 | Van Brunt et al. |
| 2004/0097845 A1 | 5/2004 | Van Brunt |
| 2004/0097846 A1 | 5/2004 | Van Brunt et al. |
| 2004/0097847 A1 | 5/2004 | Van Brunt et al. |
| 2004/0097848 A1 | 5/2004 | Van Brunt et al. |
| 2004/0097849 A1 | 5/2004 | Van Brunt |
| 2004/0158177 A1 | 8/2004 | Van Brunt et al. |
| 2005/0054956 A1 | 3/2005 | Gagne |
| 2005/0150489 A1 | 7/2005 | Dunfield et al. |
| 2005/0172954 A1 | 8/2005 | Smith et al. |
| 2005/0217666 A1 | 10/2005 | Fink et al. |
| 2006/0009718 A1 | 1/2006 | Van Brunt et al. |
| 2006/0036199 A1 | 2/2006 | Warwick et al. |
| 2006/0058716 A1* | 3/2006 | Hui et al. .................. 601/152 |
| 2007/0004992 A1 | 1/2007 | Van Brunt et al. |

FOREIGN PATENT DOCUMENTS

| | | |
|---|---|---|
| EP | 0542383 A2 | 5/1993 |
| EP | 0584505 A1 | 3/1994 |
| EP | 0904830 A1 | 3/1999 |
| FR | 1480327 | 5/1967 |
| FR | 2507064 | 12/1982 |
| GB | 616173 | 1/1949 |
| GB | 2 365 780 A | 2/2002 |
| JP | 2001-001895 | 1/2001 |
| JP | 2001-051396 | 2/2001 |
| JP | 2001-073499 | 3/2001 |
| SE | 105158 | 8/1942 |
| SE | 143165 | 12/1953 |
| WO | WO 97/18003 A1 | 5/1997 |
| WO | WO 01/15598 A1 | 3/2001 |
| WO | WO 02/06673 A1 | 1/2002 |

OTHER PUBLICATIONS

R. Agostinis, et al., "*High-Frequency Chest Compression in Combination with Hypertonic Saline Improves Induced Sputum Cytologic Yield*"(Abstract), ATS International Conference, 1 pg., May 1995.

"*Cancer Facts & Figures—1996*", American Cancer Society, 36 pgs., Jul. 1996.

"*Early Lung Cancer Detection: Summary and Conclusions*", Screening for Lung Cancer, Am Rev Respir Dis, vol. 130, pp. 565-570, 1984.

R. Fontana et al., "*Lung Cancer Screening: The Mayo Program*", Journal of Occupational Medicine, vol. 28, No. 8, pp. 746-750, Aug. 1986.

R. L. Jones et al., "*Use of High-Frequency chest Compression Plus Hypertonic Saline Aerosol to Provide Sputum Samples for Diagnosis of Lung Cancer*" (Abstract), Alberta Respiratory Diseases Symposium, Jasper, Alberta, 1 pg., 1995.

T. C. Kennedy et al., "*Efficacy of Two Sputum Collection Techniques in Patients with Air Flow Obstruction*", Acta Cytologica, vol. 43, pp. 630-636, Jul.-Aug. 1999.

C. MacAulay, et al., "*Malignancy Associated Changes in Epithelial Cells from Bronchial Biopsies*" (Abstracts), XVII World Congress on Diseases of the Chest, p. 260.

L. Mao, "*Detection of Oncogene Mutations in Sputum Precedes Diagnosis of Lung Cancer*", Cancer Research 54, pp. 1634-1637, Apr. 1994.

L. Mao, "*Microsatellite Alterations as Clonal Markers for the Detection of Human Cancer*" (Medical Sciences), Proc. Natl. Acad. Sci. USA, vol. 91, pp. 9871-9875, Oct. 1994.

M. Mckinnon, et al., "*Optimal Sputum Cytology Collection Method*", Chest (Supplement), vol. 110, No. 4, p. 1, Oct. 1996.

P. W. Payne, Ph.D., et al., "*Sputum Screening by Quantitative Microscopy: A Reexamination of a Portion of the National Cancer Institution Cooperative Early Lung Cancer Study*", Mayo Clinic Proceedings, vol. 72, No. 8, pp. 697-704, Aug. 1997.

B. Pedersen et al., "*The Value of Provoked Expectoration in Obtaining Sputum Samples for Cytologic Investigation*", vol. 29, No. 5, pp. 750-752, Sep.-Oct. 1985.

D. Rome, et al., "*A Direct Comparison of Natural and Aerosol Produced Sputum Collected from 776 Asymptomatic Men*", Acta Cytologica, pp. 173-176, May-Jun. 1961.

D. Sidransky, "*Importance of Chromosome 9p Loss in Human Lung Cancer*", Journal of the National Cancer Institute (Editorials) vol. 87, No. 16, 2 pgs., Aug. 1995.

M. Tockman et al., "*Sensitive and Specific Monoclonal Antibody Recognition of Human Lung Cancer Antigen on Preserved Sputum Cells: A New Approach to Early Lung Cancer Detection*", Journal of Clinical Oncology, vol. 6, No. 11, pp. 1685-1693, Nov. 1988.

M. Tockman, "*Survival and Mortality from Lung Cancer in a Screened Population*", The John Hopkins Study, Chest (Supplement), vol. 89, No. 4, pp. 324-325, Apr. 1986.

M. Tockman, et al., "*The Early Detection of Second Primary Lung Cancers by Sputum Immunostaining*", Chest (Supplement), vol. 106, No. 6, pp. 385-390, Dec. 1994.

W. O. Umiker, M.D. et al., "*Collection of Sputum for Cytologic Examination, Spontaneous vs. Artificially Produced Sputum*", The New England Journal of Medicine, vol. 262, No. 11, pp. 565-566, Mar. 1960.

P. Wingo, Ph.D., MS, et al., "*Cancer Statistics, 1995*", CA Cancer J Clin, vol. 45, No. 1, pp. 8-30, Jan.-Feb. 1995.

International preliminary report on patentability from PCT/US2007/063864 dated Sep. 25, 2008.

A Manual on VDR-Volumetric Diffusive Respiration (VDR) The VDR-4 Percussionator for the Most Challenging Patients Requiring Mechanical Cardiopulmonary Care; Percussionaire, Corporation, Idaho, Copyright 1995 (75 pages).

Bird Demand CPAP, Bird Technical Information Manual, Copyright 1977 Bird Corp. (138 pages).
The Percussionaire Gold Edition IPV-1S(r) Universal Percussionator—Form 33120 Percussionaire Corporation, Idaho (2 pages).
The Basic Institutional Intrapulmonary Percussionator—Percussionaire Model IPC-1—Percussionaire Corporation, Idaho (2 pages).
The Bird—Instructor Reference manual by Forrest M. Bird for the Bird Institute of Respiratory Technology, Apr. 1976 (14 pages).
Organization and Set Up of the Percussive VDR Intensive Care Breathing Circuit VDR Failsafe Breathing Circuit for Intensive Care—Percussionaire, Corporation, Idaho (31 pages).

Intrapulmonary Percussive Ventilation IPV Discussion paper, Copyright Percussionaire 2000 (30 pages).
Specifications for Spankers Respirators, Copyright Percussionaire 1985 (6 pages).
Percussionaire Products Sheet, Dec. 12, 2002 (2 pages).
IPV-1C Institutional Intrapulmonary Percussionator spec., by Percussionaire Oct. 28, 2001 (2 pages).
IPV Users Manual, Copyright Percussionaire Dec. 1, 2000 (48 pages).

* cited by examiner

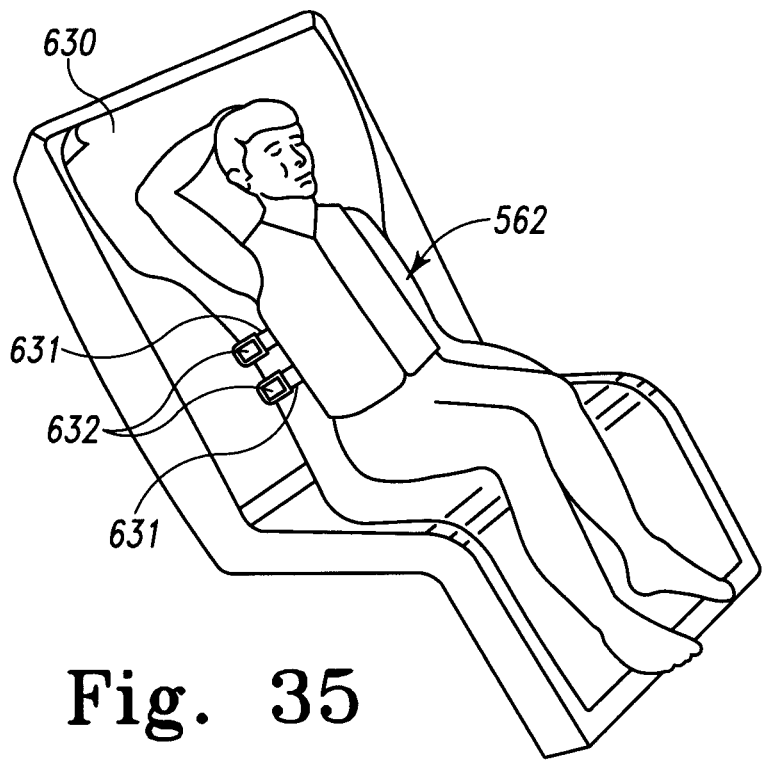
Fig. 35
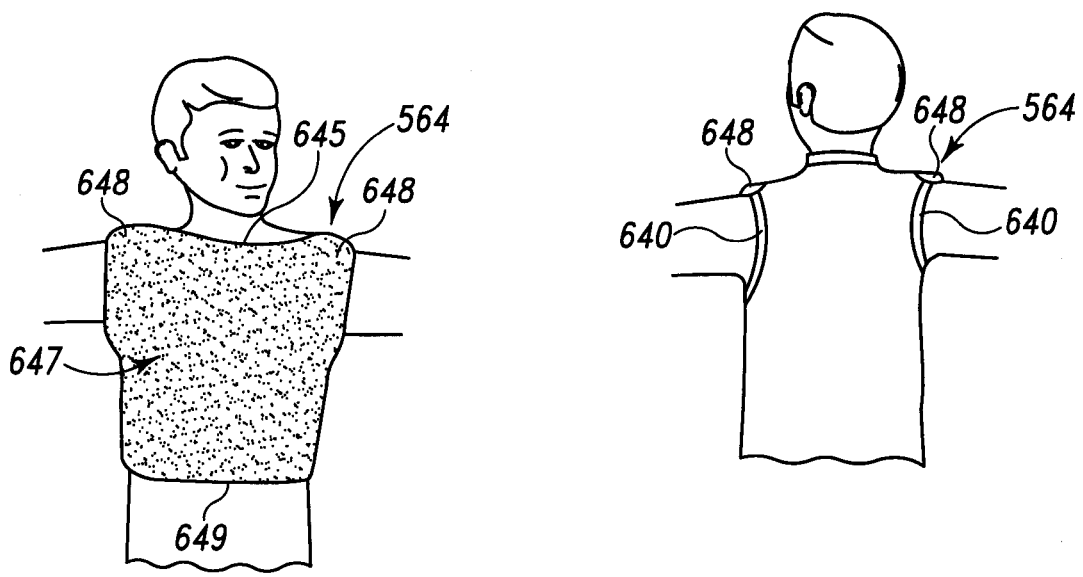
Fig. 36
Fig. 37

HIGH FREQUENCY CHEST WALL OSCILLATION SYSTEM

This application claims the benefit, under 35 U.S.C. §119 (e), of U.S. Provisional Application No. 60/782,383 which was filed Mar. 15, 2006 and which is hereby incorporated by reference herein.

BACKGROUND OF THE INVENTION

The present disclosure relates generally to high frequency chest wall oscillation (HFCWO) therapy systems, and more particularly, to HFCWO therapy systems suitable for use in a hospital or healthcare facility.

Manual percussion techniques of chest physiotherapy have been used for a variety of diseases, such as cystic fibrosis, emphysema, asthma and chronic bronchitis, to remove excess mucus that collects in the lungs. To bypass dependency on a caregiver to provide this therapy, chest wall oscillation devices have been developed to deliver HFCWO therapy to a patient. U.S. Patent Application Publication No. US 2004/0097842 discloses an illustrative HFCWO therapy system, which is hereby incorporated by reference herein.

SUMMARY OF THE INVENTION

The present invention comprises an apparatus or system that has one or more of the following features or combinations thereof, which alone or in any combination may comprise patentable subject matter:

The apparatus may comprise a housing and a therapy system carried by the housing and operable to deliver one or more respiratory therapies to a patient. The apparatus may further comprise an assessment system carried by the housing and operable to assess the efficacy of at least one of the respiratory therapies. The therapy system may be operable to deliver any one or more of the following therapies: HFCWO therapy, a positive expiratory pressure (PEP) therapy, a nebulizer therapy, an intermittent positive pressure breathing (IPPB) therapy, a cough assist therapy and/or other types of suction therapy (e.g., negative pressure wound therapy), and a bronchial dilator therapy. The assessment system may comprise any one or more of the following devices: a flow meter, a spirometer, an electronic stethoscope, a tympanic thermometer, a pulse oximeter, and a respiration rate monitor.

The apparatus may include a display operable to show data relating to the therapy system and/or relating to the assessment system. The apparatus may include a controller operable to control at least two of the respiratory therapies. In some embodiments, the controller is operable to control the assessment system and at least one of the respiratory therapies. Data from the assessment system may be used to adjust at least one of the respiratory therapies. In some embodiments, data from the assessment system is used to adjust the frequency and intensity of the HFCWO therapy.

The therapy system may comprise an air pulse generator operable to provide a pressure having a steady state pressure component and an oscillating pressure component. The therapy system may include a controller operable to control the amplitude of the steady state pressure component, the frequency of the oscillating pressure component and the duration of the HFCWO therapy. The display may be operable to show data relating to the HFCWO therapy. The controller may analyze data from a spirometer and show the data on the display. Data from the spirometer may be used to adjust the amplitude of the steady state pressure component and the frequency of the oscillating pressure component. The apparatus may include a nebulizer coupled to a pressurized air source located within the housing. The pressurized air source may comprise a compressor.

The apparatus may comprise a self-oscillating valve coupled to a source of pressurized air and an air amplifier that is coupled to the self-oscillating valve and that is coupled to an inflatable bladder. The pressurized air source may comprise a hospital pressurized air outlet. The self-oscillating valve may be driven by pressurized air from the pressurized air source to produce first pressure pulses having a first pressure and a first volume flow rate for application to the air amplifier. The air amplifier may convert the first pressure pulses into second pressure pulses that are communicated to the bladder. The second pressure pulses may have a second pressure that is smaller than the first pressure and having a second volume flow rate that is greater than the first volume flow rate. The apparatus may have a pressure control operable to vary the amplitude of the air pulses, a frequency control operable to vary the frequency of the air pulses, and a timer control to provide an alarm signal to indicate that the set therapy time has elapsed. The air pulse generator may include a housing having a hanger configured to suspend the housing from a support device, such as a chair, a hospital bed, a cart, a wheeled pedestal, or a rollable stand. The self-oscillating valve and the air amplifier may be located within the housing.

The apparatus may comprise a housing, an air pulse generator carried by the housing and operable to deliver HFCWO therapy to a patient, a controller carried by the housing and operable to control the HFCWO therapy, and a wheeled pedestal coupled to the housing. A storage compartment may be coupled to the pedestal. The pedestal may be vertically adjustable to support the housing at a selected one of a plurality of elevations. The apparatus may include a remote on/off switch coupled to the controller. Supplies associated with the HFCWO therapy may be stored in the storage compartment. The storage compartment may be located below the housing. The storage compartment may comprise a pair of bins mounted on opposite sides of the pedestal. The bins may have hinged lids. The housing may include a handle that is gripped to maneuver the housing and the wheeled pedestal along a floor.

The apparatus may comprise a wheeled housing having a first storage compartment, a respiratory therapy system carried by the housing and operable to deliver respiratory therapy to a patient, and a display carried by the housing and operable to show data relating to the respiratory therapy. The display may be movable between a first position in which the first storage compartment is accessible and a second position in which the display blocks access to the first storage compartment. The housing may further comprise a second storage compartment located below the first storage compartment. The apparatus may include an assessment system carried by the housing and operable to assess the efficacy of the respiratory therapy. The assessment system may comprise a spirometer. The apparatus may include a controller carried by the housing and operable to control the respiratory therapy. The respiratory therapy system may system comprise a HFCWO therapy system. The controller may be configured to analyze data from the assessment system and show the data on the display. The apparatus may further comprise a nebulizer coupled to a pressurized air source carried by the housing. The pressurized air source may be a compressor.

The apparatus may include a housing and an air pulse generator operable to deliver a HFCWO therapy to a patient. The air pulse generator may have a first pressure source carried by the housing and a second pressure source carried by the housing. The second pressure source may be configured to be coupled to a nebulizer. The first pressure source may comprise a blower. The second pressure source may comprise a compressor. Additionally or alternatively, the second pressure source may comprise a vacuum source carried by the housing and configured to be coupled to a suction therapy device. The pressure source and/or vacuum source may be coupled to a port located on a wall of the housing. The source may supply pressurized air and vacuum to the port in first and second modes of operation, respectively. The source may supply pressurized air and then vacuum to the port so as to produce a cough assist to a patient.

The HFCWO therapy system may be used with a plurality of patients. The system may comprise an air pulse generator operable to produce oscillating pressure that is applied to a patient, a controller operable to control the operation of the air pulse generator in accordance with a set of operating parameters, a memory for storing the operating parameters for each of the plurality of patients, and a user interface apparatus usable to select one of the patients from the plurality of patients for whom the system is used. The controller may be configured to automatically operate the air pulse generator in accordance with the operating parameters associated with the selected patient.

The user interface apparatus may comprise a display. The display may be signaled by the controller to display a plurality of user interface screens. One of the plurality of user interface screens may be a home screen having a plurality of icons. Each icon may be associated with a respective one of the plurality of user interface screens. The plurality of icons may include one or more of a patient icon, a spirometry icon, a vest-and-spirometry icon, a vest program icon, a data download icon, and a help icon. Selection of any of the plurality of icons results in an associated screen being displayed on the display.

The HFCWO therapy system may comprise a garment, such as a wrap or a vest, having a double fabric layer providing at least one inflatable bladder, or between which at least one inflatable bladder is situated. A pair of hoses may be routed through associated slits in the wrap to establish fluid communication with the bladder. In some embodiments, a garment for HFCWO therapy may comprise a mesh fabric layer and at least one inflatable bladder. In some garment embodiments, a layer facing the patient may be a low air loss layer having a plurality of perforations through which air is expelled toward the patient to enhance cooling of the patient and/or to enhance evaporation of perspiration. In some embodiments, the garment is couplable to a sheet under a patient via one or more couplers. The couplers may comprise one or more garters each having a strap coupled to the garment and having a clip that releasably couples to the sheet. An inner layer of material of the garment may be a wicking material that wicks moisture away from the patient. The garment may have at least one cooling fluid channel configured to receive a cooling fluid therein to cool the patient during HFCWO therapy.

A garment to be worn by a patient during high frequency chest wall oscillation (HFCWO) therapy may be made at least, in part, from clinical camouflage material and may have at least one inflatable bladder. The clinical camouflage material may be impregnated with activated charcoal. Alternatively or additionally, the clinical camouflage material may be impregnated with an antimicrobial.

A garment to be worn by a patient during high frequency chest wall oscillation (HFCWO) therapy may comprise a front panel configured to cover a front of a patient's chest and having at least one inflatable bladder. A right strap may be coupled at two locations to the front panel. The right strap may cooperate with the front panel to form a first loop around a patient's right arm. A left strap may be coupled at two locations to the front panel. The left strap may cooperate with the front panel to form a second loop around a patient's left arm. In lieu of the right and left straps, the garment may have a neck strap and a torso strap. The neck strap may be coupled at two locations to the front panel and may cooperate with the front panel to form a first loop around a patient's neck. The torso strap may be coupled at two locations to the front panel and may cooperate with the front panel to form a second loop around a patient's torso.

An apparatus to be worn by a patient during high frequency chest wall oscillation (HFCWO) therapy may comprise a garment having a plurality of air chambers and a plurality of flow regulators carried by the garment. The garment may cover at least a portion of a patient's chest. The flow regulators may be openable to permit pressurized air to reach an associated one of the plurality of air chambers and the flow regulators may be closeable to block pressurized air from reaching the associated one of the plurality of air chambers.

The flow regulators may each have a knob which is accessible on the exterior of the garment to open and close the associated one of the plurality of air chambers. One or more of the plurality of air chambers may have a cut-out to accommodate a portion of an associated one of the knobs. The plurality of air chambers may comprise side-by-side pairs of first and second air chambers and each of the first air chambers may be situated vertically above an associated one of the second air chambers. The flow regulators may include a pair of side-by-side valves and each of the side-by-side valves may be located in a space between the associated first and second air chambers. When each of the side-by-side valves are opened, the first and second air chambers may be in fluid communication and when each of the side-by-side valves are closed, the fluid communication between the first and second air chambers may be blocked. The plurality of air chambers may further comprise a side-by-side pair of third air chambers and each of the third air chambers may be situated vertically below an associated one of the second air chambers. The flow regulators may comprise an additional pair of side-by-side valves which may be located in a space between the associated second and third air chambers.

Each of the first air chambers have a first volume that may be larger than a second volume of each of the second air chambers and the second volume may be larger than a third volume of each of the third air chambers. The garment may be openable and closeable along a split line that extends generally vertically between the side-by-side pairs of first, second, and third air chambers.

The garment may further comprise a hose interconnecting a first air chamber of the plurality of air chambers and a second air chamber of the plurality of air chambers. The plurality of flow regulators may comprise a hose clamp coupled to the hose. The hose clamp may be accessible to be manipulated to open and close the hose. The first air chamber to which the hose is coupled may be located above the second air chamber to which the hose is coupled.

According to aspects of this disclosure, a system for applying high frequency chest wall oscillation (HFCWO) therapy to a patient may comprise a garment that has a plurality of air chambers and that is configured to cover at least a portion of the patient's chest. The system may further have an air pulse generator operable to produce a first oscillating pressure and a second oscillating pressure. The first oscillating pressure may be communicated to at least a first air chamber of the plurality of air chambers and the second oscillating pressure may be communicated to at least a second air chamber of the plurality of air chambers.

The air pulse generator may have a first oscillating diaphragm assembly operable at a first frequency associated with the first oscillating pressure and may have a second oscillating diaphragm assembly operable at a second frequency associated with the second oscillating pressure. The system may also have a first blower coupled to the first oscillating diaphragm assembly and operable to establish a first baseline pressure associated with the first oscillating pressure and may further have a second blower coupled to the second oscillating diaphragm assembly and operable to establish a second baseline pressure associated with the second oscillating pressure.

According to another aspect of this disclosure, a high frequency chest wall oscillation (HFCWO) therapy system may comprise an air pulse generator operable to produce an oscillating pressure and a coolant system operable to deliver a cooling fluid. The system my further comprise a garment configured to be worn by a patient and cover at least a portion of the patient's chest. The garment may have at least one inflatable air chamber in communication with the oscillating pressure and at least one channel to receive the cooling fluid.

Additional features, which alone or in combination with any other feature(s), such as those listed above and those listed in the appended claims, may comprise patentable subject matter and will become apparent to those skilled in the art upon consideration of the following detailed description of illustrative embodiments exemplifying the best mode of carrying out the embodiments as presently perceived.

BRIEF DESCRIPTION OF THE DRAWINGS

The detailed description particularly refers to the accompanying figures in which:

FIG. 35 is a perspective view showing a sheet clamped vest similar to the wrap shown in FIG. 28;

FIG. 36 is a front perspective view of a garment having a front panel;

FIG. 37 is rear perspective view of the garment of FIG. 36 showing left and right straps that cooperate with the front panel to form loops that receive the patients left and right arms, respectively;

FIG. 41 is a screen shot of a patient screen of the system of FIGS. 12-15 showing a list of patients for which operating parameters are stored and showing patient information pertaining to a selected one of the patients;

FIG. 42 is a screen shot of a patient edit screen of the system of FIGS. 12-15 showing various touchscreen keys which are used to edit the patient information stored in the system;

DETAILED DESCRIPTION OF THE DRAWINGS

The term "air" as used in the specification and claims is used broadly to include regular or ambient air, medical air, nitrogen, oxygen, and any other breathable, as well as non-breathable, gas available in a hospital or healthcare facility. The terms "hospital" and "healthcare facility" are used interchangeably, and each is intended to broadly include hospitals, healthcare facilities, nursing homes, outpatient clinics, doctors' offices, medical care facilities, and the like. The terms "respiratory therapy" and "airway clearance therapy" are used interchangeably, and each is intended to broadly include a HFCWO therapy, a positive expiratory pressure (PEP) therapy, a nebulizer therapy, an intermittent positive pressure breathing (IPPB) therapy, a cough assist therapy, a suction therapy, a bronchial dilator therapy, and the like. The term "vacuum" as used in the specification and claims is used broadly to include negative pressures or pressures below atmospheric pressure.

Figure 1:
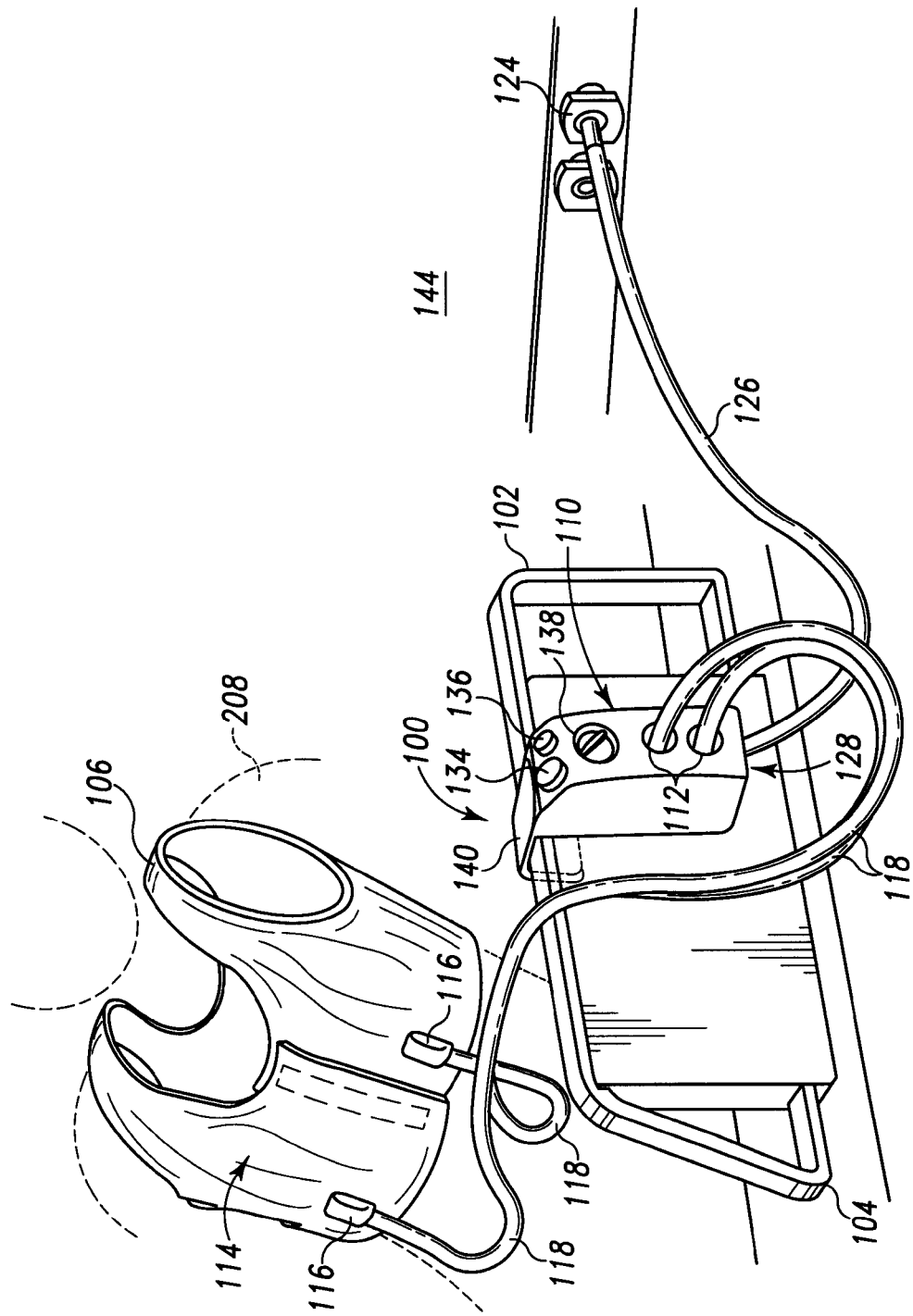
FIG. 1 is a perspective view of a first embodiment of a HFCWO therapy system showing the HFCWO therapy system supported on a siderail of a hospital bed, a hose supplying pressurized air to the HFCWO therapy system, and a pair of hoses coupled to the HFCWO therapy system and coupled to a vest positioned on a patient supported on the bed.

FIGS. 1-4 illustrate a first embodiment 100 of a HFCWO therapy system according to this disclosure. As shown in FIG. 1, the HFCWO therapy system 100 is supported on a siderail 102 of a hospital bed 104. The system 100 generates HFCWO air pulses for application to an inflatable vest 106 positioned on a patient 108. The system 100 includes a housing 110 having a pair of air ports 112. The vest 106 includes an inflatable bladder 114 having a pair of air ports 116. A pair of hoses 118 are releasably coupled to the ports 112 of the housing 110 and the ports 116 of the bladder 114. The air pulses are routed from the system 100 to the vest 106 via the hoses 118. U.S. Pat. No. 6,916,298, which is hereby incorporated by reference herein, discloses an illustrative HFCWO therapy vest which may be coupled to system 100 in lieu of illustrative vest 106. In addition, any of the garments disclosed herein and shown in FIGS. 24-40 may be used with system 100, if desired.

Figure 4:
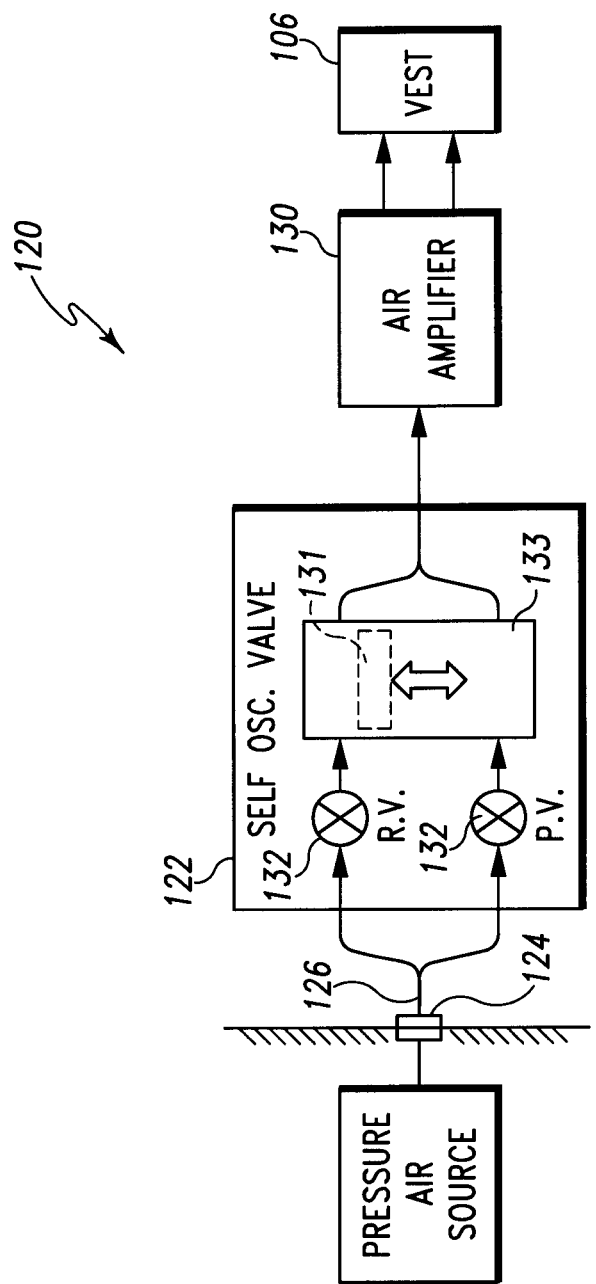
FIG. 4 is a block diagram of the HFCWO therapy system of FIGS. 1-3.
Figure 5:
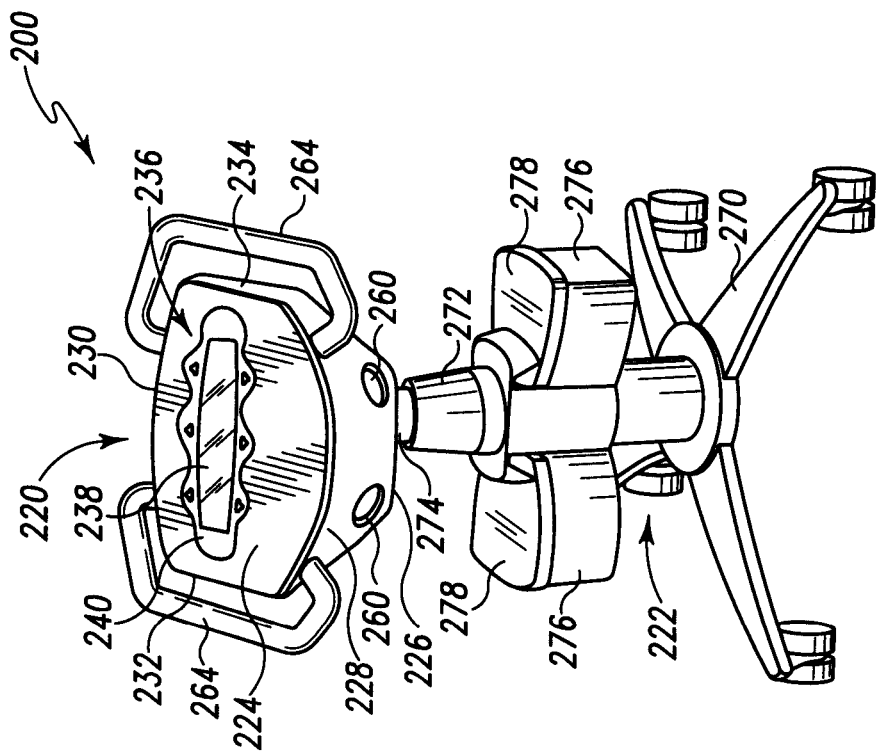
FIG. 5 is a perspective view showing a second embodiment of a HFCWO therapy system in which a housing is supported on a wheeled pedestal, the housing carries a 2-line display screen, a pair of handles, and two air ports through which high frequency air pulses are routed from the HFCWO therapy system to a garment worn by a patient, and in which the pedestal supports a pair of storage bins having hinged lids.
Figure 6:
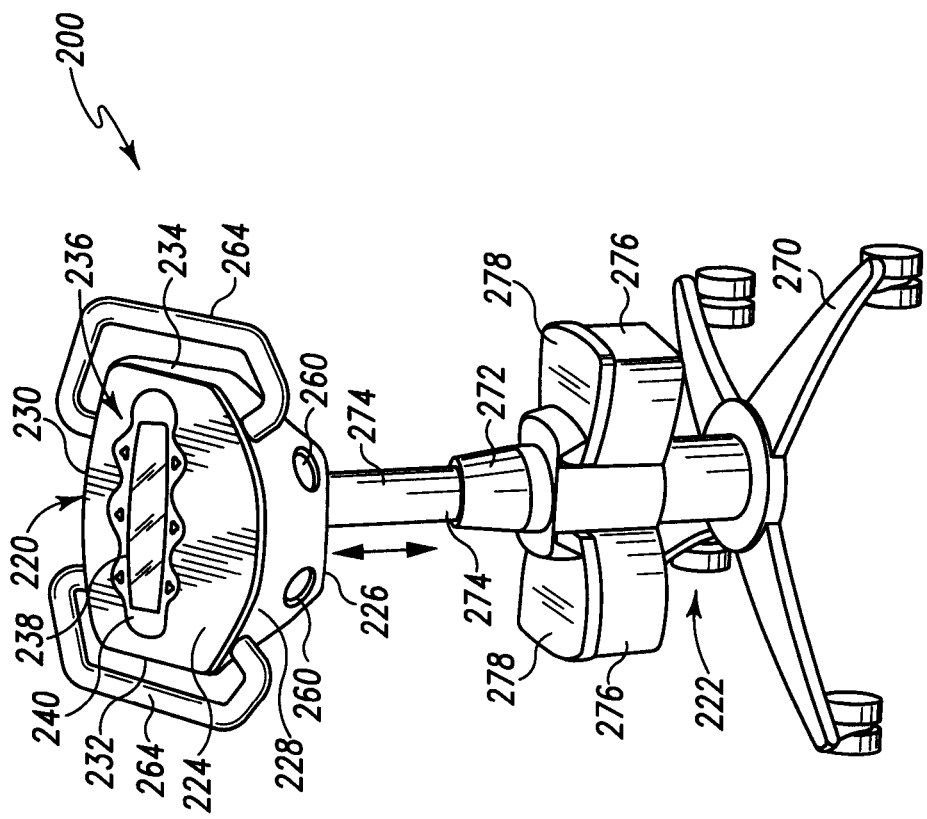
FIG. 6 is a perspective view, similar to FIG. 5, showing the housing raised to a higher elevation by adjustment of the wheeled pedestal.
Figure 7:
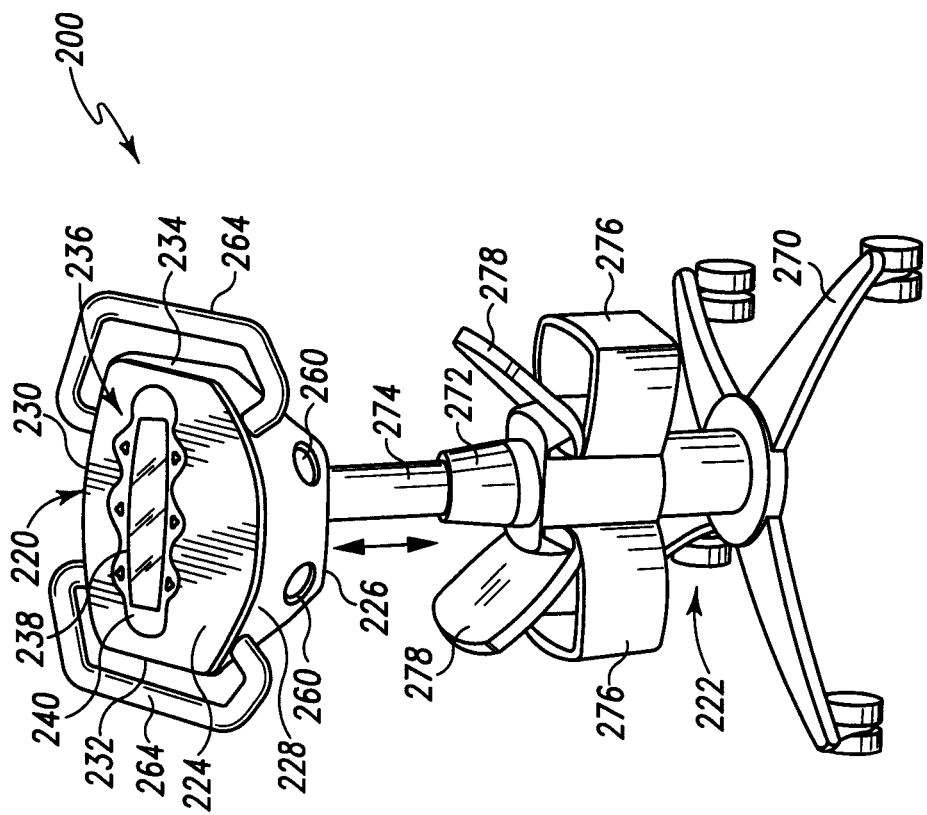
FIG. 7 is a perspective view, similar to FIG. 5, showing the lids moved to an opened position to provide access to the storage bins.

As shown in FIG. 4, the system 100 includes an air pulse generator 120 which is located in an interior region of the housing 110. The air pulse generator 120 is operable to produce the HFCWO air pulses. The air pulse generator 120 includes a self-oscillating valve 122 coupled via a hose 126 to a source of pressurized air, such as a hospital pressurized air system which includes one or more outlets 124 that are located in hospital rooms to provide connection points to the pressurized air system. The hose 126 is also coupled to a port 128 of the housing 110. Illustratively, port 128 is provided on the bottom of housing 110, but may be provided on some other part of housing 110, such as the back, front, top, or one of the sides of the housing 110, if desired. The air pulse generator 120 includes an air amplifier 130 coupled to the self-oscillating valve 122 and coupled to the bladder 114 of the vest 106 via a pair of hoses 118. In other embodiments, system 100 may have only a single hose 118 or may have more than two hoses 118, if desired. Various hose segments or other conduits that extend from housing 110 to vest 106 are considered to be a "hose" according to this disclosure.

The self-oscillating valve 122 is driven by pressurized air from the pressurized air outlet 124 to produce oscillating pressure comprising first pressure pulses having a first pressure and a first volume flow rate for application to the air amplifier 130. The air amplifier 130 converts the first pressure pulses into oscillating pressure comprising second pressure pulses that are communicated to the bladder 114. The second pressure pulses have a second pressure that is smaller than the first pressure and have a second volume flow rate that is greater than the first volume flow rate.

Figure 2:
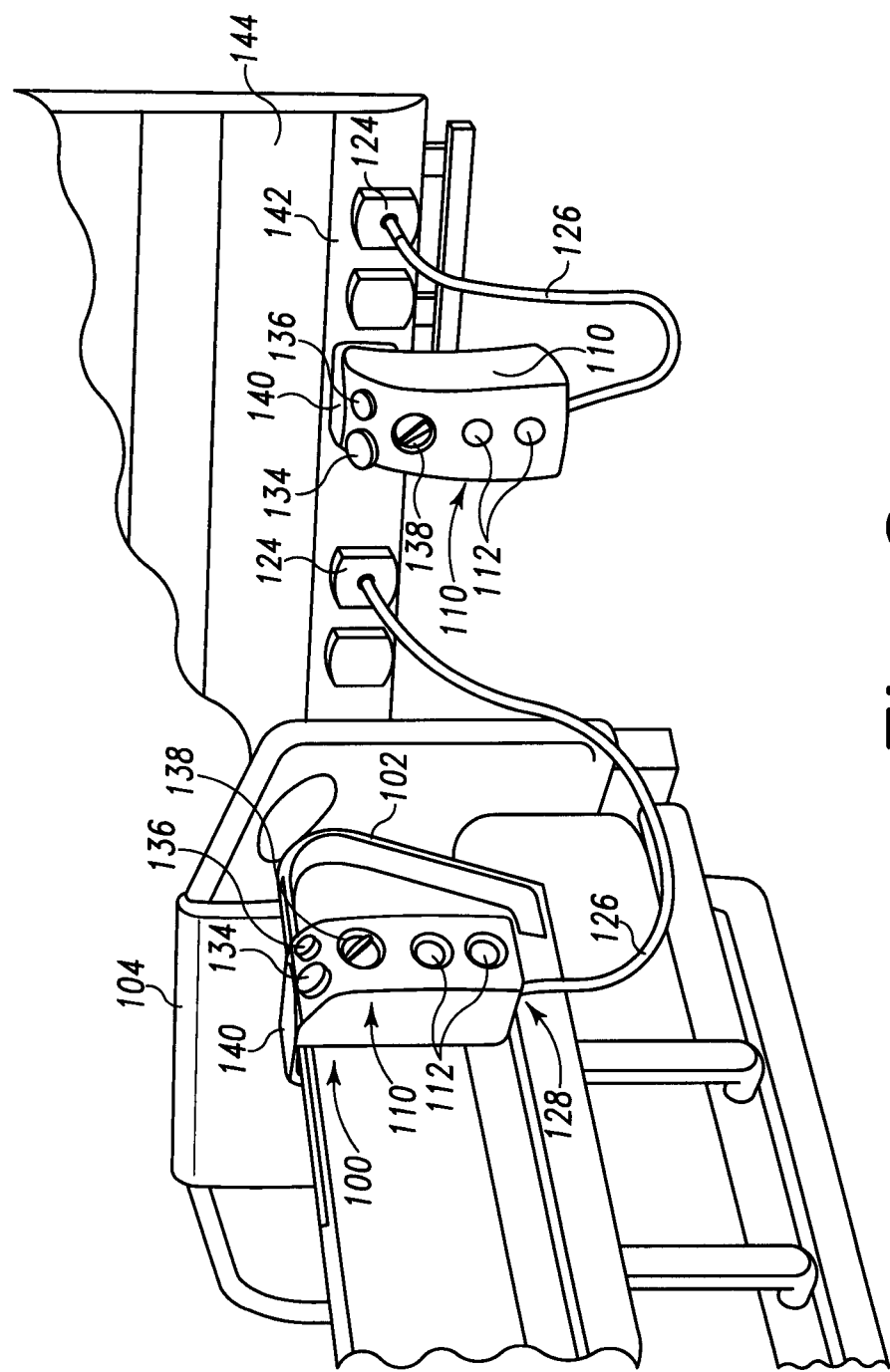
FIG. 2 is a perspective view showing two HFCWO therapy systems, one supported on a siderail of a hospital bed and one supported on an accessory rail of a headwall of a patient room.
Figure 3:
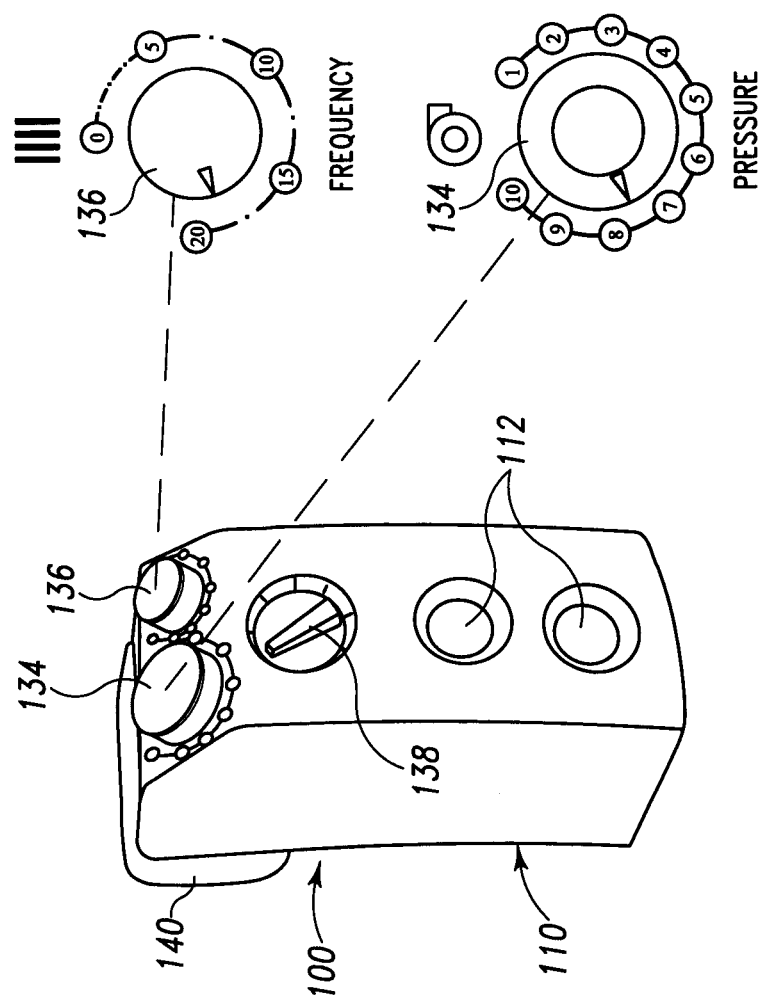
FIG. 3 is an enlarged perspective view showing the controls of the HFCWO therapy system of FIG. 1.

The self-oscillating valve 122 includes a pair of proportioning valves 132, shown diagrammatically in FIG. 4, which are coupled to a pressure control 134 and a frequency control 136 which are mounted on the housing 110 as shown in FIGS. 1-3. The pressure control 134 is operable to vary a base line pressure or steady state pressure about which the air pulses oscillate and the frequency control 136 is operable to vary the frequency of the air pulses. In the illustrative system 100, controls 134, 136 comprise knobs that are rotated or turned to adjust the amount by which the respective valves 132 are opened or closed. In the diagrammatic view of FIG. 4, hose 124 splits into two segments that couple to respective valves 132. In other embodiments, hose 126 couples to an inlet of a manifold that provides flow paths from the inlet to two outlets which are, in turn, coupled to the valves 132 of valve 122. In still other embodiments, hose 126 may couple to valve 122 and valve 122 may include flow passages that direct air from hose 126 to valves 132.

Valve 122 further includes a valve member 131, shown diagrammatically in FIG. 4, which moves back and forth within a valve chamber at a frequency dictated by the position of control 136. The base line pressure or steady state pressure of the oscillating pressure which is communicated through the valve chamber to air amplifier 130 is dictated by the position of control 134 as mentioned above. Valve 122 includes a valve body 133 which defines the valve chamber in which valve member 131 reciprocates. The valve body 133 may comprise one or more pieces of material and typically will also have a set of flow channels through which pressurized air flows so as to cause the reciprocation of valve member 131. Some of the set of flow channels communicate with the valve chamber through respective ports. As valve 131 reciprocates within the valve chamber, various ones of the ports are blocked or opened depending upon the position of valve member 131 within the chamber. Valve 122 may also have cross-over valves and/or check valves or the like to control the flow of pressurized air through the various flow channels at different times during the reciprocation of valve member 131 within the valve chamber of valve body 133.

In one embodiment, the self-oscillating valve 122 is of the type supplied by J.W.F. Technologies as Numatics Model No. L23PP4520, and the air amplifier 130 is of the type marketed by Pelmar Engineering Ltd. as ITW Vortec Model No. 902. While the pressure of the pressurized air supplied to the self-oscillating valve 122 is dictated by the components and configuration of the medical gas system of the associated healthcare facility, pressures of such systems typically range from about 40 to about 100 p.s.i. (pounds per square inch) and the air that is supplied by such systems is usually at a relatively low flow rate, which flow rate is established, at least in part, by the internal components of the associated outlet 124. The pressure within bladder 114 of vest 106 during HFCWO therapy is typically on the order of about 0.1 p.s.i. (or even less) to about 1.2 p.s.i. (or even more) and the volume flow rate of air during HFCWO may be on the order of about 20 $in^3$ (or less) per cycle to about 30 $in^3$ (or more) per cycle. In one embodiment, the volume flow rate of air is about 29 $in^3$ per cycle. Thus, valve 122 and air amplifier 130 are chosen so as to reduce the incoming pressure from outlet 124 down to a suitable pressure range for HFCWO therapy and to increase the flow rate up to be a suitable volume flow rate range for HFCWO therapy. To achieve the desired results, therefore, embodiments of system 100 having series and/or parallel combinations of two or more air amplifiers 130 are within the scope of this disclosure, as are embodiments having one or more pressure regulators situated in the flow path between hose 124 and valve 122 and/or situated in the flow path between valve 122 and air amplifier 130 (or amplifiers 130 if more than one are provided).

In the illustrated embodiment, the frequency of the air pulses applied to the bladder 114 of vest 106 is adjustable to be from about 0 Hertz (Hz) to about 20 Hz as indicated by the indicia adjacent to control 136 shown in FIG. 3. For typical HFCWO therapy, the operational frequency of system 100 is 5 Hz or higher, which is a much higher frequency than the frequency typically used for cardio pulmonary resuscitation (CPR). The indicia adjacent to control 134, as shown in FIG. 3, include numerals 1 through 10, which numbers are relative settings corresponding generally to the amount by which the valve 132 associated with control 134 is opened, with a setting of 10 corresponding to fully opened.

The system 100 includes a timer control 138 mounted on the housing 110 to provide an alarm signal to indicate that a therapy time selected by a patient or caregiver has ended. In the illustrative embodiment, timer control 138 comprises a knob that is turned by a desired amount to set a mechanical timer that is carried by housing 110 and that is coupled to control 138. Illustratively, the system 100 uses a rotary spring wound timer. Thus, the timer controlled by control 138 may be a so-called "egg timer." The mechanical timer produces an audible alarm, such as ringing a bell or chime included in the timer, when the therapy time has elapsed.

A hanger 140 is coupled to housing 110 and is configured to suspend the housing 110 from any suitable support device, such as the siderail 102 of the hospital bed 104. Alternatively, the housing 110 may be supported by an accessory mounting rail 142 of a headwall 144 in a patient room 146 of a hospital as shown with respect to the system 100 shown on the right side in FIG. 2. In the illustrative example, hanger 140 is a solid piece of material that extends rearwardly from the top of housing 110 and forms a hook that is configured to catch on the siderail or headwall rail or other similar support structure. In other embodiments, hanger 140 may extend from the back of housing 110 at some other location, such as, for example, midway between the top and bottom of housing 110.

If desired, hanger 140 may be formed integrally with other portions of housing 110, such as the top or back of housing 110, rather than being a separate component that couples to housing 110. It is within the scope of this disclosure for system 100 to have some other types of hangers for supporting housing 110 relative to a support device. For example, other hangers may comprise clamps or straps. Furthermore, it is within the scope of this disclosure for some or all of hanger 140 to move between a storage position, such as a position retracted into or adjacent housing 110 or even a position folded against housing 110, and a use position in which hanger 140 is deployed for use. The housing 110 and the hanger 140 are both made of high-strength, light weight plastic in the illustrated embodiment but may be made from any materials having suitable strength.

In operation, system 100 produces a pressure having a steady state air pressure component (or "bias line pressure") and an oscillating air pressure component. The air pulses oscillate the bladder 114, while keeping it inflated. The bladder 114 applies an oscillating compressive force to the chest of the patient 108. The oscillating compressive force applied to the chest has an oscillatory force component and a steady state force component which respectively correspond to the oscillating air pressure component and the steady state air pressure component. Illustratively, the steady state air pressure component is greater than the atmospheric pressure with the oscillatory air pressure component riding on the steady state air pressure component. The term "steady state component" as used herein, including in the claims, is not intended to be limited only to an unchanging pressure having substantially no fluctuations, although such an unchanging pressure would be an example of a steady state component of the pressure. Due to many factors, including the fact that a high frequency oscillatory pressure is superimposed on the so-called "steady state component," the "steady state component," itself, may fluctuate by some amount but yet still be considered a "stead state component" within the scope of this disclosure.

In the illustrated embodiment, the resulting composite waveform provides oscillation cycles of the bladder 114 that are effective at moving the chest of the patient 108, because at no point in the cycles is the pressure applied to the chest by bladder 114 below atmospheric pressure. It should also be understood that vest 106 has an established leakage rate to permit pressurized air to exhaust from vest 106 to the ambient atmosphere. Depending upon the design of vest 106, such leakage may occur through holes created by stitching between layers of material that define bladder 114, through holes created by stitching between a single layer and an enclosure that defines bladder 114, through discrete holes formed in one or more layers of vest 106, or through a loose weave of material forming a part of vest 106. Due to the fact that system 100 has moving components (such as the shuttling valve member 131 in the self-oscillating valve 122) and due to the fact that the leakage rate of pressurized air from vest 106 may not be constant (due to the fact, for example, that inhalation of the patient may tend to force air out of vest 106 more so than when the patient is inhaling), it will be appreciated, therefore, that these are additional factors that contribute to the steady state pressure or bias line pressure possibly not being a constant pressure but rather fluctuating within some range of pressures. However, such a fluctuating pressure is still considered to be a steady state pressure or a bias line pressure, according to this disclosure, including in the claims as already mentioned.

Based on the foregoing, it will be appreciated that system 100 is an all-pneumatic system without any electrical components, although the timer is a mechanical timer. The system 100 is couplable to outlet 124 and is operably driven by pressurized air from a pressurized gas system which communicates pressurized air to system 100 through the associated outlet 124 of a hospital or a healthcare facility. Therefore, system 100 does not include a blower or a motor-and-diaphragm assembly, nor does system 100 include the attendant electronic circuitry associated with such components, thereby reducing the cost of, the weight of, and the space occupied by, system 100 as compared to prior art HFCWO systems. The system 100 is so compact that the housing 110 of the system 100 can be supported on a siderail or an accessory mounting rail of a hospital bed as shown, for example, in FIGS. 1 and 2. For example, the width and the depth of the housing 110 may be on the order of about 3 inches to about 9 inches, and the height of the housing 110 be on the order of about 6 inches to about 12 inches. In other embodiments, housing 110 may have dimensions that are larger than, or smaller than, the above-listed dimensions.

FIGS. 5-11 illustrate a second embodiment 200 of a HFCWO therapy system according to this disclosure. As shown diagrammatically in FIG. 11, system 200 includes an air pulse generator 202 and a controller 204. The air pulse generator 202 comprises a blower 206 and an air chamber assembly 208. The blower 206 supplies pressurized air to assembly 208 and cooperates with assembly 208 to produce HFCWO air pulses that are communicated to a vest 210 of system 200. In some embodiments, the air chamber assembly 208 includes an air chamber shell (not shown) which receives pressurized air from the blower 206 and a pair of opposed diaphragm assemblies (not shown) which are reciprocated toward and away from one another by a motor and linkage assembly to produce air pulses for application to the vest 210. This type of air pulse generator is included in a HFCWO system marketed by Advanced Respiratory, Inc. of St. Paul, Minn. as the Model 104 system and is disclosed in U.S. patent application Ser. No. 10/295,782 which published as US Patent Application Publication No. US 2004/0097842 and which is hereby incorporated by reference herein. Thus, while system 100 is driven by pressurized air from the hospital pressurized air outlet 124, system 200 has an on-board blower 206 for supplying pressurized air.

System 200 includes a housing 220 supported on a wheeled pedestal 222 as shown in FIGS. 5-8. The housing 220 includes a top wall 224, a bottom wall 226, a front wall 228, a rear wall 230, and a pair of side walls 232, 234. The air pulse generator 202 and the controller 204 are located in an interior region of the housing 220. The front wall 228 has a pair of air ports 260. The air ports 260 are coupled to vest 210 by a pair of hoses 262 as shown diagrammatically in FIG. 11. A user interface 236 is coupled to the top wall 224 and is coupled to the controller 204. The user interface 236 is configured to allow a caregiver to control the operation of the air pulse generator 202. As shown best in FIGS. 9 and 10, the user interface 236 includes a display screen 238 and a keypad 240. The keypad 240 has the following buttons: on button 242, off button 244, upper left button 246, lower left button 248, upper middle button 250, lower middle button 252, upper right button 254, and lower right button 256. The keypad 240 surrounds the display screen 238. Display screen 238 is a liquid crystal display (LCD) screen in some embodiments, although interface 236 may have any suitable type of electronic display screen according to this disclosure. In some embodiments, display screen 238 is a touch screen which includes appropriate areas thereon corresponding to one or more of buttons 242, 244, 246, 248, 250, 252, 254, 256.

In the illustrative embodiment, the on button 242 is located on the left side of display screen 238 and the off button 244 is located on the right side of display screen 238. The buttons 246, 250 and 254 are located above and adjacent to the top of display screen 238 and the buttons 248, 252 and 256 are located below and adjacent to the bottom of display screen 238. The caregiver may modify the operation of air pulse generator 202 by using the buttons 246, 248, 250, 252, 254, 256. The function of the buttons 246, 248, 250, 252, 254, 256 varies depending on the current state or mode of the air pulse generator 202. In some embodiments, air pulse generator 202 is operable in any of the modes described in U.S. patent application Ser. No. 10/295,782 which published as US Patent Application Publication No. US 2004/0097842 and which is already incorporated by reference herein. Such modes include, for example, a manual mode, a step program mode, a sweep program mode, a training mode, and a custom program mode.

Figure 9:
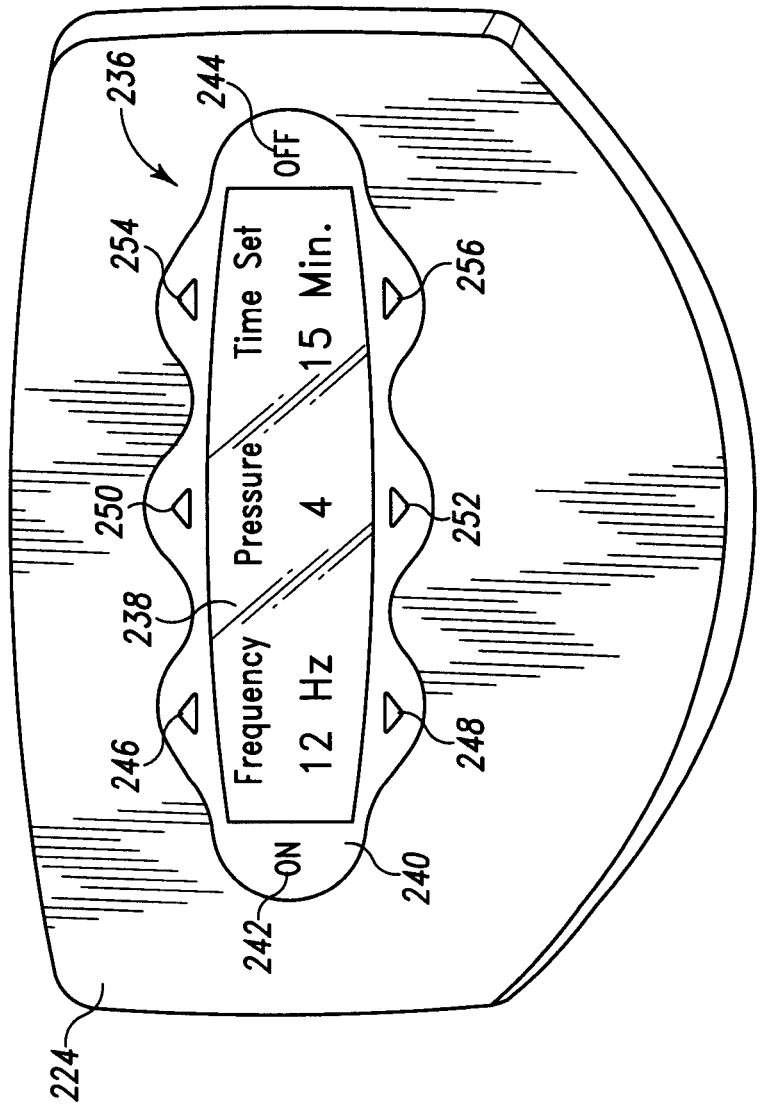
FIG. 9 is a screen shot of the display screen showing a manual program mode of the HFCWO therapy system.

Exemplary information which appears on display screen 238 in the manual mode is shown in FIG. 9. In particular, display screen 238 shows two lines of information. The upper line of information includes the words "Frequency," "Pressure," and "Time Set." The lower line of information shows the current settings for the corresponding parameter. In the illustrative example, the frequency of system 200 is set for 12 Hz, the pressure setting is 4, and the therapy duration is set for 15 minutes. As was the case with system 100, the pressure number shown on display screen 238 in the manual mode is a relative number (e.g., an integer between 0 and 10) and not the actual steady state pressure. In other embodiments, the pressure number shown on display screen 238 may be the steady state pressure setting (e.g., 0.1 p.s.i. to 1.2 p.s.i.). The two-line display of information on display screen 238 enables system 200 to provide more information to a user or caregiver than the one-line display screen included in the prior art Model 104 system mentioned above.

Figure 8:
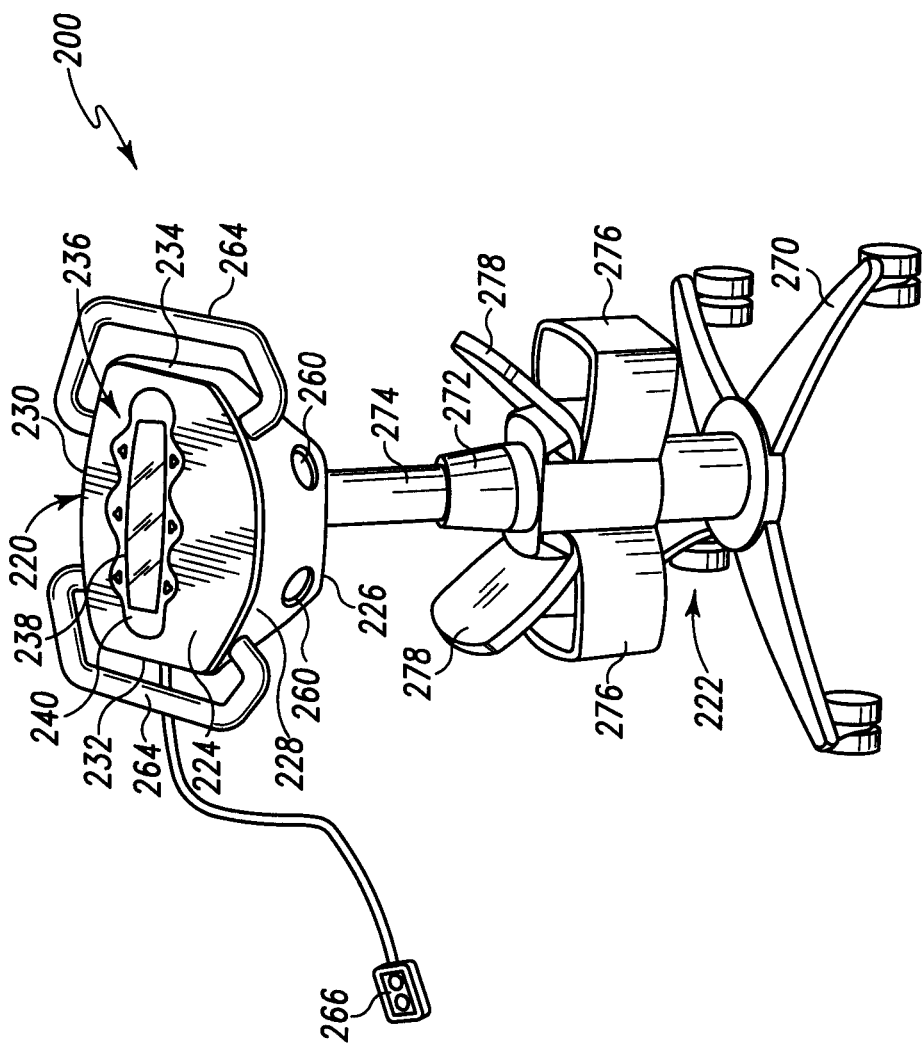
FIG. 8 is a perspective view, similar to FIG. 5, showing a remote on/off switch coupled to the HFCWO therapy system.

In the manual mode, buttons 246, 248 may be pressed by a user or caregiver to increase and decrease, respectively, the frequency setting of system 200; buttons 250, 252 may be pressed by a user or caregiver to increase and decrease, respectively, the pressure setting of system 200; and buttons 254, 256 may be pressed by a user or caregiver to increase and decrease, respectively, the time setting of system 200. Once the manual mode parameters are set, the user or caregiver initiates the HFCWO therapy according to the parameters by pressing the on button 242. If the user or caregiver wants to stop the therapy, the user or caregiver does so by pressing the off button 244. If the user or caregiver pressure off button 244 when no HFCWO therapy is occurring, then system 200 powers down. If system 200 is powered down, then the user or caregiver presses the on button 242 to power up the system. In some embodiments, a remote on/off pendant 266 is coupled to the controller 204 by an extension cord 268, as shown in FIG. 8, and includes on and off buttons which may be used in the same manner as just described regarding the manner in which on and off buttons 242, 244 are used. The on and off buttons of pendant 266 are color coded such that the on button is green and the off button is red.

Figure 10:
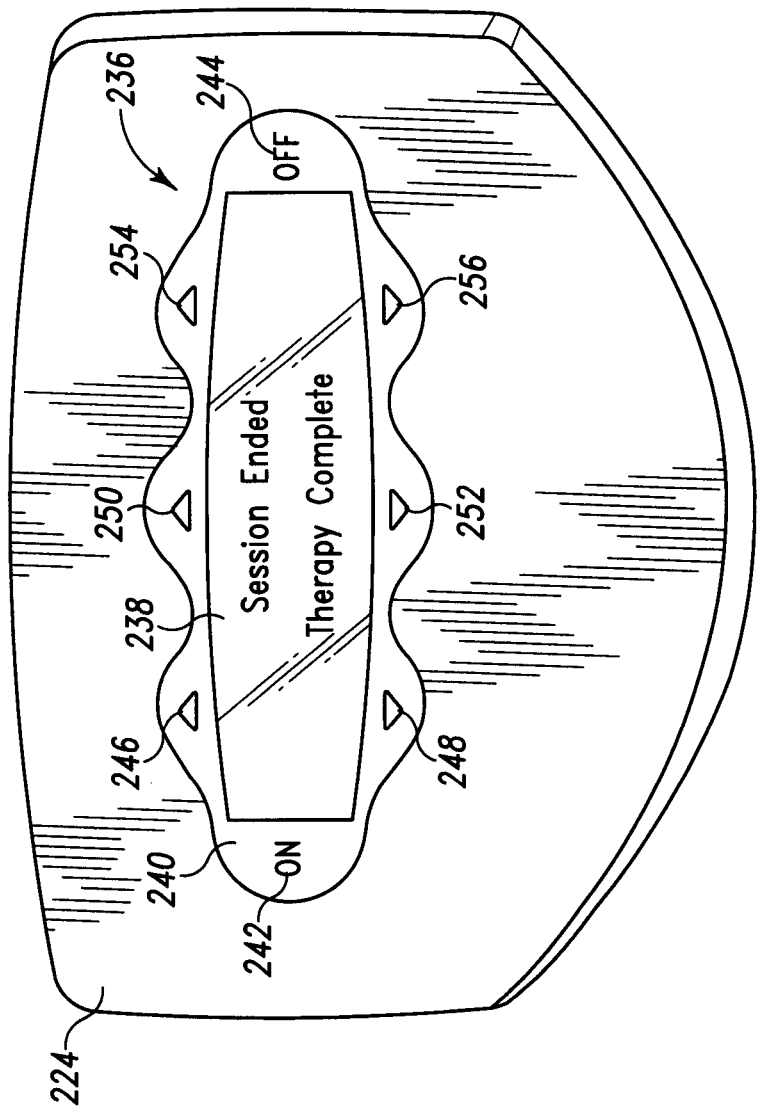
FIG. 10 is a screen shot of the display screen showing the status of the HFCWO therapy system.

The HFCWO therapy automatically stops when the time duration is complete, and a message such as "Session Ended, Therapy Complete" is displayed on the display panel 238 as shown in FIG. 10. The display panel 238 also provides feedback to the caregiver as to the status of system 200 when requested via appropriate presses of buttons 242, 244, 246, 248, 250, 252, 254, 256. For example, pressing two of buttons 242, 244, 246, 248, 250, 252, 254, 256 simultaneously may result in corresponding status information being displayed on screen 238 and the type of information displayed may vary depending which combination of two buttons 242, 244, 246, 248, 250, 252, 254, 256 are simultaneously pressed. The messages are displayed as text on the display panel 238. Also, the caregiver may use the buttons 246, 248, 250, 252, 254, 256 to program the air pulse generator 202. In the illustrated embodiment, in addition to the manual program mode, the caregiver can choose one of three pre-set program modes. The three pre-set program modes are stored as software in one or more memory devices included in controller 204.

In addition to display screen 238, buttons 242, 244, 246, 248, 250, 252, 254, 256, and one or more memory devices, controller 204 also includes all other electrical components associated with the operation of system 200. In one embodiment, controller 204 is substantially the same as that shown and described in U.S. patent application Ser. No. 10/295,782 which published as US Patent Application Publication No. US 2004/0097842 and which is already incorporated by reference herein. Two lines of up to 24 characters each are displayable on display screen 238.

As mentioned above, system 200 includes a housing 220 supported on a wheeled pedestal 222. A pair of generally C-shaped handles 264 are coupled to the housing 220 and are gripped by users or caregiver to maneuver system 200 along a floor. Each handle 264 has one end coupled to front wall 228 and another end coupled to rear wall 230. The handles 264 are coupled to walls 228, 230 of housing 220 closer to top wall 224 than to bottom wall 226. In addition, each of the handles extend around the sides of housing 220 with a central portion of each handle 264 being spaced from the respective side wall 232, 234 of housing 220.

The bottom wall 226 of the housing 220 is coupled to the pedestal 222 by a lockable swivel joint (not shown) which is unlockable to permit titling of housing 220 relative to pedestal 222 about a generally horizontal axis. This allows the caregiver to tilt the housing 220 to change the viewing angle of the display screen 238. The pedestal 222 is vertically extendable and retractable to support the housing 220 at selected elevations. The pedestal 222 includes a wheeled base 270, a stationary portion 272 coupled to wheeled base 270, and a telescoping portion 274 coupled to the stationary portion 272 and coupled to the bottom wall 226 of the housing 220 by the lockable swivel joint.

In the illustrative example, portions 272, 274 comprise cylindrical tubes with round cross sections, but tubes having other cross sections such as polygonal (e.g., square, rectangular, triangular, hexagonal, etc.) or oval or elliptical or any other desired shape are within the scope of this disclosure. The telescoping portion 274 is movable generally vertically relative to the stationary portion 272 between a lowered position shown in FIG. 5 and a raised position shown in FIGS. 6-8. In some embodiments, the telescoping portion 274 is pivotable about a generally vertical axis relative to the stationary portion 272. Additionally or alternatively, the lockable swivel joint may be constructed to permit housing 220 to pivot about a generally vertical axis relative to pedestal 222.

An elevation adjustment mechanism and/or locking mechanism (not shown), such as a locking gas spring, normally locks the telescoping portion 274 in place relative to the stationary portion 272 but is unlockable to permit telescoping movement of portion 274 relative to portion 272. In some embodiments, one or more release handles or levers are coupled to one or both handles 264 and are movable to release the locking mechanism. For example, if the locking mechanism is a locking gas spring, then a Bowden wire or cable (e.g., a sheath having a wire extending therethrough) may have one end coupled to the release lever and have another end coupled to a portion of the locking gas spring that is actuated or moved to release or unlock the locking gas spring. Such a Bowden wire may be routed from the release lever, through a portion of the corresponding handle 264, through housing 220, and through a portion of pedestal 222. Movement of the release lever, in such embodiments, causes the wire to move within the sheath and unlock the gas spring. The gas spring, when released, may be of the type that is biased to extend thereby providing an upward force that assists the user or caregiver in moving housing 220 upwardly.

In other embodiments of system 200, a release lever or handle is coupled to pedestal 222 beneath housing 220 and is movable to unlock and lock the elevation adjustment mechanism and/or locking mechanism. In still other embodiments, the elevation adjustment mechanism and/or locking mechanism may comprise a hydraulic cylinder or a pneumatic cylinder and a foot pedal (not shown) may be coupled to base 270 and movable to raise and lower the height of the pedestal 222. For example, a repetitive pumping action of such a foot pedal through a stroke length may result in hydraulic fluid being pumped into the hydraulic cylinder (or air being pumped into the pneumatic cylinder) to raise the pedestal 222 and depressing and holding the foot pedal in its lowest position may result in hydraulic fluid exiting the hydraulic cylinder (or air exiting the pneumatic cylinder) to lower the pedestal 222.

In further embodiments of system 200, a jack screw arrangement may be provided in pedestal 222 such that rotation of housing 220 and portion 274 in one direction about a generally vertical axis relative to portion 272 results in extension of portion 274 relative to portion 272, thereby to lift housing 220 relative to base 270, and rotation of housing 220 and portion 274 in an opposite direction relative to portion 272 about the generally vertical axis results in retraction of portion 274 relative to portion 274, thereby to lower housing 220 relative to base 270. In such embodiments having a jack screw arrangement as the elevation adjustment mechanism, a latch or retractable pin or the like may be provided to serve as a locking mechanism to prevent rotation of portion 274 relative to portion 272. Such a pin or latch may be coupled to portion 272 and may have a portion that enters a hole or recess provided in portion 274 to lock portion 272 from rotating relative to portion 274 and that is withdrawn from the hole or recess to permit rotation of portion 272 relative to portion 274.

In yet other embodiments, an electrically powered linear actuator may be provided as an elevation adjustment mechanism to raise and lower portion 274 relative to portion 272 thereby to raise and lower, respectively, housing 220 relative to base 270. Such a linear actuator may be powered by a battery carried within housing 220 or on base 270. Alternatively or additionally, such a linear actuator may be powered by electrical power received from a wall outlet when a power cord (not shown) of system 200 is plugged into the outlet. If system 200 has an on-board battery to power the linear actuator, the battery may be recharged when system 200 is plugged into a power outlet. In such embodiments, controller 204 includes battery recharging circuitry. In further embodiments, a hand cranking mechanism may be provided as an elevation adjustment mechanism to extend and retract portion 274 relative to portion 272 thereby to raise and lower, respectively, housing 220 relative to base 270. Such a hand cranking mechanism may include a hand crank coupled to portion 272, a worm gear arrangement coupled to the hand crank, and a rack-and-pinion arrangement coupled to the worm gear arrangement and coupled to portion 274. One of the gears of the worm gear arrangement may be the pinion of the rack-and-pinion arrangement, with the rack being coupled to portion 274 to raise and lower therewith as the hand crank turns a worm of the worm gear arrangement which meshes with the pinion.

A pair of storage bins 276 are coupled to the stationary portion 272 of pedestal 22 on opposite sides thereof. A lid 278 is coupled to each bin 276 by a suitable hinge mechanism, such as a living hinge, one or more flexible straps, one or more pivot pins, or the like. Each lid 278 is movable relative to the associated bin 276 between a closed position blocking access to a storage compartment of the respective bin 276 and an opened position allowing access to the storage compartment through an open top of the associated bin 276. In the illustrated embodiment, the lids 278 are opaque and bins 276 are semi-transparent or substantially transparent. In some embodiments, the lids 278 are semi-transparent or substantially transparent. The storage compartments of bins 276 provide spaces for receipt of other parts of system 200 such as garments (such as vests or wraps), hoses, mouthpieces, masks, sputum bowls, electrical cords, and equipment for other respiratory therapies, such as a positive expiratory pressure (PEP) therapy, a nebulizer therapy, an intermittent positive pressure breathing (IPPB) therapy, a cough assist therapy and/or other types of a suction therapy such as negative wound pressure therapy, a bronchial dilator therapy, and the like. While the illustrative system 200 has two bins 276 coupled to pedestal 222, systems having more or less than two bins 276, including systems having no bins at all, are within the scope of this disclosure.

The whereabouts of system 200 in a healthcare facility may be tracked by a locating-and-tracking system. Thus, a locating-and-tracking badge may be coupled to the exterior of housing 220 or pedestal 222. Such a locating-and-tracking badge includes a transmitter to transmit a wireless signal, either periodically or in response to receipt by a receiver of the badge of a wireless query signal. The wireless signal transmitted by the badge is received by one or more receivers located throughout the healthcare facility. The transmitter and receiver of the locating-and-tracking badge may be combined as a transceiver in some embodiments and may be separate in other embodiments. The wireless signals includes a unique ID which is associated with system 200.

In other embodiments, the circuitry of system 200 includes a transmitter and/or receiver and/or transceiver to transmit ID data to other portions of the locating-and-tracking system, either periodically or in response to a query signal. In such embodiments, therefore, a locating-and-tracking badge does not need to be coupled to the housing 220 or pedestal 222. Also in such embodiments, the ID data transmitted by the circuitry of system 200 may be programmable via appropriate presses of buttons 242, 244, 246, 248, 250, 252, 254, 256 to place system 200 into an ID programming mode in which the ID data to be transmitted can be programmed. In addition to the ID data, system 200 may transmit data indicative of whether or not system 200 is currently in use and optionally, may also transmit data indicative of the amount time left before the current HFCWO therapy session will end. Thus, a caregiver viewing a remote display screen of a computer of the locating-and-tracking system can receive information regarding the whereabouts of a particular system 200 in the healthcare facility. If the information on the display screen of the computer of the locating-and-tracking system indicates that the system 200 is in use and will remain in use for some period of time, such as 30 minutes for example, then the caregiver can avoid retrieving the system 200 for use by another patient until the use by the current patient has finished.

Figure 12:
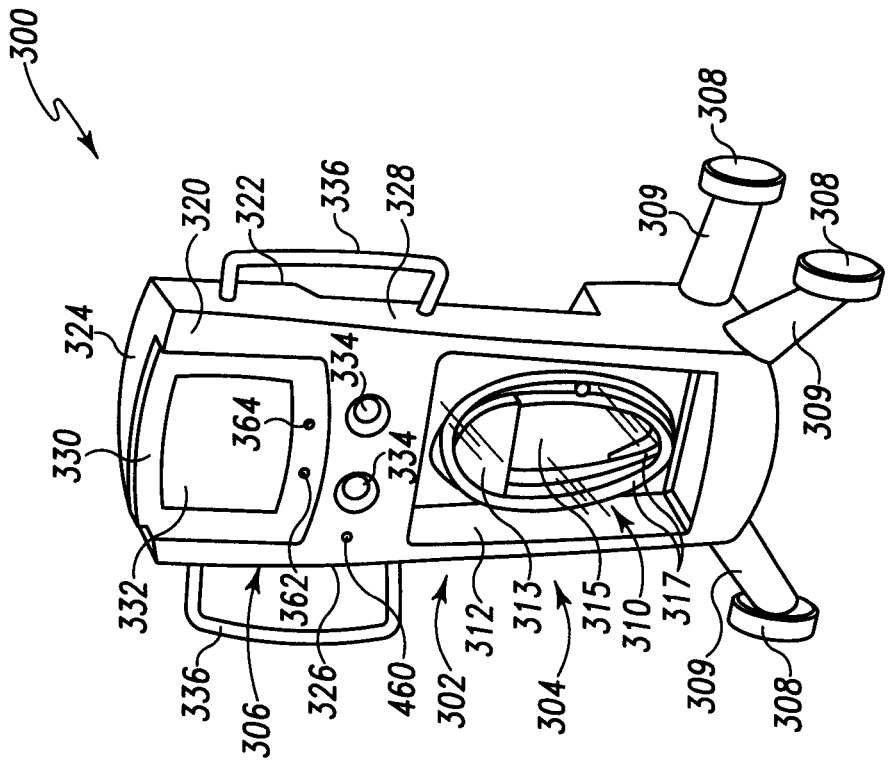
FIG. 12 is a perspective view of a third embodiment of a HFCWO therapy system showing a housing supported on a rolling stand, the housing having a vertically-adjustable large display, a pair of handles, a lower storage compartment, two large air ports through which air pulses are routed from the HFCWO therapy system to a garment, and a small port through which pressurized air is supplied to a respiratory therapy device, such as a nebulizer.

FIGS. 12-23 show a third embodiment 300 of a HFCWO therapy system according to this disclosure. System 300 includes a generally box-shaped housing 302 having a lower portion 304 and an upper portion 306 as shown in FIG. 12. The lower portion 304 is supported on wheels 308 that are rotatably coupled to respective arms 309 that extend outwardly and slightly downwardly from the sides of lower portion 304 of housing 302. The front arms 309 also extend slightly forwardly from the side of housing 302 and the rear arms 309 extend slightly rearwardly from the side of housing 302. In some embodiments, the front wheels 308 and/or the rear wheels 308 are able to swivel about generally vertical axes to facilitate turning of system 300 as it is transported along a floor.

The depth from front-to-rear of a lower part of lower portion 304 is larger than the depth of an upper part of lower portion 304 and the depth of upper portion 306 of housing 302. However, the width from side to side of housing 302 is generally uniform along the height of housing 302. Thus, housing 302 is an upright, generally rectangular structure when viewed from the front. Many of the heavier internal components of system 300, such as motors, diaphragm assemblies, compressors, and other hardware (described in more detail below) are situated in the lower part of portion 304 so that system 300 has a relatively low center of gravity which enhances the stability of system 300 and reduces the tendency of system 300 to tip. The wide wheelbase created due to the fact that arms 309 support wheels 308 laterally out to the sides of housing 302 and also slightly forwardly of, and slightly rearwardly of, housing 302 also enhances the stability of system 300.

The lower portion 304 of housing 302 includes a storage compartment 310 situated behind a door 312 which is coupled to housing 302 by a suitable hinge mechanism and which is movable between a closed position blocking access to compartment 310 and an opened position allowing access to compartment 310. In the illustrated embodiment, the door 312 is substantially transparent. In some embodiments, the doors 312 are opaque or are semi-transparent. A hook-like cantilevered structure 313 protrudes into compartment 310 from a generally vertical wall 315 which defines the back of compartment 310. Structure 313 supports hoses 317 in a looped or coiled configuration as shown in FIGS. 12-15. A vertical front plate of structure 313 retains hoses 317 on a portion of structure 313 on which the coiled hoses 317 hang to prevent hoses 317 from falling off of structure 313. If desired, other equipment or accessories, such as garments of system 300 may be stored in compartment 310.

Figure 13:
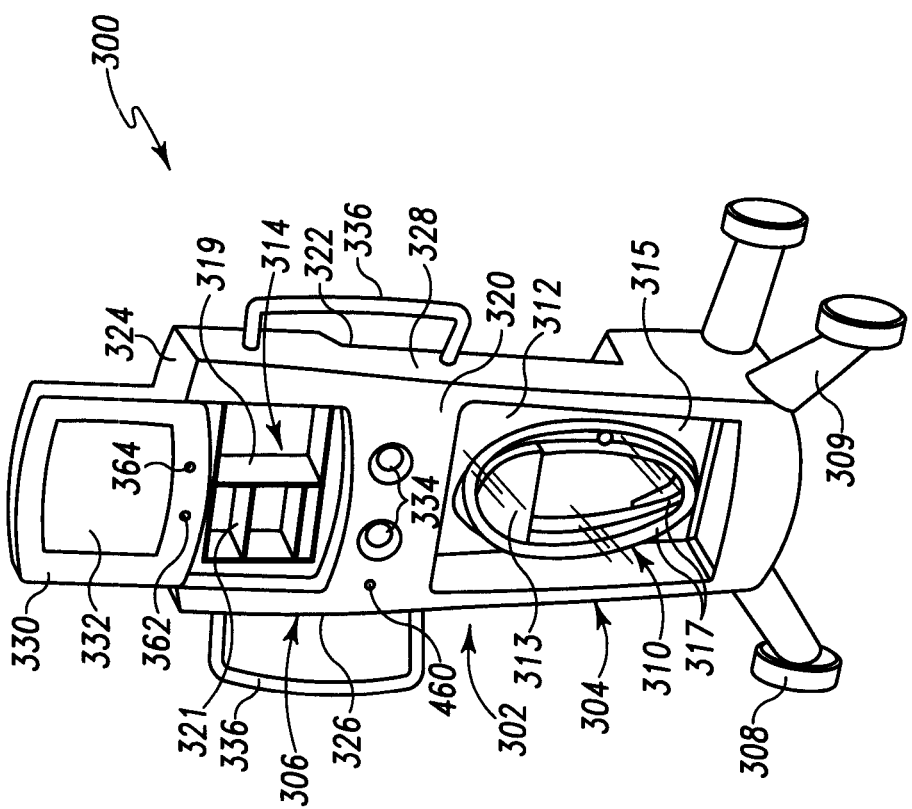
FIG. 13 is a perspective view, similar to FIG. 12, showing the display raised to a higher position in which an upper storage compartment is accessible.
Figure 14:
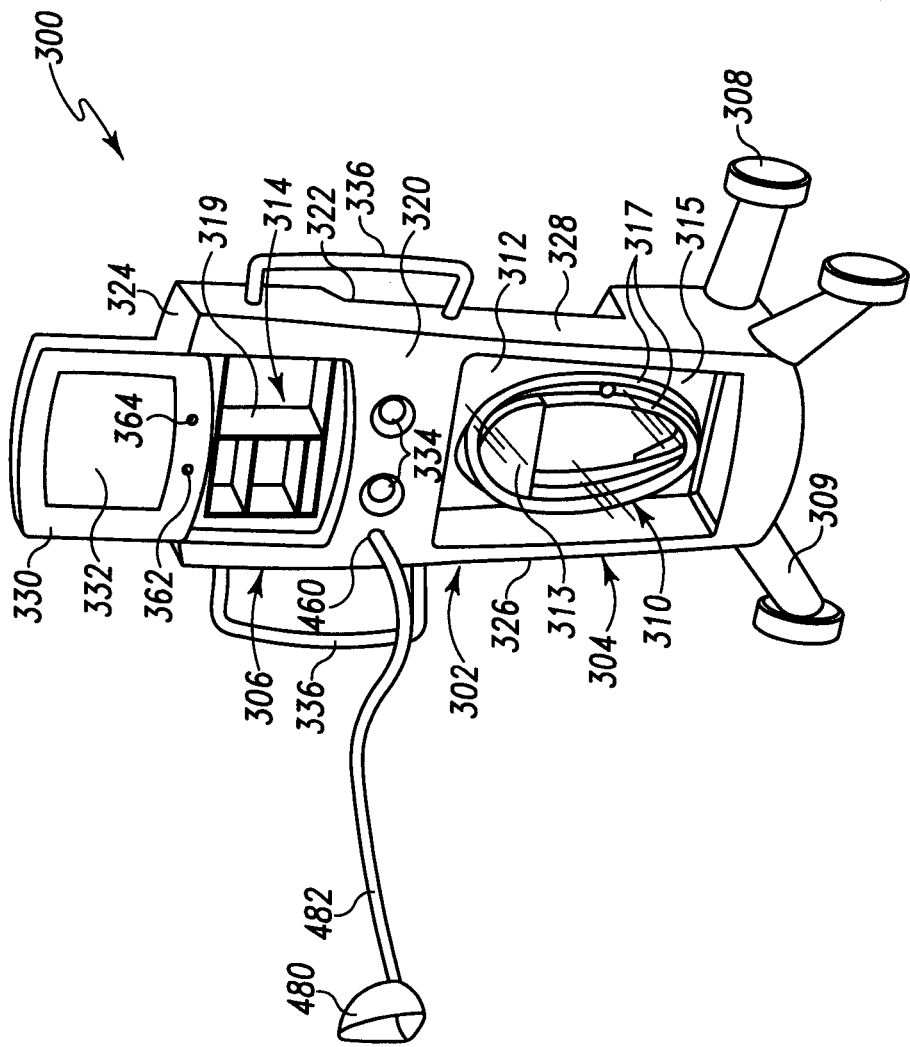
FIG. 14 is a perspective view, similar to FIG. 13, showing a hose coupled to a pressurized air port in the housing and a mask at the end of the hose.
Figure 15:
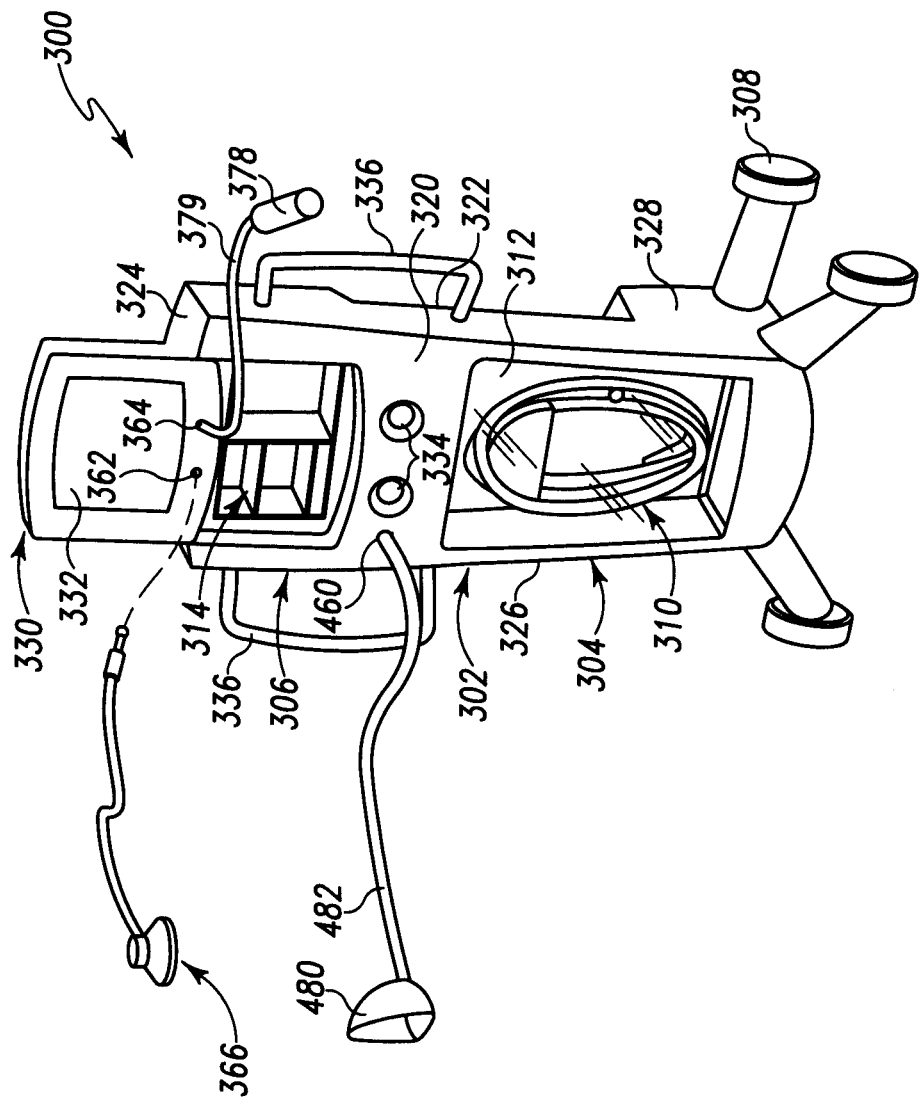
FIG. 15 is a perspective view, similar to FIG. 14, showing an electronic stethoscope coupled to an input port of the system of FIG. 12.

As shown in FIGS. 13-15, the upper portion 306 of housing 302 includes a storage compartment 314. In the illustrative embodiment, a vertical partition 319 and a horizontal shelf 321 are provided within compartment 314 to subdivide compartment 314 into multiple storage spaces. Similar partitions and shelves may be provided in space 310, if desired. In other embodiments, partition 319 and shelf 321 are omitted and compartment 321 comprises a single storage space. Compartments 310, 314 allow vests, hoses, mouthpieces, masks, sputum bowls, electrical cords, and other equipment associated with HFCWO therapy devices and/or additional respiratory therapy devices and/or assessment systems included in system 300, as well as any other desired equipment or objects, to be stored in housing 302 and transported from place to place along with system 300.

Figure 11:
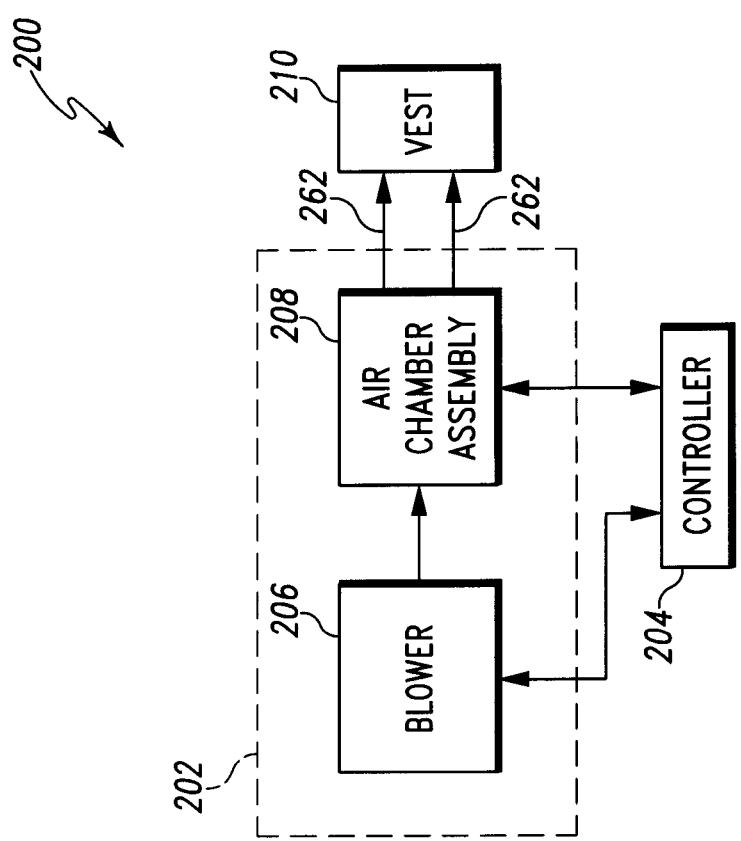
FIG. 11 is a block diagram of the HFCWO therapy system of FIGS. 5-10.
Figure 19:
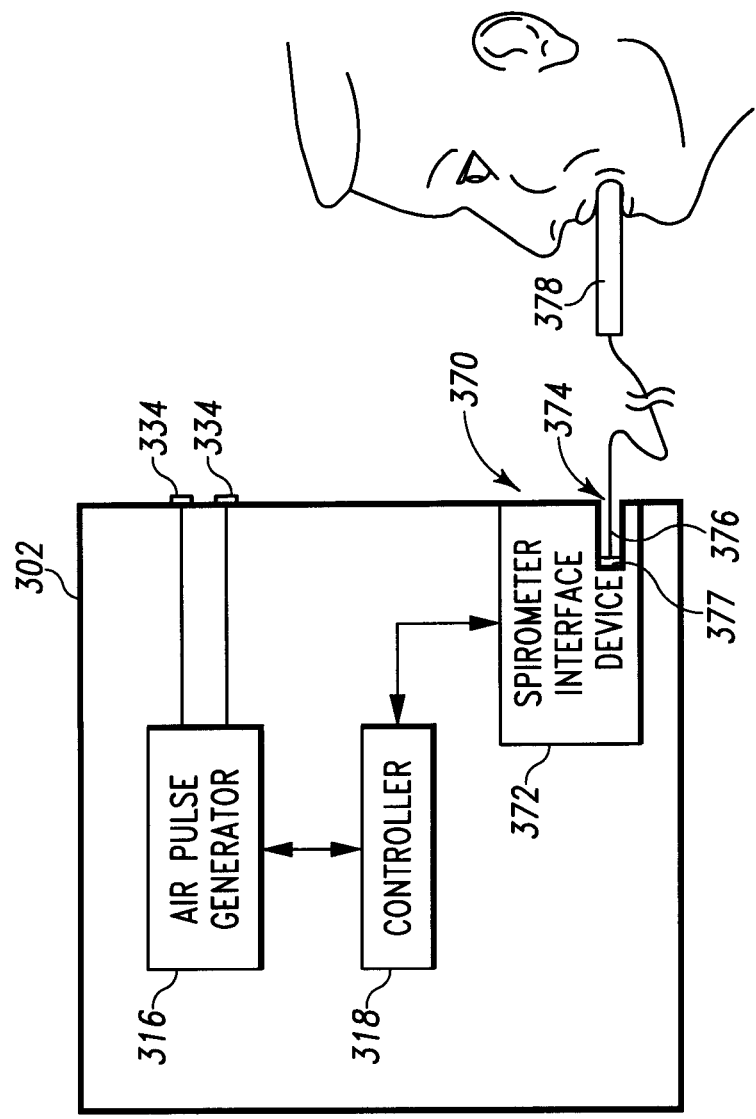
FIG. 19 is a block diagram showing an electronic spirometer coupled to the system of FIG. 12.

As shown diagrammatically in FIG. 19, system 300 includes an air pulse generator 316 comprising a blower (not shown) and an air chamber assembly (not shown), similar to the air pulse generator 202 shown in FIG. 11. In addition, the system 300 includes a controller 318 similar to the controller 204 shown in FIG. 11, except that the controller 318 has more features and capabilities as explained in more detail below. The air pulse generator 316 and the controller 318 are located within the housing 302. As alluded to above, air pulse generator 316 is situated in the lower part of lower portion 304 of housing 302 in the illustrative embodiment. Controller 318 comprises one or more circuit boards and the associated circuitry which may be located anywhere within housing 302 at the option of the system designer, although it may be desirable to have the heavier circuit components, such as power transformers and the like, located in the lower part of portion 304 along with the heavier hardware components. It may also be desirable for any circuit components that are more sensitive to heating to be situated on a circuit board that is located in upper portion 306 of housing 302 away from the motors and motorized components situated in lower portion 304. In some embodiments, system 300 has an on-board battery which is housed within, or carried by, the lower part of portion 304.

System 300 includes components operable to provide HFCWO therapy to a patient and also includes components operable to provide additional respiratory therapies to a patient and/or components for assessing of the various therapy systems of system 300. Examples of additional respiratory therapies for which the associated components may be included as part of system 300 include a cough assist therapy (FIG. 14), a nebulizer therapy (FIGS. 21 and 22), a suction therapy, such as cough assist therapy, (FIG. 23), a positive expiratory pressure (PEP) therapy, an intermittent positive pressure breathing (IPPB) therapy, and a bronchial dilator therapy. Examples of components of assessment systems which may be included as part of system 300 include a flow meter, an electronic stethoscope 366 (FIG. 15), a spirometer 370 (FIGS. 19 and 20), a tympanic thermometer to measure a patient's temperature via insertion into a patient's ear, a pulse oximeter to measure the patients blood oxygenation, and a respiration rate monitor to measure the patients respiration rate. If included, the assessment system of system 300 may be operable to determine the efficacy of, and/or to provide data for determining the efficacy of, at least one of the respiratory therapy systems and/or the HFCWO therapy system of system 300. The equipment and devices used for these additional therapies and the assessment systems may be stored in the storage compartments 310, 314, if desired.

As shown in FIGS. 12-15, the upper portion 306 includes a front wall 320, a rear wall 322, a top wall 324, and a pair of side walls 326, 328. A user interface, such as a video monitor or display 330, is coupled to the front wall 324 for vertical movement between a lowered position shown in FIG. 12 in which the monitor 330 blocks access to the upper storage compartment 314 and a raised position shown in FIGS. 13-15 in which the upper storage compartment is accessible. The height of the monitor 330 relative to housing 302 is adjustable to suit the caregiver's convenience. In the illustrated embodiment, the monitor 330 includes a touch screen display panel 332. Controller 318 is coupled to monitor 330 and is operable to cause various screens and various data to appear on the electronic display screen of display 330 as will be described in further detail below. The monitor 330 allows the caregiver to control the operation of the air pulse generator 316 and the operation of any of the additional respiratory therapy system(s) and/or assessment system(s) included in system 300.

The front wall 320 has a pair of air ports 334 which are configured to be coupled to a HFCWO therapy vest via hoses 317. Above air ports 334 is a recess in housing 302 that accommodates display 330 therein for vertical upward and downward movement. The recess in housing 302 and display 330 are sized such that a front surface of display 330 is generally coplanar with front wall 320 of housing 302. Display 330 comprises a flat screen display, such a liquid crystal display (LCD), of relatively narrow depth. The depth of display may be on the order of about 1 inch (2.54 cm) or less to about 3 inches (7.62 cm) or more. The recess in housing 302 to accommodate display 330, therefore, has a depth that is substantially smaller than the depth of storage compartment 314 as shown in FIGS. 13-15. The depth or the storage compartment may be on the order of two times or three times or four times or even more than the depth of the recess in which display 330 is received. The display 330 includes an electronic display screen 332, such as an LCD screen, a housing which carries the electronic display screen 332, and the associated electrical components situated in the housing.

The interface between the sides of display 330 and housing 302 may include suitable guide mechanisms to guide the upward and downward movement of display 330. For example, each of the sides of display 330 may be formed with a vertically oriented rail or tongue which is received in a respective vertically oriented groove formed in housing 302. Such a rail and groove arrangement may be reversed such that the sides of the display 330 are formed with grooves and the housing 302 is formed with tongues or rails that are received in the grooves of the display 330. In addition, separate members having the rails or tongues and the grooves may be coupled to housing 302 and display 330 in lieu of these guide structures being formed in the sides of display 330 and the housing 302. In other embodiments, a guide mechanism may include one or more vertical posts or struts extending downwardly from the bottom of display 330 into a respective vertically oriented socket provided in housing 302 beneath display 330. Such a vertically oriented socket may be situated, in part, between ports 334 or outboard of ports 334. The vertical partition 319 in such an embodiment may be located so as to be situated behind the vertically oriented post when display 330 is raised so as to reduce the amount by which the vertically oriented post may block or interfere with access to the usable space of storage compartment 314.

In some embodiments, display 330 and/or housing 302 and/or the guide mechanism itself may have suitable locking mechanisms to lock display 330 in place at selected elevations relative to housing 330. Such a locking mechanism may comprise, for example, one or more pins or latches carried by display which are received in apertures or recesses in housing 302, or vice versa. The apertures or recesses may be vertically spaced to define a set of vertical positions in which display 330 may be locked by receipt of the pins or latches in the associated apertures or recesses. Such pins or latches may be spring biased outwardly relative to display 330 toward housing 302 and into the apertures or recesses aligned therewith. A release mechanism, such as a lever, knob, or handle may be provided on display 330 in such embodiments for retracting the pins or latches out of the apertures or recesses to unlock the display 330 for movement relative to housing 302. If the pins or latches are coupled to housing 302 and if the display 330 has the apertures or recesses, then the release mechanism may be coupled to housing 302.

In embodiments having one or more vertically oriented guide posts, a spring clutch mechanism, such as Mechlok® mechanism available from Porter Group, LLC of Novi, Mich., may be situated inside housing 302 and coupled to the vertical guide post. Such a spring clutch mechanism typically has a rod that is movable relative to a rod housing and a spring that constricts around the rod to prevent the rod from moving relative to the rod housing. A release mechanism, such as a lever, knob, or handle, may be provided either on display 330 or on housing 302 for manipulation to unlock the normally locked spring clutch mechanism by causing the spring to loosen about the rod allowing the rod to move relative to the rod housing. If the release mechanism is provided on the display, then a suitable linkage mechanism, such as Bowden wire, may be routed from the release mechanism, through the interior of display, and through a hollow interior of the vertical guide post. In some embodiments, therefore, one of the rod and the rod housing of a spring clutch mechanism is fastened to the vertically oriented guide post and the other of the rod and the rod housing is fastened to a portion of housing 302, such as an internal frame member of housing 302 or a flange extending from front wall 320 in the interior region of housing 320.

In still other embodiments, one of the sides of display 330 may have a suitable hinge mechanism defining a generally vertical axis about which display 330 pivots to open and close compartment 314. In further embodiments, the bottom of display 330 may have a suitable hinge mechanism defining a generally horizontal axis about which display pivots downwardly to open compartment 314. In such an embodiment in which display 330 pivots downwardly about a horizontal hinge axis, one or more suitable stops may be provided to prevent display from pivoting downwardly beyond a generally horizontal position in which a back of display 330 provides a work surface that caregivers may use for temporary placement of objects or for writing on charts, etc. Alternatively, the top of display 330 may have a suitable hinge mechanism defining a generally horizontal axis about which display pivots upwardly to open compartment 314. In these embodiments in which display 330 is hinged to housing 302, a lock, pin, or latch may be provide to retain display 330 in the closed position and a release lever, knob, or handle may be provided for moving the lock, pin or latch to a position allowing the display to pivot to its opened positions.

In still further embodiments, the top of panel 330 may be coupled to a backing panel by a suitable hinge mechanism for pivoting movement about a generally horizontal axis relative to the backing panel. In such an embodiment, the backing panel raises and lowers along with display 330 to open and close compartment 314. The backing panel is retained relative to housing 302 in such embodiments by any of the guide mechanisms described above, such as tongue (or rail) and groove arrangements or vertical guide posts. However, display 330 is permitted to tilt out of the recess of housing 302 so that the electronic display screen faces upwardly by some amount, such as 30 degrees or 45 degrees or even up to 90 degrees, to provide more ergonomic viewing and access to the electronic display screen of display 330 by a caregiver or patient standing in front of system 300. The hinge mechanism of this embodiment may have friction between components of the hinge mechanism that is sufficiently high enough to maintain display 330 in a tilted orientation relative to the backing panel but not so high as to prevent a user from pivoting display 330 relative to the associated backing panel. Alternatively, a strut or other support member may be provided between display 330 and the backing panel to maintain the display 330 in its tilted orientation relative to the backing panel.

Those skilled in the art will appreciate that various linkage mechanisms may be provided in the above-described embodiments for interconnecting the pins, latches, or locks, as the case may be, with an associated release mechanism so that movement of the release mechanism results in movement of the associated pins, latches, or locks. Such linkage mechanisms may comprise Bowden wires (refer to the earlier description) and/or links, sliders, cams, followers, and the like. In addition, it should be understood that electrical lines, such as wires or cables, including ribbon cables, are routed through or beside the above-described guide mechanisms or hinge mechanisms to provide an electrical connection between display 330 and the controller 318 of system 300 situated in housing 302. For example, in embodiments having grooves formed in housing 302 and a rail formed on display 330, a slot may be provided within one of the grooves and the electrical lines may exit through an opening provided in the associated rail and be routed through the slot. In other embodiments, the electrical lines between controller 318 and display 330 may be omitted and display 330 may send and receive signals wirelessly to and from controller 318.

The front wall 320 of housing 302 of system 300 has an additional pneumatic port 460 to the left of the air ports 334 as shown best in FIG. 13. Port 460 is couplable to a mouthpiece 452 such as the one shown, for example, in FIG. 21, or a mask 480 as shown, for example, in FIGS. 14 and 15. Mouthpiece 452 and mask 480 are used with system 300 when system 300 performs one or more of the integrated additional therapies such as, for example, the nebulizer therapy, the cough assist therapy, and the PEP therapy, just to name a few. In the illustrated embodiment, suction or negative pressure (sometimes referred to herein, including in the claims, as "vacuum") may be applied to port 460 by system 300 as well, for ultimate application to the mouthpiece 452 or mask 480 coupled to port 460. In addition, the front wall of the housing of display 330 has a pair of input ports 362, 364 just below the electronic display screen 332.

The input ports 362, 364 are configured to be connected to electronic assessment systems, such as an external flow meter (in those embodiments in which system 300 does not have an internal flow meter), an electronic stethoscope 366, a spirometer mouthpiece 378, a tympanic thermometer, a pulse oximeter, a respiration rate monitor, or the like. In other embodiments, one or more ports 362, 364 are provided on housing 302 instead on the housing of display 330. A pair of C-shaped handles 336 are coupled to the side walls 326, 328 of the housing 302 and are grippable by a caregiver to maneuver system 300 along a floor. Additional ports similar to ports 362, 364, which may dedicated to particular ones of the various assessment systems, may provided in some embodiments. A remote on/off switch (not shown), similar to switch 266 of system 200 described above, is couplable to the controller 318 via a port on the housing 302.

An asset tracking badge (not shown) may be attached to one of the walls of the housing 302 so that an asset tracking system of the hospital can keep track of the location of the system 300. Such an asset tracking badge may be the same or similar to those described above in connection with system 200. In other embodiments, the circuitry of system 300 includes a transmitter and/or receiver and/or transceiver to transmit ID data to other portions of the locating-and-tracking system, either periodically or in response to a query signal. In such embodiments having locating-and-tracking circuitry integrated into system 300, the ID data and/or other data transmitted by such circuitry of system 300 may be programmable via appropriate presses of icons or buttons on screen 332 of display 330. In addition to the ID data, system 300 may transmit data indicative of whether or not system 300 is currently in use and optionally, may also transmit data indicative of the amount time left before the current HFCWO therapy session and/or other respiratory therapy session and/or assessment session will end. Thus, a caregiver viewing a remote display screen of a computer of the locating-and-tracking system can receive information regarding the whereabouts of a particular system 300 in the healthcare facility as well as additional information regarding the usage status of the system 300.

Figure 16:
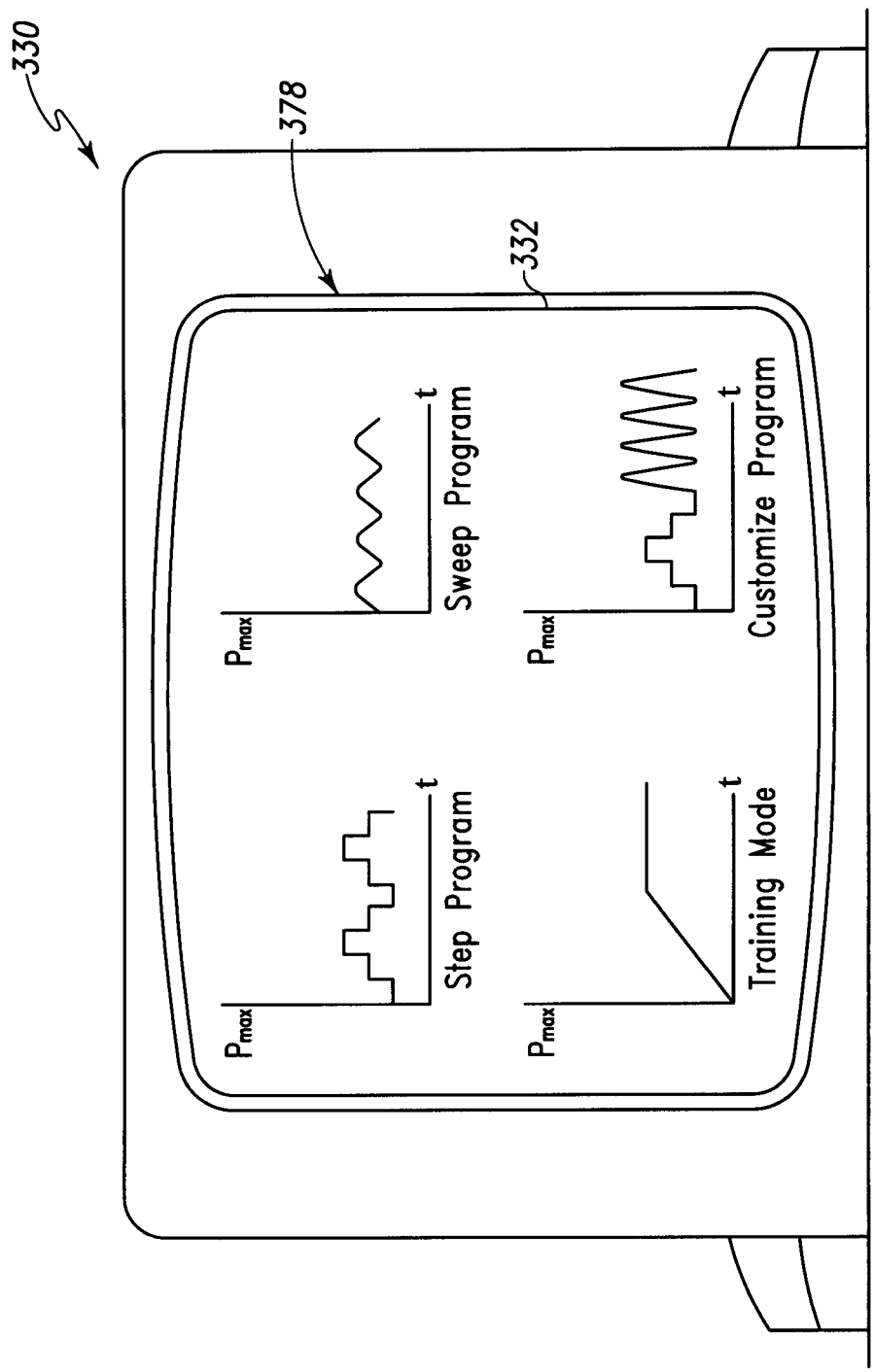
FIG. 16 is a screen shot of a therapy programs screen that appears on a display screen of the display and that has a number of program options indicative of different modes of operation of the system.
Figure 17:
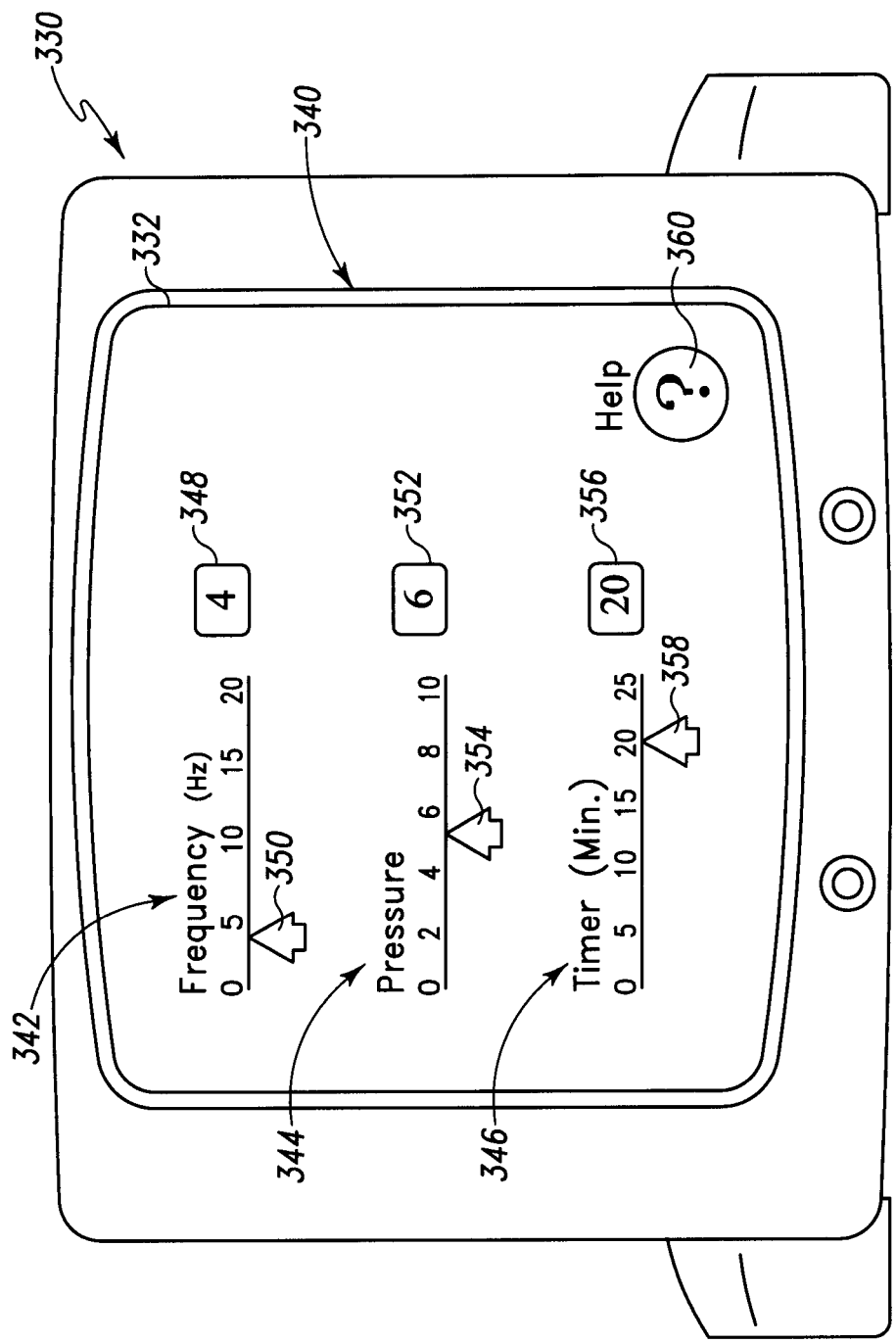
FIG. 17 is a screen shot of a screen that appears on the display screen when the system is in a manual program mode.
Figure 20:
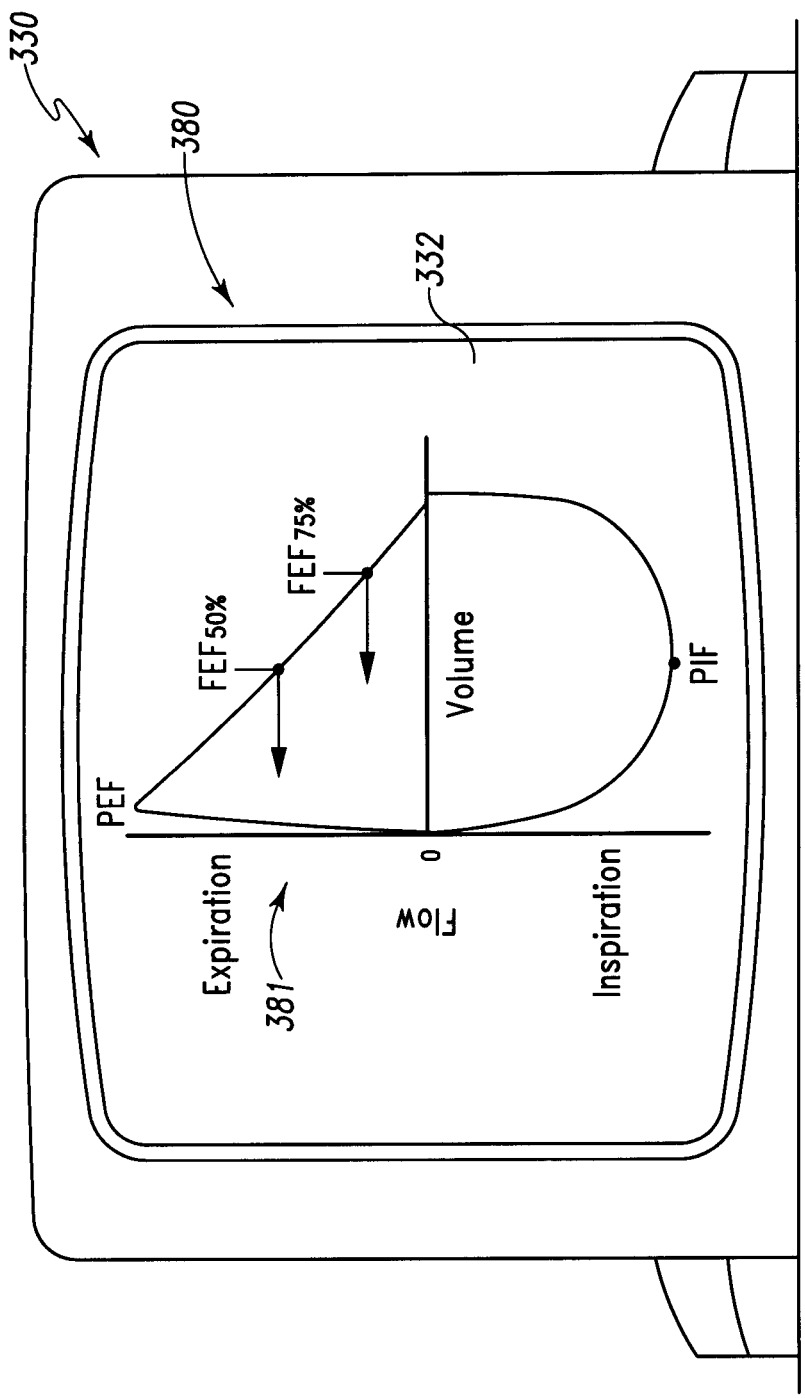
FIG. 20 is a screen shot of a screen showing the output of the spirometer of FIG. 19.

FIGS. 16, 17 and 20 show examples of user interface screens according to one embodiment of system 300. FIG. 16 is a screen shot of a program select screen 338 that appears on the display panel 332 when the system 300 is in a program select mode. As shown in FIG. 16, the air pulse generator 316 has four pre-set program modes, namely, a step program mode, a sweep program mode, a training program mode, and a custom program mode. The caregiver selects a particular program mode by simply touching the associated quadrant of the screen 338. For example, the caregiver selects the step program mode by touching upper left quadrant of the screen 338.

The step and sweep program modes are substantially as described in U.S. Patent Application Publication No. US 2004/0097842 which is already incorporated by reference herein. The training program mode allows the caregiver to start at a desired starting frequency and intensity for the HFCWO therapy and automatically gradually increase the frequency and intensity over a predetermined period of time or a programmed period of time to a desired maximum frequency and intensity. This is useful for frail patients and patients that are not accustomed to HFCWO therapy in order to help them get accustomed to this type of therapy before using more powerful settings. The software for the four preset program modes is stored in a memory associated with the controller 318. In the custom program mode, the caregiver is able to create a special waveform for a particular patient's therapy. Such a special waveform may be in accordance with wave type, frequency, pressure, and timing parameters of the caregiver's choosing or may be in accordance with a menu of special waveforms preprogrammed into system 300. In the illustrative customize program icon on screen 338, one example of a possible custom waveform is shown in which system 300 operates according to a step program for a first period of time and then changes automatically to a sweep program for a second period of time.

In addition to the four program modes just described, the air pulse generator 316 is operable in a manual program mode. In the manual program mode, the caregiver manually sets the air pulse frequency, the bias line pressure and the duration of the HFCWO therapy. FIG. 17 is a screen shot of a screen 340 that appears on the display panel 332 when the system 300 is in the manual program mode. The screen 340 shows three ranges 342, 344, 346 of therapy settings, namely, the frequency of air pulses applied to the vest, the bias line pressure and the duration of the HFCWO therapy. The air pulse frequency can be varied between 0 Hz to 20 Hz. The current value of the air pulse frequency setting (4, in the illustration shown in FIG. 17) is shown in a box 348 on the right side of the frequency range 342. A box 352 to right of range 344 shows the current value of the relative bias line pressure setting and a box 356 to right of range 346 shows the current value of the duration setting of the HFCWO therapy.

The caregiver may change the air pulse frequency by touching and then dragging an arrow icon 350 toward the left side of range 342 to decrease the air pulse frequency or by touching and then dragging icon 350 toward the right side of range 342 to increase the air pulse frequency. The default frequency in one embodiment is 12 Hz, although embodiments having other default frequencies are within the scope of this disclosure. Likewise, the caregiver may vary the relative bias line pressure setting to a value between 0 and 10 by moving an arrow icon 354 toward the left side or the right side of the associated range 344. The default bias line pressure is 3, although other bias line pressure default values are within the scope of this disclosure. In addition, the caregiver may vary the duration of the HFCWO therapy between 0 and 20 minutes by dragging an arrow icon 358 toward the left side or the right side of the associated range 346. The default time is 10 minutes. The therapy automatically stops when the duration is complete, and a message is shown on the display panel 332 that that the session has ended and the therapy is complete. In some embodiments, the number in box 356 changes during the HFCWO to show the amount of time left before the therapy session ends and the arrow icon 358 moves to the left along range 346 to show the amount of time left in the therapy session. In some embodiments, the number in box 356 shows both minutes and seconds, rather than showing just minutes.

Screen 340 has a help button 360 that allows the caregiver to browse the product documentation, watch an in-service video, view clinical studies and claims, view technical literature, view user manuals, and access technical support contact information. All of this information is stored in one or more memory devices included in or associated with controller 318 of system 300. Such memory devices may include one or more RAM, ROM, cache memory, or non-volatile memory devices, and the like as well as including other types of storage devices such as floppy or removable disk drives, a direct access storage device (DASD), a hard disk drive, a CD drive, a DVD drive, a tape drive, and the like that are included in, associated with, or coupled to controller 318 and that read data stored on the corresponding type of data storage media (e.g. memory chip, floppy disk, CD, DVD, tape, etc.). Thus, system 300 may comprise multiple storage devices that are coupled to controller 318, as well as comprising a portion of the memory of controller 318, such as the memory of a microcontroller integrated circuit chip. The system 300 also may include one or more reference cards (not shown) that provide a quick reference to the commonly used functionalities of the system 300, such as, for example, the three pre-set therapy programs, nebulizer therapy, and the use of a spirometer for making a lung assessment of a patient. The reference cards may be configured as pull-out cards and the housing 302 may include one or more slots (not shown) for storing these reference cards.

The system 300 may be integrated with a spirometer, such as the spirometer 370 shown in FIG. 19, for the purpose of making a lung assessment of a patient. The spirometer 370 is configured to measure the lung volume (the volume of air inhaled and exhaled), the flow rate (the displacement volume per unit of time) and the lung elasticity of the patient. A patient lung assessment may be made prior to starting a HFCWO therapy for a new patient to establish a base line (i.e., the patient's lung volume, flow rate, and lung elasticity prior to a HFCWO therapy regimen and/or prior to a particular HFCWO therapy session) and to determine optimum settings for the HFCWO therapy for the patient, which optimum settings may change from time to time based on the condition of the patient. The optimum settings for a HFCWO therapy may include the frequency of the air pulses applied to the vest, the bias line pressure, and the duration of the HFCWO therapy. In addition, a patient lung assessment may be made periodically during the HFCWO therapy regimen to evaluate a patient's progress.

As shown in FIG. 19, the spirometer 370 includes an interface device 372 that is located within the housing 302. The spirometer interface device 372 is coupled to the controller 318 of the system 300. In some embodiments, the spirometer interface device 372 has a slot 374 in which a PCMCIA (Personal Computer Memory Card International Association) card 376 is inserted. The card 376 is coupled to a mouthpiece 378 which is situated at least, in part, in the patient's mouth during the spirometry tests or assessments. The card 376 and the slot 374 have complementary electrical contacts which mate when card 376 is inserted into slot 374. In addition, the circuitry of interface device 372 adjacent to slot 374 and/or card 376 has a transducer 377 for measuring attributes of the patient's inhalation (also referred to herein as "inspiration") and exhalation (also referred to herein as "expiration"), such as pressure and/or flow rate. The baseline measurements for a patient (for example, the lung volume, flow rate and lung elasticity) may be made with or without the patient undergoing the HFCWO therapy during the spirometry tests. In other embodiments, such as the one shown in FIGS. 12-15, slot 374 and card 376 are omitted and the associated spirometer circuitry is contained within the housing of display 330 and/or within housing 302 of system 300. In such embodiments, an end of a flexible tube 379 extending from mouthpiece 378 is inserted into port 364 to pneumatically couple mouthpiece 378 with the spirometer circuitry, such as to a transducer of the type mentioned above.

To make the baseline measurements, the system 300 is turned on, the patient is seated comfortably in a certain position, the mouthpiece 378 is inserted into the patient's mouth, the card 376 is inserted into the slot 374 (or the hose 378 is inserted into port 364), and the patient starts breathing through his mouth. The patient takes a full breath in and exhales a full breath out. An analog signal representing the flow of the patient's breath is converted into digital values by an analog-to-digital converter included in the interface device 372. From these digital values, application interface (API) software included in the interface device 372 and/or in controller 318 calculates all the successive flow and volume values. The spirometer output is graphically displayed on the display panel 332. The spirometer 370 may collect data for two or more of the patient's breaths and then display a waveform corresponding to the average data for the number of breaths. In some embodiments, the number of breaths for which data is to be collected is programmed by a user of system 300.

Figure 44:
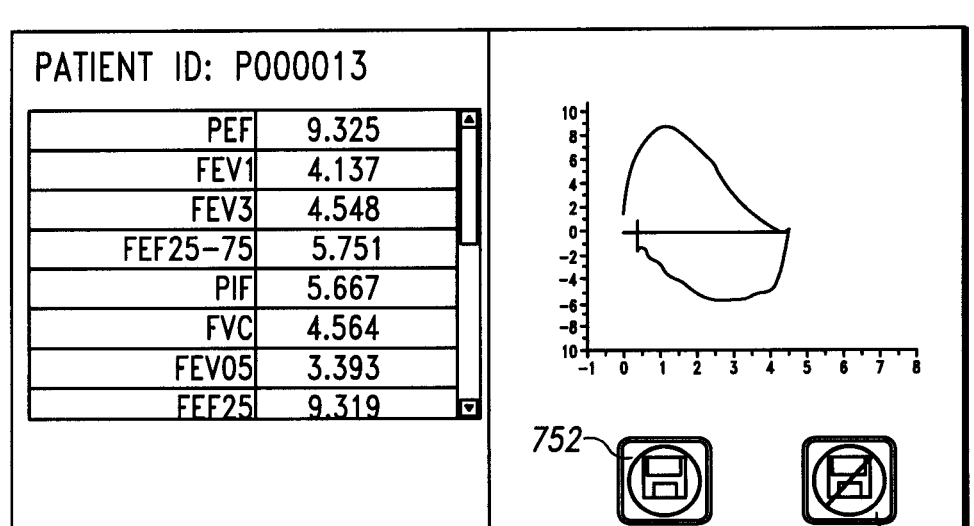
FIG. 44 is a screen shot of the spirometry screen of the system of FIGS. 12-15 after a spirometry test has been run by the system showing tabular and graphical data related to the spirometry test.
Figure 46:
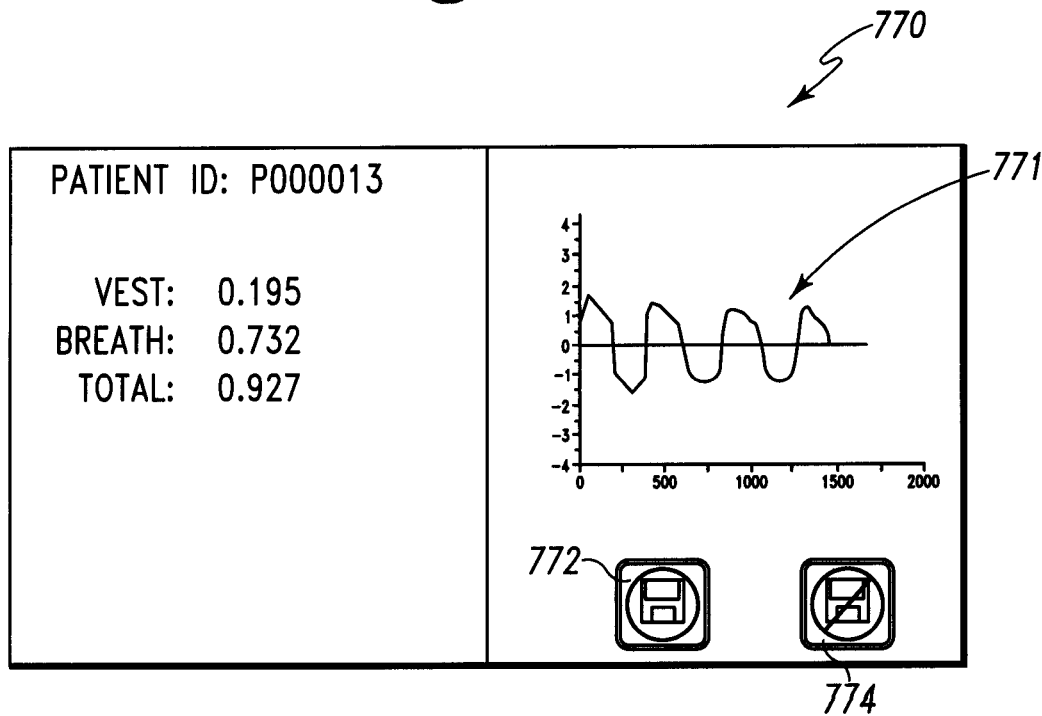
FIG. 46 is a screen shot of the vest-and-spirometry screen of the system of FIGS. 12-15 after a vest-and-spirometry test has been run by the system showing tabular and graphical data related to the vest-and-spirometry test.

FIG. 20 is a screen shot of an example of a screen 380 showing a graph 381 representing the output of the spirometer 370. In FIG. 20, the x-axis of graph 381 represents the lung volume and the y-axis of graph 381 represents the flow rate. The explanation of acronyms used in graph 381 is as follows: 1) PEF—peak expiratory flow, 2) $FEF_{50}$%—forced expiratory flow at 50% of expiration, 3) $FEF_{75}$%—forced expiratory flow at 75% of expiration, and 4) PIF—peak inspiratory flow. Additional examples of the spirometer output are shown in FIGS. 44 and 46 for another embodiment of system 300. If desired, graduated marking showing volume and flow, with appropriate measurement units, may be provided on graph 381.

Some other examples of the values that may be calculated by the API software are: 1) FVC—forced vital capacity, 2) PEFR—peak expiratory flow rate, 3) $FEV_{05}$—forced expiratory flow volume during first half second, 4) $FEV_1$—forced expiratory flow volume during first second, 5) $FEV_3$—forced expiratory flow volume during first three seconds, 6) $FEV_6$—forced expiratory flow volume during first six seconds, 7) $FEF_{25}$—forced expiratory flow @ 25% of expiration, 8) $FEF_{50}$—forced expiratory flow @ 50% of expiration, 9) $FEF_{75}$—forced expiratory flow @ 75% of expiration, 10) $FEF_{25-75}$—forced expiratory flow between 25 and 75% of expiration (also called MMEF—maximum mid-expiratory flow), 11) FIVC—forced inspiratory vital capacity, 12) PIFR—peak inspiratory flow rate, 13) EV—extrapolated volume, 14) $FIV_{05}$—forced inspiratory volume during first half second, 15) $FIV_1$—forced inspiratory volume during first second, 16) $FIV_3$—forced inspiratory volume during first three seconds, 17) $FIF_{0.2-1.2}$—forced inspiratory flow between 0.2 and 1.2 seconds, 18) $FIF_{50}$—forced inspiratory flow @ 50% inspiration, and 19) $FIF_{25-75}$—forced inspiratory flow between 25 and 75% inspiration.

To determine the optimum settings for the HFCWO therapy for a patient, a patient wearing a HFCWO therapy vest is seated comfortably in a certain position, the air pulse generator 316 is turned on to apply air pulses to the vest, the mouthpiece 378 is inserted into the patient's mouth, the card 376 is inserted into the slot 374 (or the hose 379 is inserted into port 364), and the patient starts breathing through his mouth. The spirometer 370 converts the patient's breath into digital values which are processed by the software included in the interface device 372. The spirometer output is separated into high frequency (greater than 4 Hz in the illustrated embodiment) and low frequency (less than or equal to 4 Hz in the illustrated embodiment) components using software filtering techniques. The magnitude of the high frequency components is measured. The high frequency components of the output correspond to the sympathetic resonance from the vest seen in the patient's airway. In some embodiments, the caregiver varies the air pulse frequency and the bias line pressure to maximize the magnitude of the high frequency components. The higher the magnitude of the high frequency components the more effective is the HFCWO therapy. In other embodiments, the software included in system 300 automatically adjusts the air pulse frequency and the bias line pressure for optimum HFCWO therapy. In such embodiments, therefore, the system may step up the frequency and/or pressure after each of the patient's breaths (i.e., one cycle of inspiration and expiration), or after taking the average of the high frequency spirometry assessment components after two or more of the patient's breaths, and determine which combination of pressure and frequency yields the best results for the particular patient. The spirometer 370 may be of the type marketed by QRS Diagnostic of Plymouth, Minn.

Figure 21:
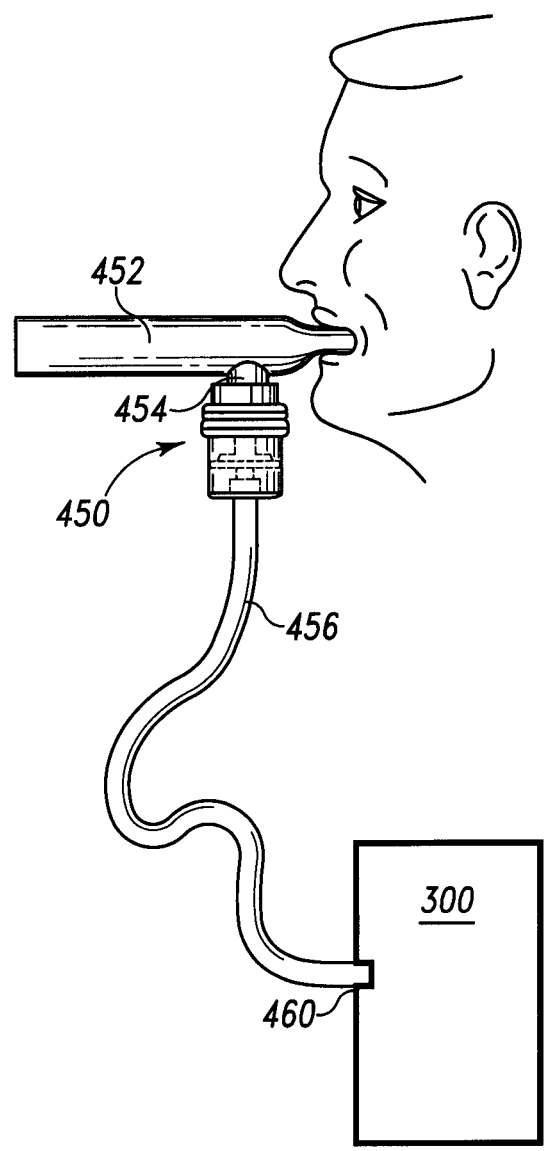
FIG. 21 shows a patient holding a mouthpiece in his mouth, the mouthpiece being coupled to a nebulizer.
Figure 22:
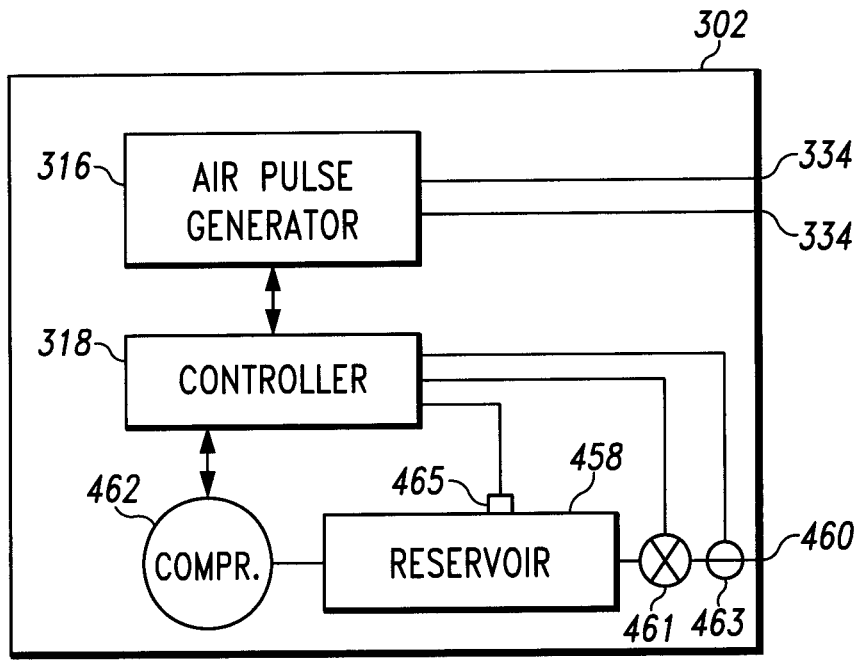
FIG. 22 is a block diagram showing a compressor and a pressurized air reservoir located in the housing of the system of FIG. 12, the pressurized air reservoir supplying pressurized air to the nebulizer of FIG. 21.
Figure 23:
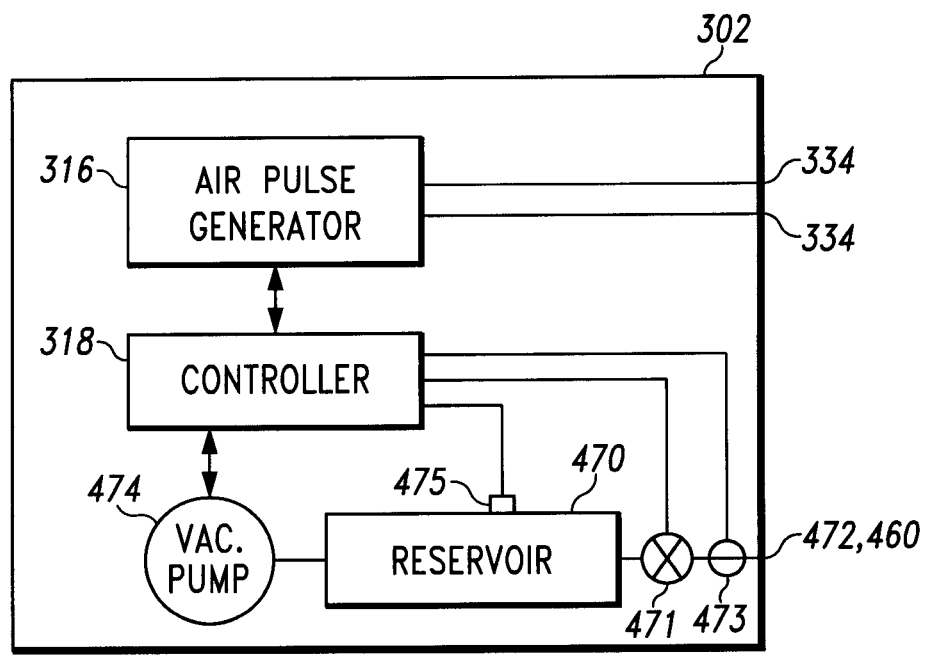
FIG. 23 is a block diagram showing a vacuum pump and a vacuum reservoir located in the housing of the system of FIG. 12, the vacuum reservoir supplying vacuum to a suction device.

FIG. 21 shows diagrammatically a nebulizer 450 which may be integrated with the HFCWO therapy system 300. The nebulizer 450 is coupled to a mouthpiece 452 via a nebulizer port 454 as shown in FIG. 21. During the nebulizer therapy, a tube 456 connects the nebulizer 450 to a pressure source located in the housing 302 of the HFCWO therapy system 300. In the embodiment illustrated diagrammatically in FIG. 22, the pressure source comprises a reservoir 458 that is coupled to the pressurized air port 460 located on the front wall 320 of the housing 302 and that is coupled to a compressor 462 of system 300. The tube 456 connects the pressurized air port 460 to the nebulizer 450. The compressor 462 supplies pressurized air to the reservoir 458. The reservoir 458 provides a low airflow to the nebulizer 450 through the tube 456.

The airflow from system 300 aerosolizes a solution, such as a mild bronchial irritant like hypertonic saline, contained in the nebulizer 450 and allows the patient to inhale the solution. The solution provides moisture to facilitate mucus mobilization and may also help to induce a cough. The nebulizer therapy may be administered by itself without the HFCWO therapy. Alternatively, the nebulizer therapy may be administered simultaneously with the HFCWO therapy to increase sputum inducement. The nebulizer 450 may be of the type marketed by O-Two Medical Technologies Inc. In some embodiments, system 300 includes a nebulizer within housing 302 to aerosolize a solution prior to the aerosolized solution exiting port 460 and, in such embodiments, the nebulizer 450 coupled to mouthpiece 452 is omitted such that hose 456 couples directly to port 454. If desired, a mask 480 may be coupled to port 460 via an associated hose 482 as shown in FIGS. 14 and 15, in lieu of mouthpiece 452 and placed over the patient's nose and mouth during an associated therapy, such as nebulizer therapy.

A suitable electronically controlled valve 461 and a pressure sensor 463 are coupled to or situated in the pneumatic path between reservoir 458 and port 460 as shown diagrammatically in FIG. 22. In some embodiments, valve 461 is a proportional valve that opens and closes by varying amounts to establish the pressure communicated to nebulizer 450. Sensor 463 provides feedback to controller 318 which, in turn, signals valve 461 to open and close, as needed, to maintain the pressure communicated to nebulizer 450 within a tolerance range of a programmed target pressure. In other embodiments, valve 461 may be a two-position valve that is either fully opened or fully closed, such as a solenoid valve, and a pressure regulator may be included in the pneumatic path between reservoir 458 and port 460 to limit the pressure available to nebulizer 450 from system 300. Alternatively or additionally, nebulizer 450 may include its own pressure regulator. A pressure sensor 465 is also coupled to reservoir 458 and provides feedback to controller 318 regarding the pressure therein. Controller 318 signals compressor 462 to operate, as needed, to maintain the pressure within reservoir 458 with a tolerance range of a programmed target pressure. A pressure relief valve (not shown) may be coupled to reservoir 458 in some embodiments to prevent reservoir 458 from being pressurized beyond a predetermined maximum pressure.

In some embodiments, system 300 is also operable to produce negative pressure for use as suction for therapeutic or other purposes. To administer suction during therapy, for example, a mouthpiece, similar to mouthpiece 452 may be placed in the patient's mouth or a mask, similar to mask 480 may be placed over the patient's nose and mouth. A tube similar to tube 454 connects the mouthpiece to a vacuum source located in the housing 302 of the HFCWO therapy system 300. In the embodiment illustrated diagrammatically in FIG. 23, the vacuum source comprises a reservoir 470 that is coupled to a vacuum port 472 located on the front wall 320 of the housing 302 and that is coupled to a vacuum pump 474. The vacuum pump 474 is operable to evacuate air out of reservoir 470 thereby to create a negative pressure in reservoir 470.

In the illustrative example, a suitable electronically controlled valve 471 and a pressure sensor 473 are coupled to or situated in the pneumatic path between reservoir 470 and port 472 as shown diagrammatically in FIG. 23. As was the case with valve 461, valve 471 is a proportional valve that opens and closes by varying amounts to establish the pressure communicated to port 472. Furthermore, as was the case with sensor 463, sensor 473 provides feedback to controller 318 which, in turn, signals valve 471 to open and close, as needed, to maintain the pressure communicated to port 472 within a tolerance range of a programmed target pressure. In other embodiments, valve 471 may be a two-position valve that is either fully opened or fully closed, such as a solenoid valve, and a pressure regulator may be included in the pneumatic path between reservoir 458 and port 472 to limit the pressure available at port 472 from system 300. A pressure sensor 475 is also coupled to reservoir 470 and provides feedback to controller 318 regarding the pressure therein. Controller 318 signals vacuum pump 474 to operate, as needed, to maintain the negative pressure within reservoir 470 with a tolerance range of a programmed target pressure. A vacuum relief valve (not shown) may be coupled to reservoir 470 in some embodiments to prevent reservoir 470 from being pressurized below a predetermined minimum pressure.

Additionally or alternatively, reservoir 470 may be coupled to port 460. Thus, in some embodiments, port 460 is coupled to both a positive pressure source and to a negative pressure source. In such embodiments, a Y-type connector or a manifold may be provided between port 460 and the associated positive and negative pressure sources. If a Y-type connector or manifold is provided, then valves 461, 471 and pressure sensors 463, 473 may be coupled to the Y-type connector or manifold, as the case may be. In the illustrative examples of FIGS. 22 and 23, the positive pressure source comprises compressor 462 and reservoir 458 and the negative pressure source comprises vacuum pump 474 and reservoir 470. In other embodiments, one or both of reservoirs 458, 470 are omitted such that compressor 462 alone serves as the positive pressure source and/or such that vacuum pump 474 alone serves as the negative pressure source. Other positive and negative pressures sources, such as blowers, pumps, and compressors of all types are within the scope of this disclosure as being included in system 300.

Cough assist therapy is one example of a therapy in which both positive pressure and negative pressure is communicated to a patient from port 460. During cough assist therapy, mask 480 (FIG. 14) is usually placed over the patient's nose and mouth, although a mouthpiece, similar to mouthpiece 454 with or without nebulizer 450 may be used in lieu of mask 480, if desired. Tube 482 connects the mask 480 to the pressurized air port 460 located on the front wall 320 of the housing 302 as shown in FIG. 14 and as mentioned above. The patient holds the mask 480 against his face over his nose and mouth or, in some embodiments, a strap is provided to hold mask 480 in place on the patient. During cough assist therapy, pressurized air is forced into the mouth and/or nose of the patient through the mask 480 and then quickly sucked out to simulate a cough. If desired, the cough assist cycle may be repeated several times. The cough assist therapy device may be of the type marketed by J. H. Emerson Co. of Cambridge, Mass. In some embodiments having only a compressor or pump, such as compressor 462 or pump 474, without an associated reservoir, the direction of operation of a motor of such a compressor or pump may be reversible such that the compressor or pump is configured to supply positive pressure to port 460 when operating in a first direction and to supply negative pressure to port 460 when operating in a second, opposite direction.

Alternatively or additionally, system 300 may be integrated with a positive expiratory pressure (PEP) therapy device; an intermittent positive pressure breathing (IPPB) therapy device of the type marketed by Vortran Medical Technology 1, Inc. of Sacramento, Calif.; a continuous positive airway pressure (CPAP) therapy device; and/or a Bi-level Positive Airway Pressure device which provides two different levels of positive airway pressure depending upon whether the patient is inhaling or exhaling. During the administration of any of these therapies, the patient either places a mouthpiece in his mouth or places a mask over his nose and mouth. It should be noted that, in the description which follows it is assumed that a mouthpiece is being used.

A tube or hose extends from the mouthpiece associated with the one or more additional therapies to a port in housing 302 of system 300. The port for one or more of these additional therapies included in system 300 may be one of ports 460, 364 or may be one or more different, additional ports provided in housing 302 and/or in the housing of display 330. Circuitry associated with the additional one or more therapies may be included in controller 318 of system 300 or may be provided as separate circuitry such as, for example, circuitry adjacent to the one or more additional ports to which the mouthpiece couples for the one or more additional therapies. Such additional circuitry may include one or more sensors for measuring pressure, flow rate, flow volume, and the like for the associated one or more additional therapies. If such separate circuitry is provided for the one or more additional respiratory therapies, such circuitry may be electrically coupled to controller 318 for the exchange of data or control signals therewith or to receive power therefrom.

The mouthpieces and/or masks used with the additional respiratory therapies of system 300 may include various valves, knobs, or other controls for controlling various aspects of the therapy delivered to the patient and may include nebulizers. For example, the PEP mouthpiece may have a valve which remains fully open during the inspiratory cycle but that closes partially during expiratory cycle to require the patient to try to force the air out. In some embodiments, the valve of the PEP mouthpiece flutters to cause the patient's lungs to vibrate. A mouthpiece used with IPPB therapy, for example, may have a knob which is used to adjust a valve that controls peak pressure during inspiration, another knob which is used to adjust another valve that controls resistive pressure during expiration, and yet another control used to adjust the flow rate during inspiration. Such an IPPB mouthpiece may include a nebulizer. Data (date, time, pressure, flow rate, flow volume, etc.) regarding the one or more additional respiratory therapies may be acquired by system 300 for assessment and stored in a memory device associated with the controller and/or the circuitry of the one or more additional therapies. Such data is acquired by one or more sensors (flow meters, pressures sensors, etc.) that are included in system 300, that are in electrical communication with controller 318 (possibly through other circuitry associated with the particular therapy) and that are in pneumatic communication with the one or more ports of the associated one or more additional therapies.

Referring now to FIGS. 18 and 41-51, examples of user interface screens, or portions thereof, according to another embodiment of system 300 are shown. It will be appreciated that system 300 includes software that is stored in one or more memories devices associated with controller 318 and that, when executed, causes various user interface screens, such as the user interface screens shown in FIGS. 18 and 41-51, to be displayed on the touch screen display panel 332 at different times depending upon user inputs to system 300.

Figure 18:
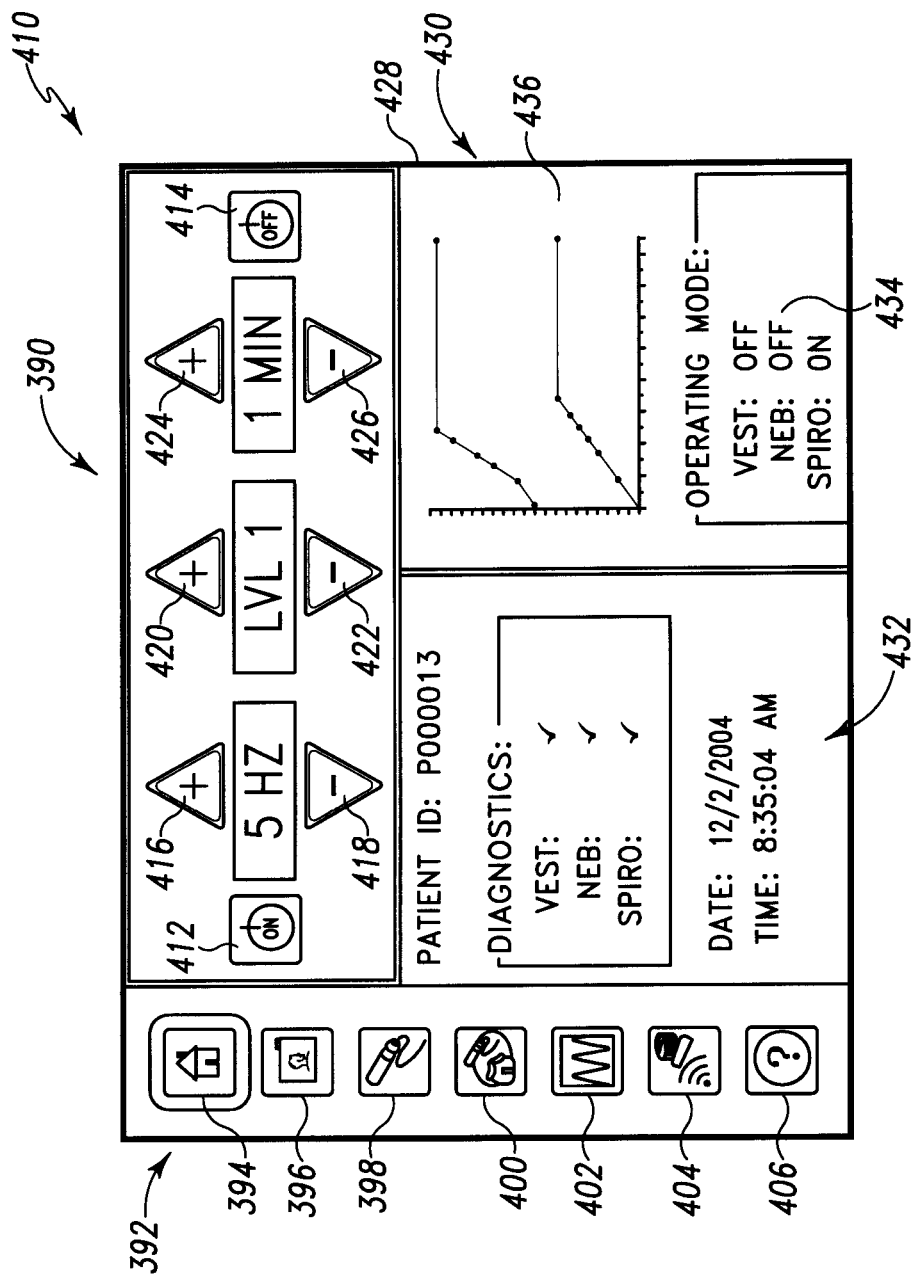
FIG. 18 is a screen shot of a home screen of the system of FIGS. 12-15.

FIG. 18 is a screen shot of a home screen 390 that appears on the display screen 332. Screen 390 is the default screen that is normally shown on display screen 332. Thus, if other screens discussed herein are shown but a user does not provide any inputs to system 300 during the display of such screens for a predetermined timeout period, or if system 300 finishes acquiring data and/or displaying the acquired data for a predetermined timeout period, the system 300 may automatically default to displaying home screen 390. On the left side of the home screen 390 is a mode change field 392 which includes a home screen icon 394, a patient icon 396, a spirometer icon 398, a vest & spirometer icon 400, a vest program icon 402, a data download icon 404, and a help icon 406. On the upper right side of the home screen 390 is a value change field 410 which includes the following buttons or icons: on button 412, off button 414, upper left button 416, lower left button 418, upper middle button 420, lower middle button 422, upper right button 424 and lower right button 426. The caregiver may modify the operation of the air pulse generator 316 by using the buttons 416, 418, 420, 422, 424, 426. The function of the buttons 416, 418, 420, 422, 424, 426 may vary depending on the current state or mode of air pulse generator 316 and furthermore, buttons associated with controlling others of the therapies or functions of system 300 may be displayed in field 410 in lieu of buttons 416, 418, 420, 422, 424, 426.

On the lower right side of the home screen 390 is a window 428. A status field 430 appears in the window 428 of the home screen 390 in response to the caregiver selecting the home screen icon 394, or in response to system 300 automatically displaying home screen 390. The left side 432 of the status field 430 includes a patient ID number, a list of devices connected to one or more of the ports of system 300, and the date and the time that an associated therapy was administered. In the illustrated example of screen 390, a vest (such as one of those described below), spirometer 370 (FIGS. 19 and 20), and a nebulizer 450 (FIGS. 21 and 22) are coupled to the system 300.

System 300, therefore, includes sensors to detect the coupling of hoses 317 to ports 334, to detect the coupling of hose 456 to port 460, and to detect the coupling of hose 379 to port 364 (or insertion of card 376 into slot 374). Such sensors provide signals to controller 318, possibly through other associated circuitry in some instances, and controller 318 then determines the information to be shown on portion 432 of window 428 based on the software programming of system 300. In some embodiments, one or more of these sensors comprise switches that are adjacent respective ports 334, 364, 460 (or slot 374) and that change state (such as closing to make a contact) in response to insertion of the associated hose 317, 379, 457 into the corresponding port 334, 364, 460 (or insertion of card 376 into slot 374). Other sensors, such as proximity sensors including capacitive sensors or Hall effect sensors to sense the presence of a magnet attached to the end of a hose (or to a card), as well as force sensors such as strain gages or other resistive sensors that sense insertion of a hose into a port (or a card into a slot), or even electrical leads that have an electrical path closed due to insertion of a hose into a port (or a card into a slot), are within the scope of this disclosure for inclusion in system 300 to detect the coupling of hoses 317, 379, 457 to ports 334, 364, 460 (or insertion of card 376 into slot 374). Additional sensors associated with other ports of systems, such as port 362 to which an electronic stethoscope is couplable as discussed above and any ports associated with additional respiratory therapies included in system 300 as discussed above, are contemplated by this disclosure.

The lower right side 434 of the status field 430 shows an indication of which of the devices connected to the system 300 are on or enabled or currently being used. Thus, controller 318 monitors when air pulse generator 316 is operating and sensors adjacent to ports 364, 460 detect whether a patient is breathing though an associated mouthpiece or mask and/or whether positive or negative pressurized air is being delivered through an associated port 364, 460 and controller 318 then determines the information to be shown on portion 434 of window 428 based on the software programming of system 300. The upper right side 436 of the status field 430 shows tabular, numerical, and/or graphical data indicative of the operation and/or the output of one or more of the therapy devices of system 300. In the illustrated example of portion 434 of screen 390, the spirometer 370 is on, while the vest (e.g., the air pulse generator 316) and the nebulizer 450 are off. Also in the illustrative example, portion 436 has displayed therein a graph of data associated with the HFCWO therapy of system 300. In some embodiments, the data shown on portion 436 of window 428 is selectable by touching the associated operating mode description (e.g., "vest," "neb," and "spiro") on portion 434 of window 428.

User interface screens shown in FIGS. 41, 43, 45, 47, 49, and 51 appear in the window 428 of the home screen 390 in response to the caregiver selecting the associated icon 396, 398, 400, 402, 404, 406, respectively. In some embodiments, the mode change field 392 and the value change field 410 continue to be displayed on the left side and the upper right side of the home screen 390 regardless of which one of the icons 394, 396, 398, 400, 402, 404, 406 is selected by the caregiver. In other embodiments, fields 392, 410 may change depending upon the particular respiratory therapy associated with the information being displayed in window 428.

Figures 41, 42:
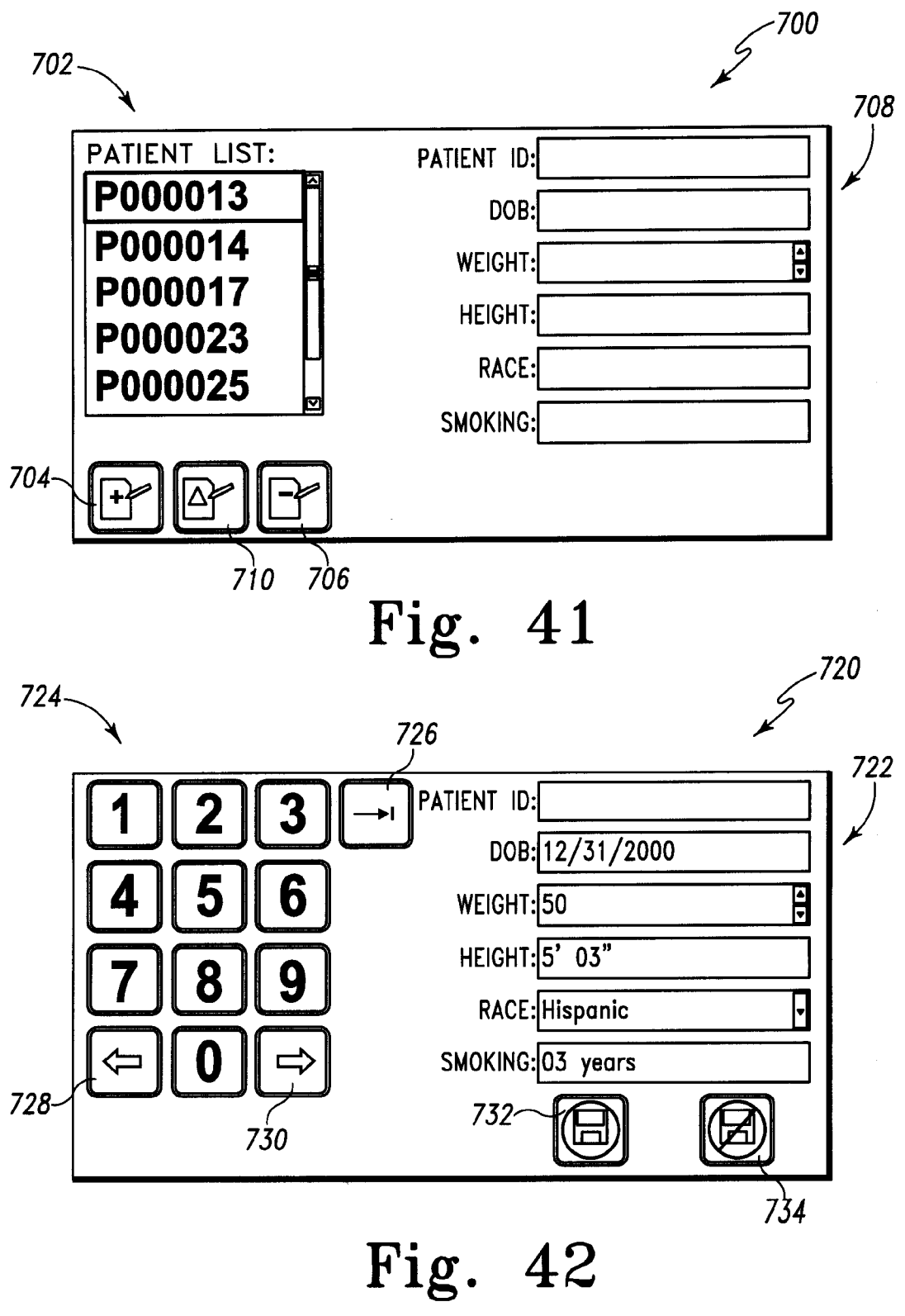

FIG. 41 is a screen shot of a patient screen 700 that appears in window 428 in response to the patient icon 396 being selected. On the left side of the patient screen 700 is a patient list 702, which lists the patient ID numbers of the patients for which system 300 is used to delivery one or more therapies. When a particular patient is selected by using scroll up and scroll down buttons 704, 706 in the lower left corner of the screen 700, information concerning the selected patient appears in a set of text boxes in a patient information field 708 on the right side of the screen 700. In the illustrated embodiment, the text boxes of the patient information includes the patient ID number, date of birth, weight, height, race, and an indication of whether the patient smokes and, if he does, how long.

The lower right hand corner of the patient screen 700 includes an edit button 710 located between the scroll up and scroll down buttons 704, 706 as shown in FIG. 41. Once a patient is selected on list 702, the home icon 394 may be touched, or some other icon 396, 398, 400, 402, 404, 406 touched, to display other information in window 728. In response to the selection of a particular patient on list 702 and selecting another icon 394, 396, 398, 400, 402, 404, and 406, system 300 is automatically configured to operate according to the settings programmed into system 300, either manually or via a previous assessment, for the particular patient so selected. Thus, in the case of HFCWO therapy, for example, selection of a patient on screen 702 results in system 300 being configured to operate according to the frequency, pressure, and duration programmed previously into system 300. Thus, the caregiver does not need to reconfigure system 300 for each particular patient each time system 300 is used with any particular patient. In this way, system settings which produce good therapeutic results, or even optimum therapeutic results, for each of the various patient with which system 300 is used, are stored in one or more of the memory devices associated with controller 318 for later recall by system 300. This saves valuable caregiver time in setting up system 300 for delivery of the HFCWO therapy or other therapies to the associated patients. In addition, data about prior therapy sessions for the particular patient is accessible for viewing on screen 332 once a patient has been selected in this manner.

FIG. 42 is a screen shot of a patient edit screen 720 that appears on the display panel 332 in response to edit button 710 on the patient screen 700 being selected. A patient information field 722, which corresponds to the patient information field 708, is located on the right side of the screen 720. The patient ID number in the patient information field 722 is grayed out since the particular patient's data is the data to be edited. The left side of the screen 720 includes a plurality of numerical keys 724 for editing the patient information. Also included on the left side of the screen 720 are a scroll down key 726 and back and forward space keys 728, 730. The scroll down key 726 is used to select the patient information that is to be edited. Thus, successive presses or touches of icon 726 causes successive text boxes in field 722 to become highlighted, selected, or activated, for editing. Once a particular text box is selected for editing, presses of keys 724, 728, 730 change the information in the selected text box. Located in the lower right corner of the screen 720 are save and cancel keys 732, 734. Pressing save key 732 causes the patient data in the text boxes of field 722 to be saved in memory of system 300 with the changes made thereto, whereas pressing cancel key 734 cancels the changes made to the patient data in the text boxes of field 722 such that the previous patient data prior to any of the changes being made is saved in memory of system 300.

Figure 43:
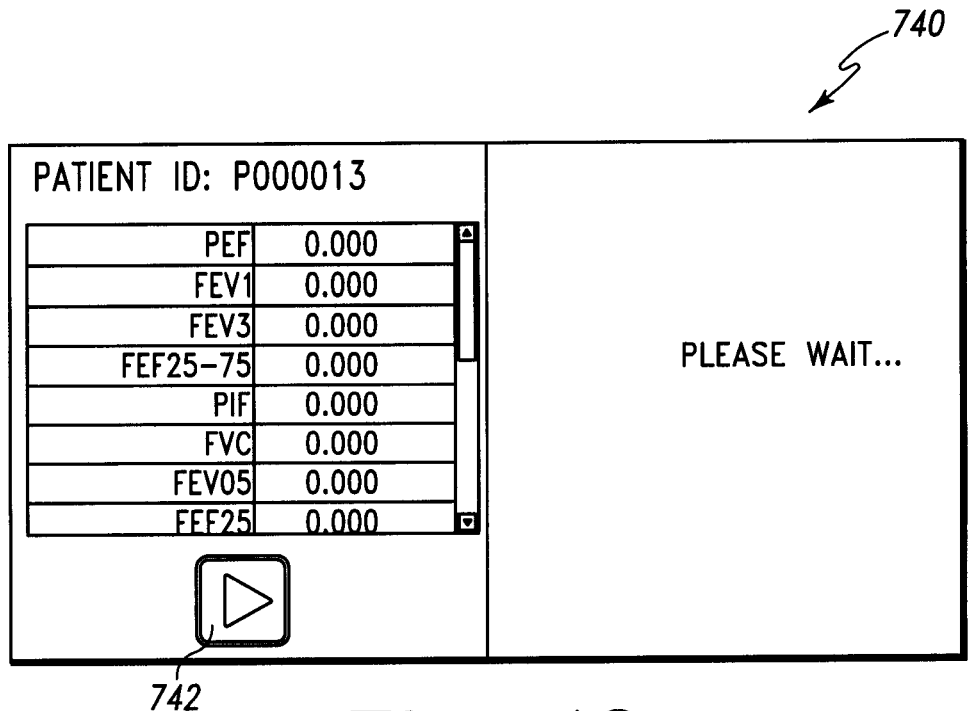
FIG. 43 is a screen shot of a spirometry screen of the system of FIGS. 12-15 prior to a spirometry test being run by the system.

FIG. 43 is a screen shot of a spirometry screen 740 that appears in the window 428 in response to the spirometer icon 398 being selected. The upper left side of the screen 740 lists the ID number of the patient undergoing the spirometry test or assessment. The lower left side of the screens 740 includes a table of various pulmonary function values associated with the spirometry test. The explanation of the acronyms used in FIG. 43 is given below. Located on the lower left side of the screen 740 is a start test button 742. The spirometry test is started when the button 742 is selected. The right side of the screen 740 is reserved for depicting the graphical output of the spirometer after the spirometry test is completed or during the spirometry test.

FIG. 44 is a screen shot of a spirometry screen 750 that appears in window 428 after the spirometry test is completed. The upper left side of the screen 750 lists the ID number of the patient that underwent the spirometry test. The lower left side of the screen 750 depicts various pulmonary function values, the explanation of which appears below. The right side of the screen 750 depicts the graphical output of the spirometer. Located on the lower right side of the screen 750 are save and cancel keys 752, 754. Key 752 is pressed to store the results of the spirometry test in one or more of the memory devices associated with controller 318. Key 754 is pressed to delete the results of the test and not store them. The explanation of the acronyms used in FIGS. 43 and 44 is as follows: PEF (peak expiratory flow), $FEV_1$ (forced expiratory flow volume during first second), $FEV_3$ (forced expiratory flow volume during first three seconds), $FEF_{25\text{-}75}$ (forced expiratory flow between 25% and 75% of expiration), PIF (peak inspiratory flow), FVC (forced vital capacity), $FEV_{0.5}$ (forced expiratory flow volume during first half second, and FFF (forced . . . flow).

Figure 45:
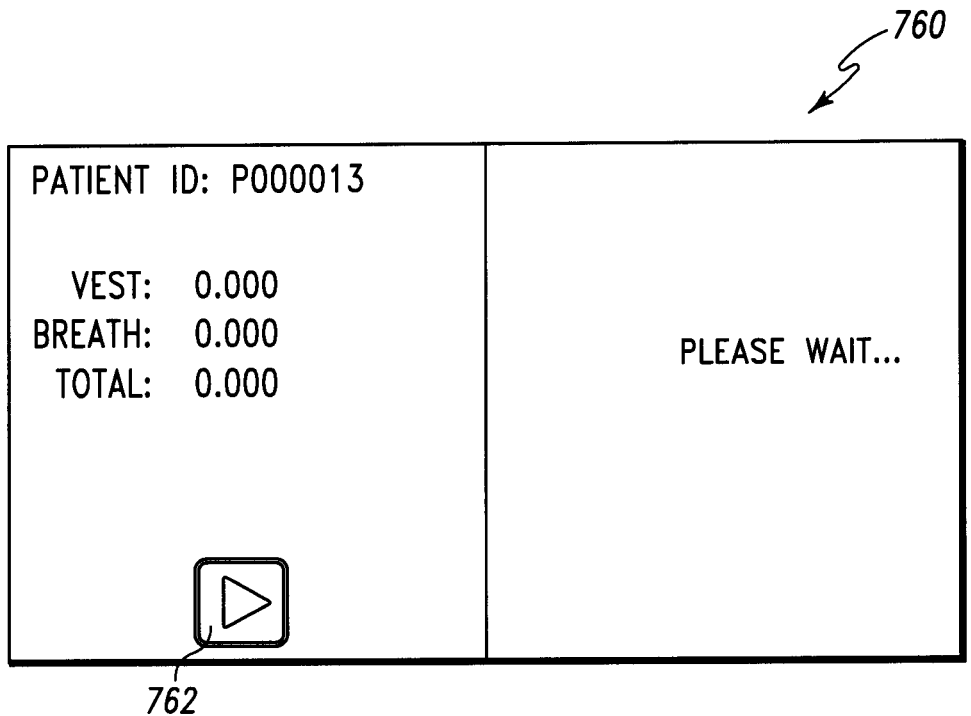
FIG. 45 is a screen shot of a vest-and-spirometry screen of the system of FIGS. 12-15 prior to a vest-and-spirometry test being run by the system.

FIG. 45 is a screen shot of a vest & spirometry screen 760 that appears in the window 428 in response to the vest & spirometer icon 400 being selected. During the vest & spirometry test, the spirometry measurements are made while the patient is undergoing the HFCWO therapy of system 300. The upper left side of the screen 760 lists the ID number of the patient undergoing the vest & spirometry test. The lower left side of the screen 740 is reserved for pulmonary volume values—namely, the vest volume, the breath volume and total volume. Located on the lower left side of the screen 760 is a start test button 762. The vest & spirometry test is started when the button 762 is selected. The right side of the screen 760 is reserved for depicting the graphical output of the spirometer when the vest & spirometry test is completed.

FIG. 46 is a screen shot of a vest & spirometry screen 770 that appears in window 428 when the vest & spirometry test is completed. The upper left side of the screen 770 lists the ID number of the patient that underwent the spirometry test during HFCWO therapy. The lower left side of the screen 770 depicts the vest volume, the breath volume and total volume. The "vest" volume is the volume of the patient's inspiration and expiration attributable to the forces applied to the patient by the HFCWO therapy portion of system 300 and the "breath" volume is the volume of the patient's inspiration and expiration attributable to the patient's normal breathing during the HFCWO therapy. The total volume is the sum of the "vest" volume and the "breath" volume. Thus, controller 318 of system has software which is programmed to determine the vest, breath, and total volumes based on the data acquired by the spirometer included in system 300.

The right side of the screen 770 includes a graph 771 which graphically depicts the breath volume data as shown in FIG. 46. In the illustrative example, a first sinusoidal-like tracing is superimposed on a second sinusoidal-like tracing, with the first tracing having higher peaks and lower valleys than the second tracing. The first tracing, therefore, represents the total inhalation and expiration and the second tracing represents the patient's normal breathing. Thus, the difference between the first tracing and the second tracing represents the volume of inspiration and expiration attributable to the HFCWO therapy delivered to the patient by system 300. The volume totals on the left side of the screen 770 are determined by integrating some or all of the area under the first and second tracings (although, the absolute value of the integral of the portions of the first and second tracings below the x-axis may be used so as to be additive to the integral of the portions of the first and second tracings above the x-axis). Located on the lower right side of the screen 770 are save and cancel keys 772, 774. Key 772 is pressed to store the results of the vest & spirometry test in one or more of the memory devices associated with controller 318. Key 774 is pressed to delete the results of the vest & spirometry test and not store them.

Figure 47:
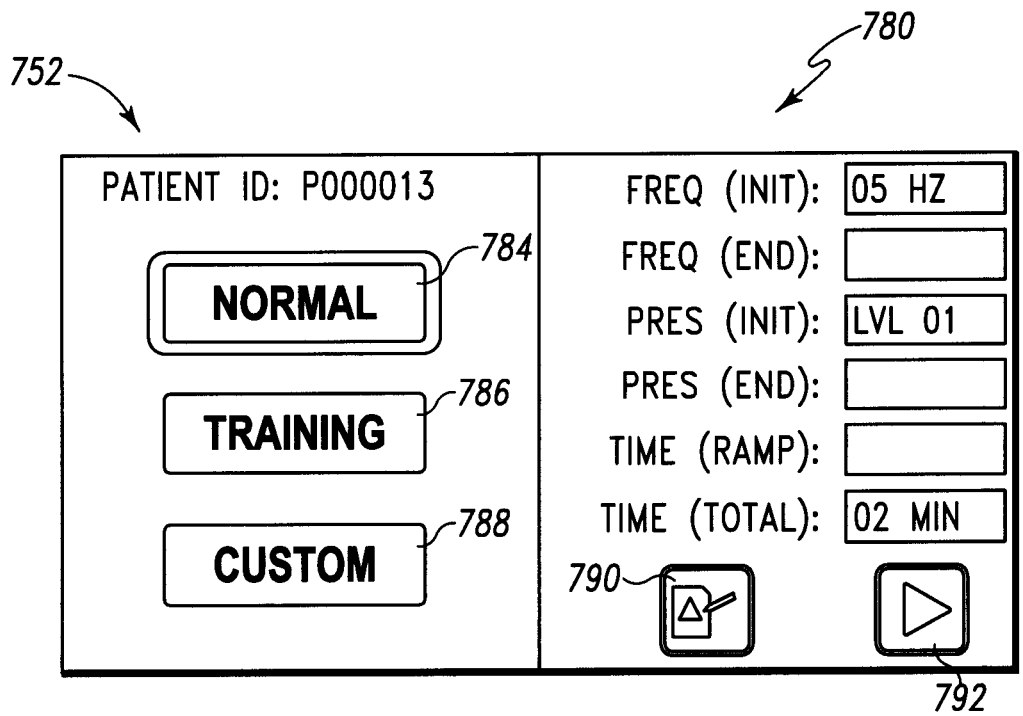
FIG. 47 is a screen shot of a vest program screen of the system of FIGS. 12-15 having vest mode control buttons which are usable to establish which mode is to have the associated parameters programmed.

FIG. 47 is a screen shot of a vest program screen 780 that appears in the window 428 in response to the vest program icon 402 being selected. As shown in FIG. 47, in the second embodiment of the user interface software, the air pulse generator 316 has three pre-set program modes, namely, a normal program mode, a training program mode, and a custom program mode. In addition to the three pre-set program modes, the air pulse generator 316 is operable in a manual program mode by using the buttons 412, 414, 416, 418, 420, 422, 424, 426 which appear in field 410 of home screen 390, for example. Buttons 412, 414, 416, 418, 420, 422, 424, 426 are used to control the HFCWO therapy of system 300 in substantially the same manner as buttons 242, 244, 246, 248, 250, 252, 254, 256 are used to control the HFCWO therapy of system 200. Thus, button 412 is pressed to turn on the HFCWO therapy of system 300; button 414 is pressed to turn off the HFCWO therapy; buttons 416, 418 are pressed to increase and decrease, respectively, the frequency of the HFCWO therapy of system 300 in the manual mode; buttons 420, 422 are pressed to increase and decrease, respectively, the baseline pressure of the HFCWO therapy of system 300 in the manual mode; and buttons 424, 426 are pressed to increase and decrease, respectively, the duration of the HFCWO therapy of system 300 in the manual mode.

The upper left side of the screen 780 lists the ID number of the patient whose HFCWO therapy parameters or settings (i.e., the frequency, pressure and time) are being programmed as shown in FIG. 47. Located on the lower left side of the screen 780 is an air pulse generator mode control field 782, which includes a normal program mode button 784, a training program mode button 786 and a custom program mode button 788. Listed on the upper right side of the screen 780 are text boxes in which air pulse generator settings, namely, initial frequency, ending frequency, initial pressure, ending pressure, ramp time, and total time, are shown. Located on the lower right side of the screen 780 are edit and start buttons 790, 792. The HFCWO therapy starts when the start button 792 is selected.

In the normal program mode of system 300, the air pulse frequency and the bias line pressure are preset and these values, once set, will be the default values for the manual program mode of the HFCWO therapy. Accordingly, unless a caregiver or user changes these default values in the normal program mode, system 300 will return back to these default values for a particular patient even if buttons 416, 418, 420, 422, 424, 426 are manipulated in the manual program mode during a particular therapy session. In the custom program mode of system 300, the caregiver creates a special waveform for a particular patient's therapy in a manner substantially similar to that described above in connection with the custom program mode of system 200. Thus, the discussion above of the custom program mode of system 200 is equally applicable to system 300. The training program mode allows the caregiver to start at a desired starting frequency and intensity for the HFCWO therapy and automatically gradually increase the frequency and intensity (e.g., base line pressure) throughout the duration of the therapy to a desired maximum frequency and intensity in a manner substantially similar to that described above in connection with the training program mode of system 200. Thus, the discussion above of the custom program mode of system 200 is equally applicable to system 300.

Figure 48:
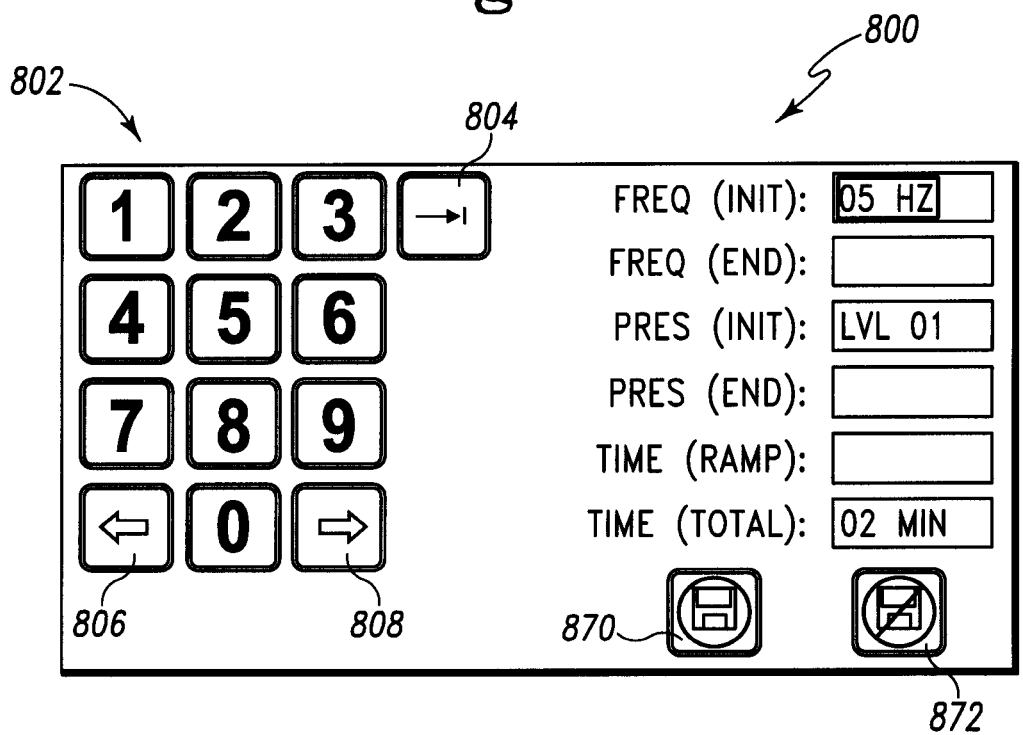
FIG. 48 is a screen shot of a vest program edit screen of the system of FIGS. 12-15 showing edit keys on the left side of the screen that are usable to edit the parameters listed on the right side of the screen.

FIG. 48 is a screen shot of a vest program edit screen 800 that appears in window 428 when the edit button 790 on the vest program screen 780 is selected. Listed on the upper right side of the screen 800 in a set of text boxes are air pulse generator settings, which correspond to the air pulse generator settings on the upper right side of the screen 780. Depending upon which mode button 784, 786, 788 is highlighted or selected at the time that edit button 790 is selected, certain ones of the text boxes on screen 800 are grayed and are not editable if they are not applicable to the mode associated with the selected button 784, 786, 788. For example, if "normal" button 784 is highlighted when edit button 790 is selected, then the "freq (end)," "pres (end)" and "time (ramp)" text boxes are grayed out because these parameters are not applicable to the normal mode of HFCWO therapy operation.

The left side of the screen 800 includes a plurality of numerical keys 802 for editing the air pulse generator settings associated with the various text boxes on the right side of screen 800. Also included on the left side of the screen 800 are a scroll down key 804 and back and forward space keys 806, 808. The scroll down key 804 is used to select the text box associated with the air pulse generator setting that is to be edited. Once a particular text box is selected for editing, appropriate presses of keys 802, 806, 808 changes the information in the selected text box. Located in the lower right corner of the screen 800 are save and cancel keys 810, 812. Pressing save key 810 causes the air pulse generator settings in the text boxes of screen 800 to be saved in memory of system 300 for the mode being edited with the changes made thereto, whereas pressing cancel key 812 cancels the changes made to the patient data in the text boxes of screen 800 such that the previous air pulse generator settings prior to any of the changes being made is saved in memory of system 300 for the respective mode.

Figure 49:
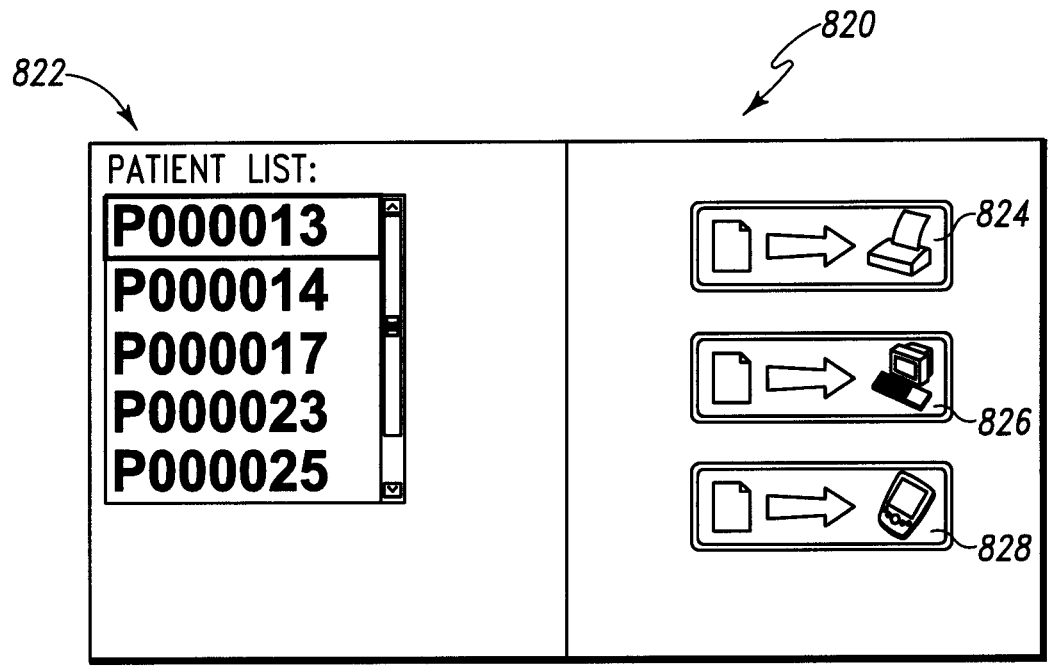
FIG. 49 is a screen shot of a data transmission screen of the system of FIGS. 12-15 showing buttons on the left side of the screen that are usable to initiate a data transmission from the system to a printer, a computer, or a portable wireless device.
Figure 50:
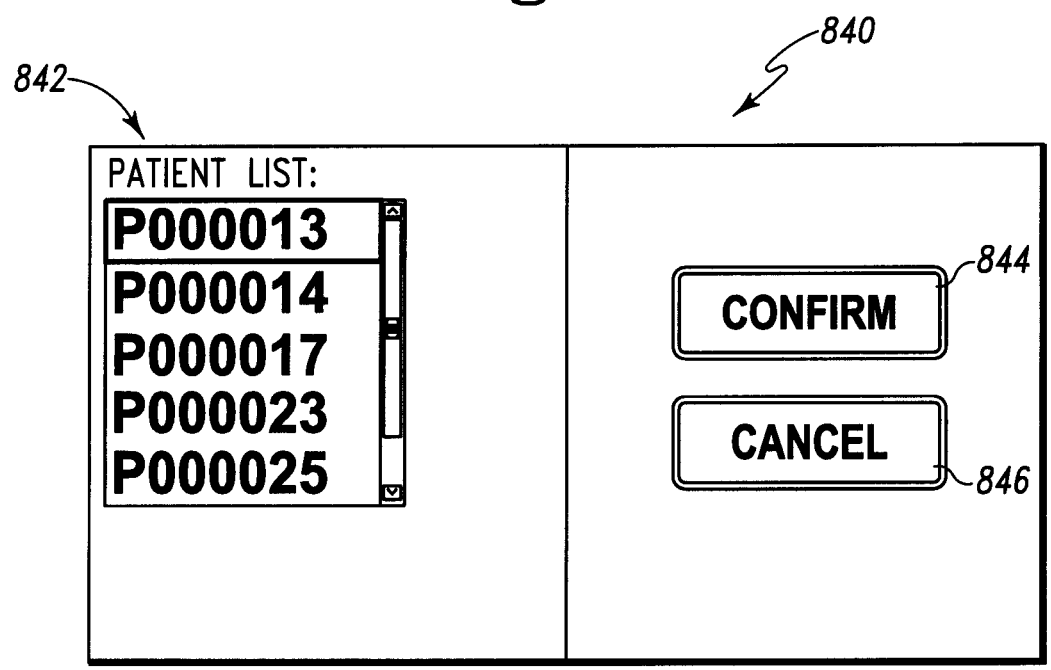
FIG. 50 is a screen shot of a data transmission confirm screen of the system of FIGS. 12-15 showing buttons that are usable to confirm or to cancel the data transmission.

FIG. 49 is a screen shot of a data download screen 820 that appears in the window 428 in response to the data download icon 404 being selected. On the left side of the data download screen 820 is a patient list 822, which lists the patient ID numbers. In some embodiments, a particular patient is selected by touching the patient ID number on screen 820. On the right side of the data download screen 820 are a printer button 824, a PC button 826 and a portable wireless device button 828. Buttons 824, 826, 828 are pressed to initiate a data transfer of a patient's data (e.g., date and time of therapy sessions provided to the patient by system 300, types of therapy delivered to the patient by system 300, the settings of the various parameters associated with the therapy sessions, the data associated with any tests or assessments of the patient made by system 300 including graphs and tables of such data, and patient information stored in system 300) to a printer, a computer, or a portable wireless device, respectively. In response to one of buttons 824, 826, 828 being pressed, a data download confirm screen 840 that appears in window 428 as shown in FIG. 50. On the left side of the data download confirm screen 840 is a patient list 842 that corresponds to the patient list 822 on the screen 820. On the right side of the data download confirm screen 840 are confirm and cancel buttons 844, 846. In the some embodiments, the data transferred by system 300 is wirelessly transmitted to an associated device, such as a printer, a PC or a PDA, when confirm button 844 on the data download confirm screen 840 is selected. In some embodiments, the data stored in the system 300 is transmitted over wires to an associated device coupled to system 300. Additionally or alternatively, system 300 may be coupled either wirelessly and/or via wires to a network of computer devices, such as local area network (LAN), a wide area network (WAN), an Ethernet of a healthcare facility, or the Internet, and a destination ID may be programmed into system 300 or entered by user to specify a device of the network to which the data is to be transmitted from system 300.

Figure 51:
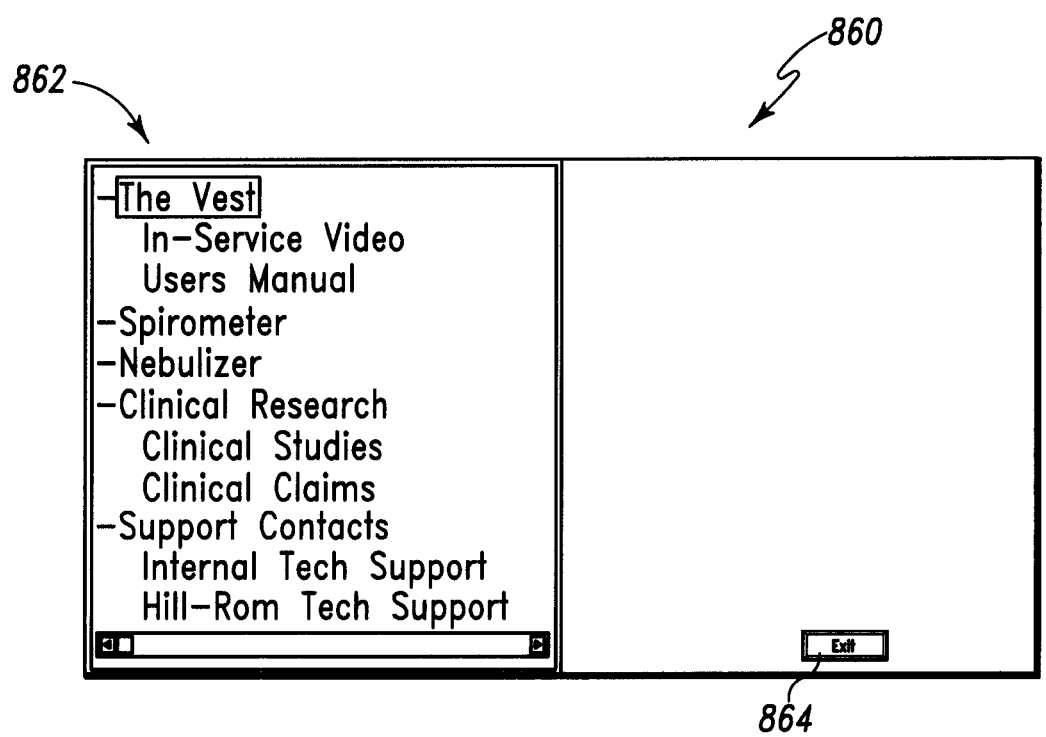
FIG. 51 is a screen shot of a help screen of the system of FIGS. 12-15 showing a list of the various portions of the system for which information is stored in the system to assist user to learn about the operation of the system.

FIG. 51 is a screen shot of a help screen 860 that appears in the window 428 in response to the help icon 406 being selected. On the left side of the help screen 860 is a help topic list 862. In the illustrated embodiment, the help list 862 lists the following topics: vest in-service video, vest user manual, spirometer, nebulizer, clinical research studies, clinical research claims, internal tech support, and manufacturer tech support. As the names of these various topics suggest, one or more of the memory devices associated with controller 318 of system 300 stores video clips, text and images of manuals, data regarding clinical studies, and other information that a user of system 300 may find useful in connection with learning how to set up and operate the various therapies of system 300, as well as learning about other aspects of system 300. Thus, in response to a user touching a particular topic on list 862, system 300 responds by showing on the right side of screen 860 an associated video clip, a users manual, information about other listed therapies (e.g., spirometer and nebulizer), view information about clinical studies and claims, and access internal and manufacturer technical support contact information. In the lower left corner of the help screen 860 is an exit button 864 that when presses, results in the video clip, users manual, or other information no longer being displayed on the right side of screen 860. Having video, manuals, contact information, and other information stored in the memory devices of system 300 results in this information being available to caregivers before, during, or after use of system 300 and is an improvement over prior art therapy devices in which hard copies of manuals or other materials and separate video tapes or discs are provided with the device because such separate pieces of media and information may be easily misplaced or lost.

Figure 24:
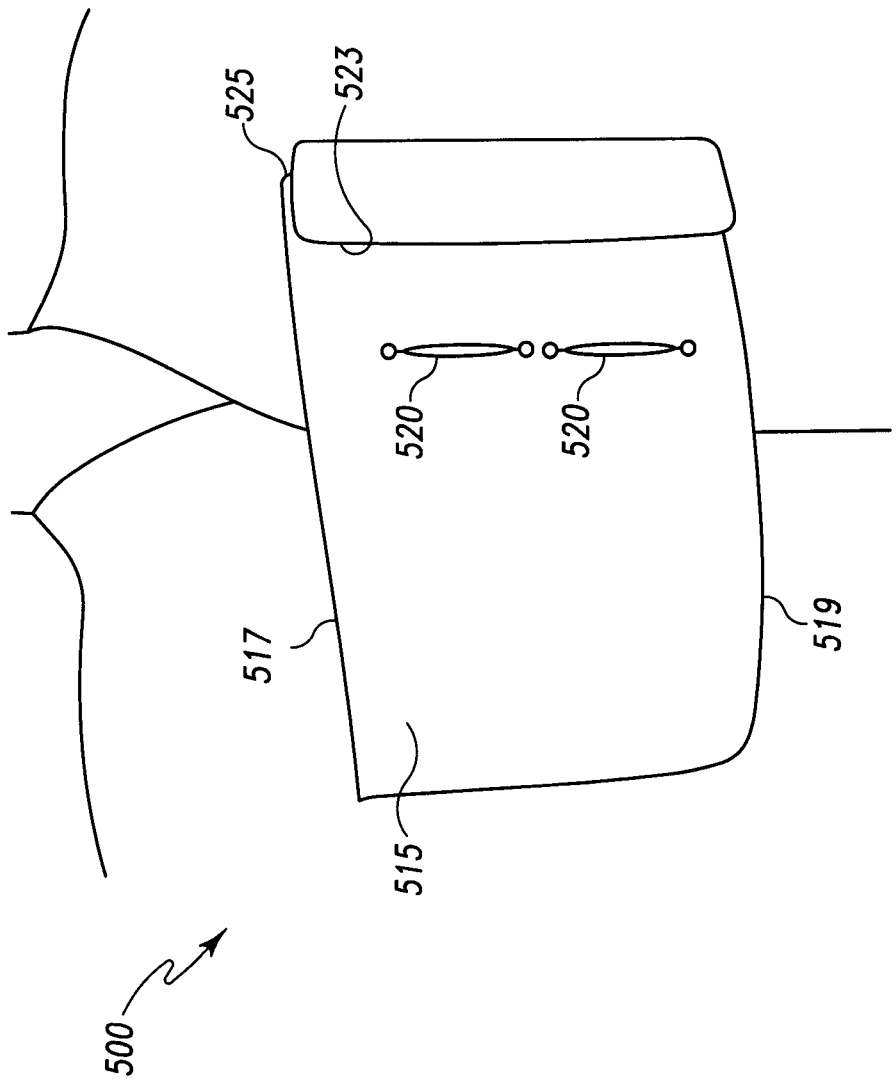
FIG. 24 is a perspective view showing a wrap vest having slits in which tubes may be inserted.

Referring now to FIGS. 24-40 a plurality of garments are shown which are suitable for use with each of the above-described HFCWO therapy systems 100, 200, 300. A wrap 500 having substantially straight upper and lower edges 517, 519 is constructed from inner and outer layers 515 of material which have substantially the same size and shape as shown in FIG. 24 (only the outer layer 515 can be seen in FIG. 24). The outer and inner layers 515 of material are generally elongated rectangular pieces of material that have generally vertical end edges 523, 525 and that are sealed to each other about the peripheries thereof in any suitable manner, such as by stitching, sewing, adhering, gluing, bonding, sonic or radio frequency (RF) welding, heat welding, or the like. Alternatively or additionally, some or all of the periphery of the inner and outer layers of material may be coupled together by zippers or other fasteners, such as hook-and-loop fasteners, buttons, snaps, clasps, and the like.

In the illustrative embodiment, the majority of the space between layers 515 is open and a pair of parallel slits 520 are formed in outer layer 515. Slits 520 are sized and configured to receive therein a pair of hoses such as hoses 118 of system 100, hoses 262 of system 200 or hoses 317 of system 300. Slits 520 are oriented generally vertically when wrap 500 is worn by a patient, with one of slits 520 being spaced vertically above the other of slits 520. Additional details regarding the geometry of slits 520 and the manner in which hoses are inserted through slits 520 can be found in U.S. patent application Ser. No. 10/657,728 which published as U.S. Patent Application Publication No. 2005/0054956 A1 on Mar. 10, 2005 and which is hereby incorporated by reference herein.

In some embodiments, layers 515 serve as an air bladder that receives the oscillating pressurized air from systems 100, 200, 300 and in other embodiments, a separate air bladder is retained between layers 515, with the separate air bladder having slits that are in registry with slits 520 so that the hoses inserted through slits 520 of the outer layer 515 also are inserted through the associated slits of the separate air bladder. In some embodiments, layers 515 may be tacked together, such as by welding, stitching, riveting, buttoning, or the like, at intermittent locations to prevent excessive ballooning of wrap 500 when inflated. Tacking at some or all of the intermittent locations may be done by internal tethers, such as stings, straps, bands, and the like, and such tethers may be of the same length between layers 515 or may be different lengths at different locations within wrap 500. In embodiments, having a separate air bladder between the layers 515, the separate air bladder may be tacked together at intermittent locations. Wrap 500 has suitable fasteners, such as hook-and-loop material (e.g., VELCRO® material) at appropriate locations, such as the end region of one of the ends of inner layer 515 and the end region of an opposite end of the outer layer 515, which couple together to retain wrap 500 on the patient. Other suitable fasteners, such as buckles, clips, clasps, straps, ties, buttons, and the like, may be used to retain wrap 500 on a patient in other embodiments.

When not used for HFCWO therapy, wrap 500 may remain on a patient if desired. Because less surface area of a patient's torso is covered by wrap 500 than is covered by prior art vest-like garments, the patient experiences less discomfort when continuing to wear wrap 500 after HFCWO therapy than when wearing the vest-like garments of the prior art. In addition, wrap 500 lies substantially flat against the patient's torso when not being used for HFCWO thereby reducing the bulkiness of the garment beneath a patient's shirt or hospital gown, for example. Some prior art vest-like garments have rigid hose connection ports extending outwardly from the garment which prevent these sorts of garments from being worn beneath a patient's shirt or gown without the shirt or gown having a noticeable hump or protrusion. In addition, the simple shape of wrap 500 allows wrap to be more easily placed on a patient than some prior art vest-like garments having arm holes, shoulder straps, front and rear vest panels with multiple flaps and straps that need to be coupled together, and the like. For an incapacitated patient, therefore, wrap 500 is much easier for a caregiver to place on a patient than a vest-like garment. In addition, due to its relatively small size as compared to prior art vest-like garments, wrap 500 is less apt to interfere with various tubes and lines, such as EKG lines, endotracheal tubes, ventilator tubes, and the like, thereby allowing these tubes and lines to remain coupled to the patient whereas use of some of the prior art vest-like garments may require repositioning, removal, or disconnection of some or all of these tubes and lines from the patient.

Figure 25:
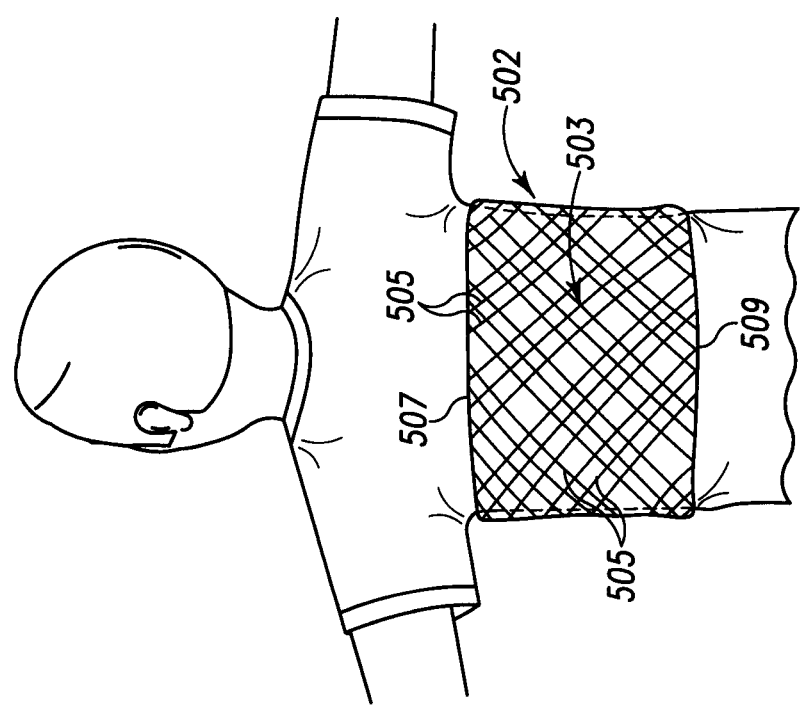
FIG. 25 is a perspective view showing a mesh wrap.

Referring now to FIG. 25, a mesh wrap 502 comprises a breathable double layer 503 constructed of a mesh or perforated fabric to minimize perspiration and to keep the patient cooler during HFCWO therapy. In the illustrative example, wrap 502 has substantially straight upper and lower edges 507, 509 with strands 505 of each mesh layer 503 extending at generally 45° angles relative to edges 507, 509. Strands 505 of each layer 503 are woven and are oriented such that the strands which cross each other do so at generally right angles (e.g., 90°). The outer and inner layers 503 of material are generally elongated rectangular pieces of material that are sealed to each other about the peripheries thereof in any suitable manner, such as use of beading or piping that is either welded (e.g., RF or sonic or heat welding) or use of relatively thin strips of material that is stitched or sewn in a manner that captures strands 505 within the strips. Such strips may be folded over such that the fold defines edges 507, 509 with the ends of strands 505 received within the fold.

Wrap 502 comprises an inflatable bladder that is situated between layers 503 and that is inflatable to deliver HFCWO therapy to the patient. Thus, a releasable fastener, such as a zipper or hook-and-loop fastener strips or buttons or the like may be provided along a portion of one of edges 507, 509 to allow for insertion of and removal of the inflatable bladder between layers 503. The inflatable bladder is sized to cover the front and, if desired, the sides of the patient. One or more suitable ports are provided for connection of hoses to the inflatable bladder. The one or more ports may protrude from the bladder between associated ones of the strands 505 which are diverted around the protruding port or ports. In other embodiments, flanges or other connection structure may be provided around the end of the one or ports and certain one of the strands 505 may terminate at and be connected to such connection structure of the one or more ports. For example, the connection structure may be a plastics material that is molded around the ends of the associated strands 505. In such embodiments, the inflatable bladder may not be removable from between layers 503 although, they could be if suitable detachable couplers are provided between the one or more bladder inlets and the one or more ports just described. Suitable fasteners, such as those listed above in connection with wrap 500, are provided at the end regions of wrap 502 for connection to each other to retain wrap 502 on the patient.

In alternative embodiments, a single mesh layer 503 is provided in the back region and possibly the side regions of the wrap 502 and fabric layers similar to layers 515 of wrap 500 are provided in the front region and possibly the side regions of wrap 502. In such embodiments, the mesh layer 503 and the fabric layers may be coupled together along a seam located near one of the side regions of the wrap and releasable fasteners that couple the mesh layer to the fabric layers near the other of the side regions of the wrap. Thus, in such embodiments, the front half (including some or all of the side regions of the wrap) is constructed like wrap 500 and the back half (including some or all of the side regions of the wrap) are constructed like wrap 502, but with only a single mesh layer 503.

Figure 26:
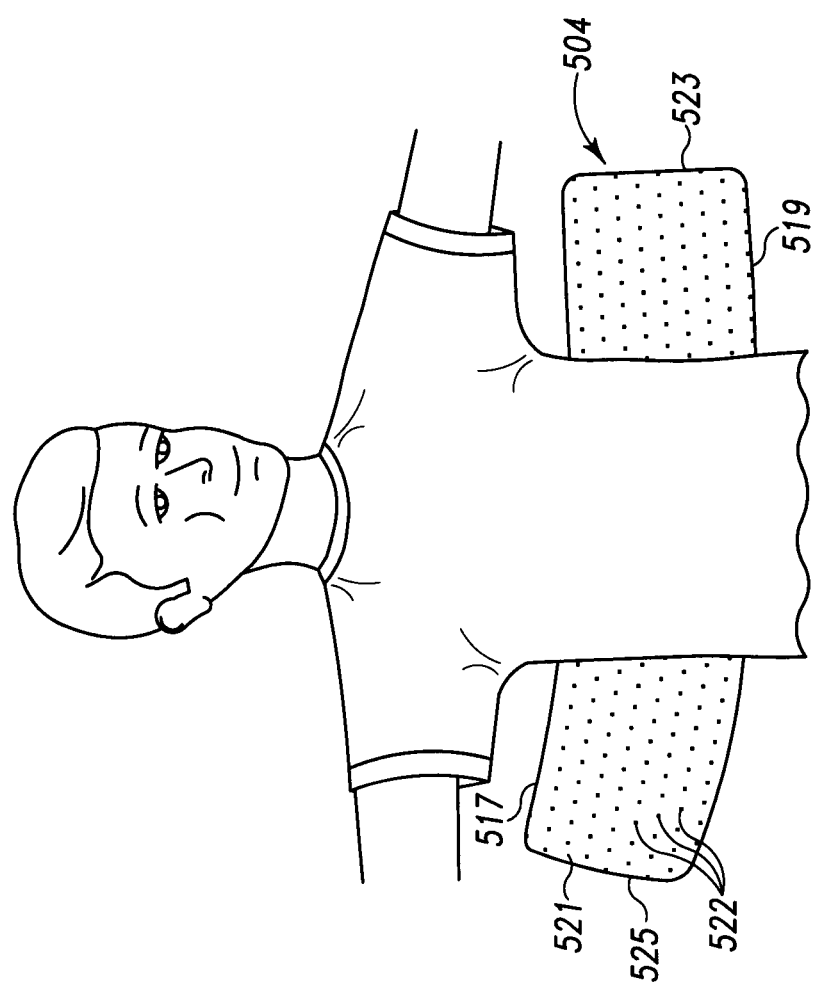
FIG. 26 is a perspective view showing a low air loss wrap.

Referring now to FIG. 26, a low air loss wrap 504 comprises a patient-facing inner layer 521 of material having a plurality of perforations 522 through which pressurized air is expelled to enhance the evaporation of any moisture, such as perspiration, thereby to promote cooling of the patient during HFCWO therapy. The outer layer of wrap 504 is substantially the same as the outer layer 515 of wrap 500. Thus, the layers of wrap 504 are substantially rectangular in shape having straight upper and lower edges 517, 519 as was the case with wrap 500. Wrap 504 has substantially straight left and right vertical edges 523, 525 as shown in FIG. 26.

The inner and outer layers of wrap 504 are coupled together about their peripheries in any of the manners described above in connection with wrap 500. In addition, any of the fasteners described above in connection with retention of wrap 500 on the patient may be provided to retain wrap 504 on the patient. Wrap 504 may have slits similar to slits 520 of wrap 500 or may have one or more ports that protrude from the outer layer for connection of hoses thereto. The layers or wrap 504 may also be tacked together at intermittent locations, such as midway between various ones of perforations 522, in any of the manners described above in connection with wrap 500. In some embodiments, the spacing between perforations may vary such that the number of perforations in any given area (e.g., number of perforations per square inch or square foot or square centimeter) is different. For example, there may be a greater density of perforations adjacent to the upper and lower edges 517, 519 of wrap 504 than in the middle region of wrap 504 between edges 517, 519, or vice versa. In some embodiments, a greater density of perforations may be provided in the back region and/or side regions of wrap 504 than in the front region, or vice versa.

Figure 27:
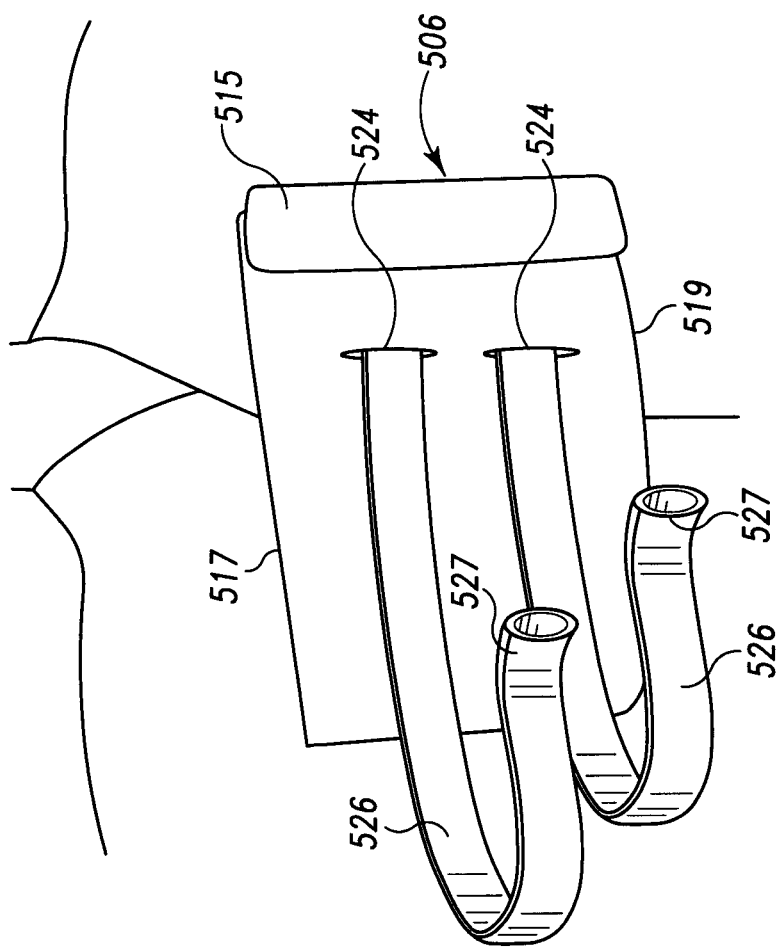
FIG. 27 is a perspective view showing a wrap with integrated flat tubing.

Referring now to FIG. 27, a wrap 506 has flat tubing 526 integrated therewith. Wrap 506 is constructed similarly to wrap 500 discussed above. Therefore, like reference numerals are used to denote portions of wrap 506 that are substantially the same as like portions of wrap 500. Wrap 506 has a pair of parallel slits 524 through which respective flat tubes 526 are routed. In some embodiments, tubes 526 connect to an associated inflatable bladder that is situated between layers 515 of wrap 506. In other embodiments in which the layers 515 themselves serve as an inflatable bladder, the ends of tubes 526 in the space between layers 515 are coupled in a suitable manner to the outer layer 515 in the region surrounding slits 524. Such coupling of tubes 526 to layer 515 may be accomplished by adhering, bonding, gluing, welding (RF or sonic or heat), or by sewing or stitching, for example.

It is contemplated by this disclosure that, in some embodiments, the ends of tubes 526 have outwardly extending flanges that are coupled to the interior surface of out layer 515 adjacent to slits 524. In other embodiments, such flanges are coupled to the exterior surface of outer layer 515. In still other embodiments, layer 515 may comprises multiple sheets or layers of material and the flanges at the ends of tubes 526 may be situated between two sheets of such a multi-sheet layer 515. It is also within the scope of this disclosure for tubes 526 to be coupled to wrap 506 by a separate coupler, such as ring of material to which tubes 526 couple and that couples to outer layer 515.

Based on the foregoing, it will be appreciated that tubes 526 remain permanently connected to the wrap 506 which reduces the potential for losing or misplacing the tubes 526. In addition, the flat tubes 526 occupy less storage space than other tubes disclosed herein which do not collapse into a flat configuration when not in use. Tubes 526 and wrap 506 may be rolled up or folded together for storage.

In use, tubes 526 inflate at least to some extent due to the associated air pulses being communicated therethrough by the associated system 100, 200, 300 with which wrap 506 is used. In some embodiments, tubes 526 are made of a material having suitable thickness and rigidity, but yet are still sufficiently flexible, to permit a caregiver to squeeze or deform the respective distal end regions 527 of tubes 526 into a substantially cylindrical shape for insertion into the ports 112, 260, 334 of the associated system 100, 200, 300 with a slight press fit between end regions 527 and the material defining the cylindrically shaped ports 112, 260, 334. In other embodiments, tubes 526 are made of a more flimsy material and adapters, such as fairly rigid and hollow cylinders, are provided for insertion into end regions 527 of tubes 526 and for insertion into ports 112, 260, 334 of the respective system 100, 200, 300. Each of such adapters, therefore, may extend partially into the associated tube 526 and partially into the associated port 112, 260, 334. In addition, such adapters may have barbs or annular ribs therearound to enhance the retention of tubes 526 on the adapters.

Figure 28:
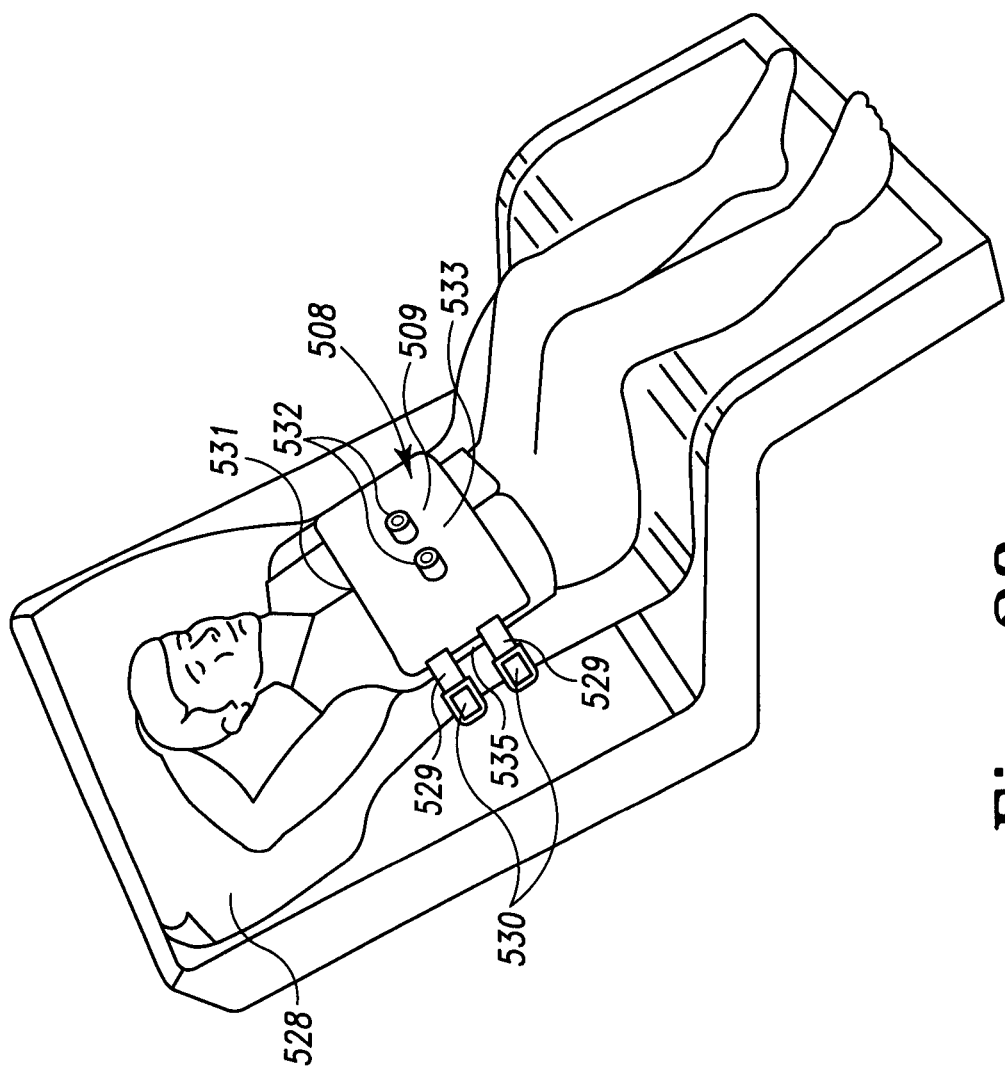
FIG. 28 is a perspective view showing a sheet clamped wrap couplable to a sheet underlying a patient.

Referring now to FIG. 28, a sheet clamped garment 508 wraps around the front and at least a portion of the sides of a patient but does not extend over the patients back. Thus, the patient does not need to be moved to place garment 508 on the patient for use. Garment 508 includes inner and outer layers 509 of material that are generally rectangular in shape and that are fastened together about the peripheries thereof in any of the manners described above in connection with wrap 500. Thus, garment 509 has generally straight upper and lower edges 531, 533 and generally straight side edges 535, only one of which can be seen in FIG. 28. Ports 532 protrude from the outer layer 509 and are configured for connection to tubes or hoses that are, in turn, coupled to the ports 112, 260, 334 of the associated system 100, 200, 300. In the illustrative example, ports 532 are positioned side-by-side such that one of ports 532 is spaced horizontally from the other of ports 532. In alternative embodiments, ports 532 are omitted and garment 508 has slits similar to slits 520 described above in connection with wrap 500.

The opposite ends of the garment 508 have respective pairs of tethers or straps 529 extending therefrom as shown in FIG. 28. Straps 529 may be coupled to layers 509 in any suitable manner such as stitching or riveting or RF welding, for example. In such embodiments, the end regions of straps 529 proximal to layers 509 may be situated between the inner and outer layers 509 and fastened thereto during the same fastening procedure, such as stitching or welding, that layers 509 are fastened to each other. In some embodiments, buckles or other releasable fasteners may couple straps 529 to layers 509 thereby providing adjustably to the amount that straps 529 extend away from layers 509 so that patients of different sizes may be accommodated.

A clamp 530 is coupled to each of straps 529 and each clamp 530 is configured to grip a sheet 528 which underlies the patient. The straps 529 and/or clamps 530 are adjustable so that garment 508 may be held tightly against the patient. In some embodiments, therefore, free ends of straps 529 extend beyond clamps 530 and may be pulled by a caregiver to tighten garment 508 in place relative to the patient. In other embodiments, straps 529 are elastic and are stretched before clamps 530 are coupled to the sheet 528 underlying the patient such that the elasticity of the straps 529 stretched in this manner exerts a force on the layers 509 of garment 508 which retains garment 508 in place on the patient. The sides of sheet 528 may be bunched up prior to coupling clamps 530 to the bunched up portion of the sheet 528. In addition, clamps 530 each have members, such as jaws, clam shell members, cams, or the like, that are manipulatable between a gripping position to firmly grip the sheet 528 between such members of the associated clamp 530 and a releasing positions to allow the sheet 528 to be inserted into or removed from the associated clamp 530.

Figure 29:
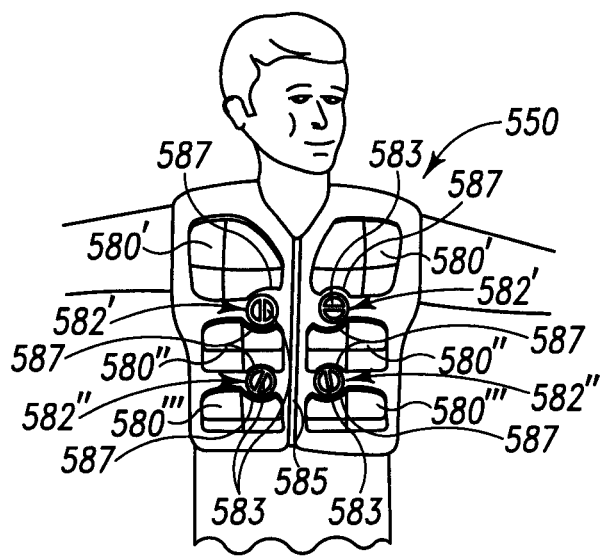
FIG. 29 is a perspective view showing a vest having a plurality of air chambers and a set of valves having knobs that are manipulated to open and close associated ones of the air chambers.
Figure 30:
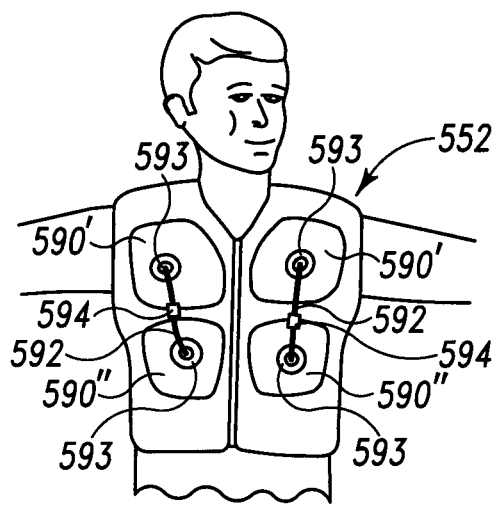
FIG. 30 is a perspective view showing a vest having a plurality of air chambers, a set of hose extending between respective air chambers, and a set of hose clamps coupled to respective hoses.
Figure 31:
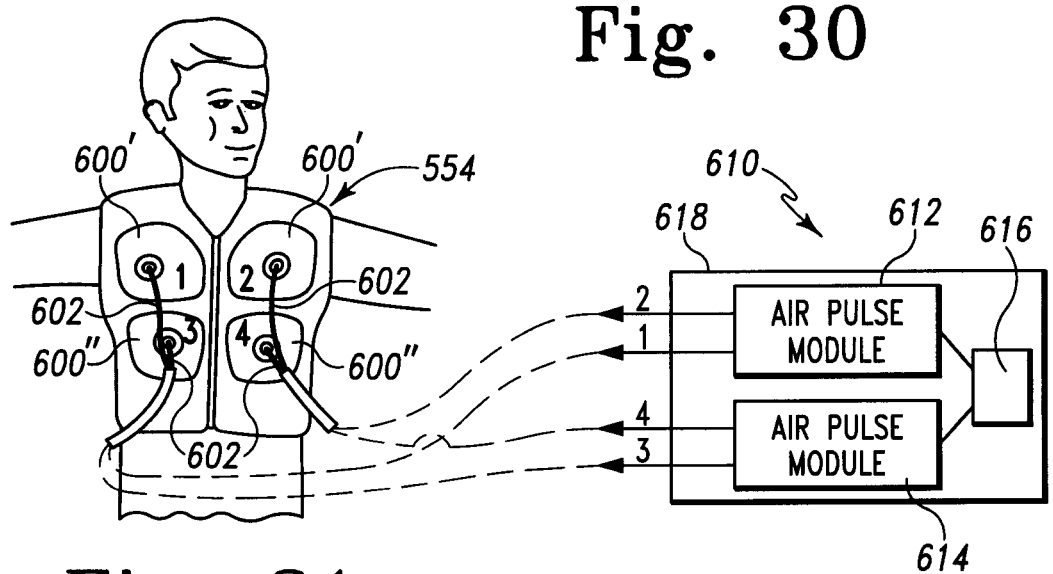
FIG. 31 is partly a perspective view and is partly a diagrammatic view of a system including a vest having a plurality of air chambers and an air pulse generator that is operable to deliver a first oscillating pressure to first and second air chambers of the vest and to deliver a second oscillating pressure to third and fourth air chambers of the vest.

Garments 550, 552, 554 shown in FIGS. 29-31, respectively, each have multiple air chambers that permit customization of HFCWO therapy for individual patients. Illustrative garments 550, 552, 554 are vests and therefore, are referred to in the following description as vests 550, 552, 554, respectively. However, the features of vests 550, 552, 554 may be employed in other garments such as any of wraps discussed above or apron-like garments discussed below. Vest 550 shown in FIG. 29 has multiple bladders 580', 580", 580'"

defining air chambers that are grouped into left and right pairs with the chambers of each pair being positioned generally over the upper, middle, and lower lobes of the patients lungs, respectively.

In the illustrative example of vest 550, upper bladders 580' receive pressurized air from the associated system 100, 200, 300 to which vest 550 is coupled. Although not illustrated, a port or slit (similar to any of those discussed above in connection with other garment embodiments) for coupling bladders 580' to the associated system 100, 200, 300 is provided on each of bladders 580' or elsewhere on vest 550. If provided elsewhere on vest 550, conduits internal to vest 550 are routed to bladders 580' and also to bladders 580", 580''' from the respective ports or slits. Vest 550 has a zipper 585 or other suitable releasable fastener, such as hook-and-loop fasteners, straps, buckles, buttons, or the like, for closing the left and right front flaps of vest 550 in front of the patient. In the illustrative embodiment, zipper 585 is positioned along a midline of the front of the patient.

Vest 550 has a plurality of flow regulators 582', 582" that can be selectively activated or deactivated to control the provision of oscillatory pressure to associated bladders 580", 580'''. Illustratively, flow regulators 582', 582" each have associated knobs 583 that are accessible on the exterior of vest 550 and that are coupled to respective valves (not shown) that are situated in the respective pneumatic flow paths from chambers 580", 580''' to the air pulse generator (not shown) of the respective system 100, 200, 300 to which vest 550 is coupled. Knobs 583 are turned to vary an orifice of the corresponding valve thereby to adjust the amplitude and/or the baseline pressure of the oscillatory pressure that inflates the chambers of bladders 580", 580'''. Regulators 582', 582" may be adjusted, therefore, between fully opened and fully closed positions and set at any number, including an infinite number in some embodiments, of intermediate positions between the fully opened and fully closed positions. In the illustrative embodiment, each bladder 580', 580", 580''' has a cutout 587 to accommodate a portion of an associated one of knobs 583.

In some embodiments, knobs 583 and/or the associated valves have suitable locking mechanisms or detent mechanisms that prevent or resist knobs 583 and/or valves from inadvertently turning out of the chosen position during HFCWO therapy. For example, regulators 582', 582" may include mechanisms that bias knobs 583 outwardly away from vest 550 (or inwardly toward vest 550) such that knobs 583 need to be pushed inwardly towards vest 550 (or pulled outwardly away from vest 550) to unlock the knobs 583 for turning. In other embodiments, knobs 583 may each have one or more buttons that need to be squeezed or pressed before knobs 583 are unlocked for turning. If detent mechanisms are provided in regulators 582', 582", such detent mechanisms are fashioned such that a user is able to rotatably index knobs 583 from one setting to another by application of a sufficient amount of torque to knobs 583, but the detent mechanisms have sufficient holding or resistive force that knobs 583 don't inadvertently index from one setting to another in response to the vibratory or shaking forces to which vest 550 is subjected during HFCWO therapy.

In the illustrative example, the chambers of bladders 580' are inflated with oscillating pressure as provided directly from the associated air pulse generator whereas, regulators 582', 582" are adjustable so that the chambers of bladders 580", 580''' may be inflated with a lesser baseline pressure and/or a lesser amplitude as compared to the chambers of bladders 580', if desired. In other embodiments, additional flow regulators are provided to enable adjustment of the oscillatory pressure reaching bladders 580' as well. In further embodiments, the oscillating pressure from the associated air pulse generator is communicated directly to the chambers of bladders 580''' and regulators 582' are associated with bladders 580' to permit adjustment of the baseline pressure and/or amplitude of the oscillatory pressure reaching the chambers of bladders 580'.

In some embodiments of vest 550 contemplated herein, bladders 580', 580", 580''' are connected in series such that regulators 582' are provided in the flow path between bladders 580' and bladders 580" and such that regulators 582" are provided in the flow path between bladders 580" and bladders 580'''. Assuming that bladders 580' are coupled directly to the source of oscillating pressure, the oscillatory pressure pulses reaching bladders 580" are received from associated bladders 580' through regulators 582' and the oscillatory pressure pulses reaching bladders 580''' are received from associated bladders 580" through regulators 582". In other embodiments, bladders 580", 580''' may be coupled to respective bladders 580' in parallel such that regulators 582' are provided in the flow path between bladders 580' and bladders 580" and such that regulators 582" are provided in the flow path between bladders 580' and bladders 580'''. In still other embodiments, if bladders 580" are coupled directly to the source of oscillating pressure, then bladders 580' and 580''' may be connected to bladders 580" in parallel such that the oscillatory pressure pulses reaching bladders 580' are received from associated bladders 580" through regulators 582' and such that the oscillatory pressure pulses reaching bladders 580''' are received from associated bladders 580" through regulators 582". It is also within the scope of this disclosure for bladders 580''' to receive pressure pulses directly from the source of oscillatory pressure and then communicate the pressure pulses upwardly to bladders 580', 580" through regulators 582', 582" either along serial or parallel flow paths.

The vest 552 shown in FIG. 30 has an upper pair of bladders 590' defining upper inflatable chambers and a lower pair of bladders 590" defining lower inflatable chambers. In some embodiments, bladders 590' are coupled to an air pulse generator, such as those of systems 100, 200, 300, using associated hoses 118, 262, 317, and in other embodiments, bladders 590" are coupled to an air pulse generator. Thus, vest 552 has suitable slits or ports (not shown, but similar to any of those described above) for connection of hoses which are routed to a source of oscillating pressure. A hose 592 extends between each upper bladder 590' and the associated bladder 590" therebelow. The ends of each hose 592 are coupled to a respective fitting 593, each of which protrudes from a respective bladder 590', 590". Thus, each bladder 590' is in pneumatic communication with an associated one of bladders 590" through corresponding hoses 592.

A flow regulator 594 is coupled to each tube 592 and is movable to open and close the flow passage through the tube 592 thereby to open and close pneumatic communication between bladders 590' and bladders 590". In the illustrative example, flow regulators 594 comprises tube clamps which are mounted to tubes 592 and which have fully opened and fully closed positions. Thus, illustrative hoses 592 are made of a material, such as rubber or silicone, which permits hoses 592 to collapse under the force of the tube clamps to close off the internal passage through hoses 592. In other embodiments, flow regulators 594 may have intermediate positions between the fully opened and fully closed positions, such as a tube clamps which only partially squeezes or collapses the associated tube 592. In some embodiments, vest 552 may have additional bladders, such as a third pair of bladders similar to vest 550, with additional hoses 592 and flow regulators 594 being provided between one or the other of bladders 590', 590" and an associated one of the additional bladders. In alternative embodiments, individual the chambers of bladders 590', 590" may be closed off by using press-and-seal material or a zip lock arrangement, similar to Saran™ press-and-seal wrap, either within a flow conduit between bladders 590', 590" or at the boundary where such flow conduits meets the chambers of respective bladders 590', 590".

Referring now to FIG. 31, a vest 554 has an upper pair of bladders 600' defining an uppers pair of inflatable chambers and a lower pair of bladders 600" defining a lower pair of inflatable chambers. Bladders 600', 600" are coupled by associated hoses 602 to an air pulse generator 610 which comprises a first air pulse module 612 and a second air pulse module 614. A fitting 603 couples one of the ends of each of hoses 602 to an associated bladder 600', 600". In the illustrative example, upper bladders 600' are coupled pneumatically to the first air pulse module 612 as indicated by numerals 1 and 2 on bladders 600" and numerals 1 and 2 adjacent arrows leading from module 612. Similarly, lower bladders 600" are coupled pneumatically to the second air pulse module 614 as indicated by numerals 3 and 4 on bladders 600" and numbers 3 and 4 adjacent arrows leading from module 614. Module 612 is operable independently of module 614 such that each module 612, 614 may operate according to different operating parameters, such as baseline pressure, frequency, and duration of operation. Thus, the intensity and frequency of oscillatory forces imparted on the patient by bladders 600' may be different than the intensity and frequency of oscillatory forces imparted on the patient by bladders 600".

As shown diagrammatically in FIG. 31, a common controller 616 commands the operation of modules 612, 614. In addition, modules 612, 614 and controller 616 may be housed in a common housing 618. Separate user inputs, such as separate fields of a touch screen display, may be provided for entry of the different operating parameters for modules 612, 614. If desired, however, modules 612, 614 may be programmed to operate in accordance with identical operating parameters. In other embodiments, separate controllers may be provided for each of modules 612, 614. Modules 612, 614 may be substantially similar to the dual-diaphragm air pulse modules described in U.S. Patent Application Serial No. 2004/0097842 which is already incorporated by reference herein. Of course, it is intended that air pulse modules of all types may be included in air pulse generator 610, including single diaphragm air pulse modules, piston type air pulse modules, valve type air pulse modules, and the like.

In the illustrative example, generator 610 is configured to provide pressure pulses to each of bladders 600' at a substantially identical baseline pressure and/or amplitude and to provide pressure pulses to each of bladders 600" at a substantially identical baseline pressure and/or amplitude. In alternative embodiments, a flow regulator, such as valve may be associated with any one or more of hoses 602 to permit adjustment of the baseline pressure and/or amplitude of the oscillating pressure reaching any particular one of the associated bladders 600', 600". Thus, in such embodiments, the pressure characteristics of the oscillatory pressure reaching each individual bladder 600', 600" may be unique and different than that of each of the other bladders 600', 600". Such flow regulators may be coupled to and/or housed within housing 618 and may be electronically controlled by controller 616. In still other embodiments, more than two air pulse modules may be provided in generator 610. For example, if four modules are provided, then each module may be operated at its own unique frequency such that the frequency of oscillating pressure reaching each of bladders 600', 600" is unique and different than that of each of the other bladders 600', 600" It is contemplated by this disclosure, therefore, that specific bladders 600', 600" of vest 554 can be inflated according to different pressure and frequency settings.

Figure 32:
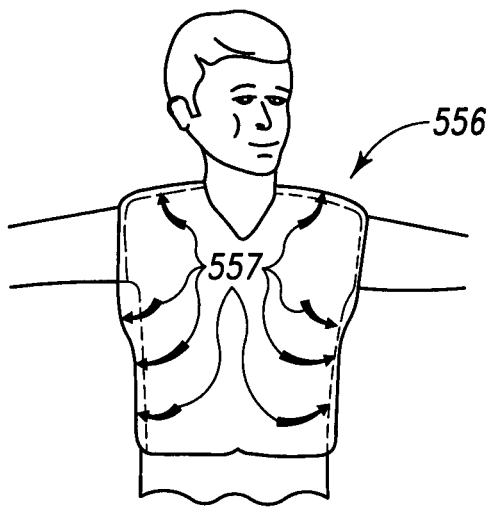
FIG. 32 is a perspective view showing a vest having an inner layer of material made from a wicking material.
Figure 33:
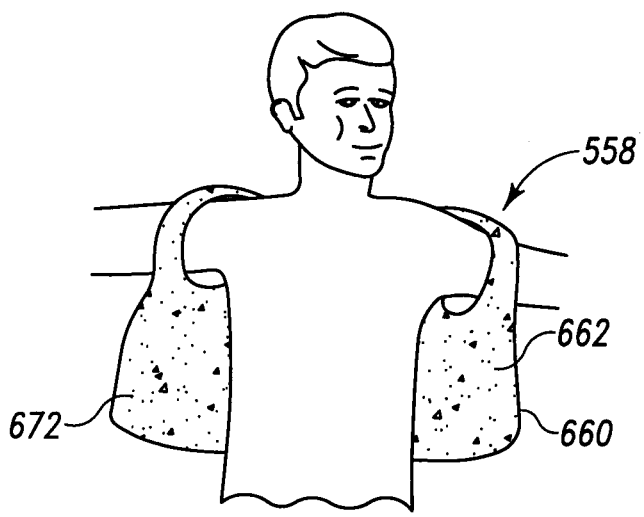
FIG. 33 is a perspective view showing a low air loss vest.
Figure 34:
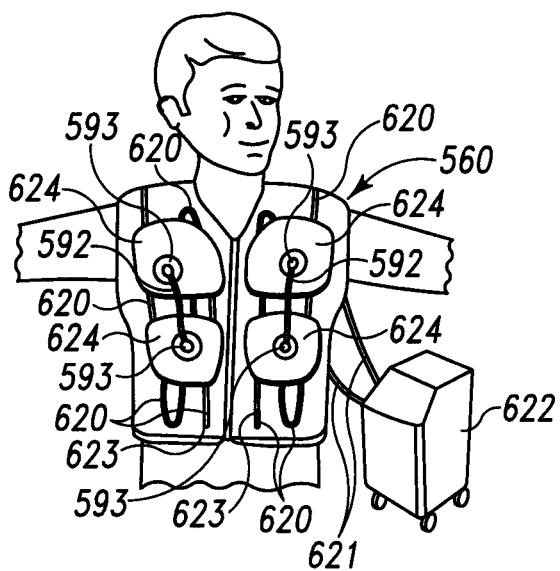
FIG. 34 is a perspective view showing a vest having a plurality of air chambers and cooling channels.

Vests 556, 558, 560, shown in FIGS. 32-34, are designed to promote patient ventilation and cooling. For example, an interior layer of the vest 556 shown in FIG. 32 is made of a wicking fabric to absorb moisture away from a patent's skin for evaporation into the inflatable chamber of vest 556 and then, for ultimate passage to the ambient surroundings through the exterior of vest 556 as indicated by arrows 557. Vest 556 has perforations or other holes or passageways through which pressurized air within the inflatable chamber of vest 556 escapes to the ambient surroundings. Such passageways may be created, for example, due to a stitching operation that fastens inner and outer layers of vest material together to form the inflatable chamber of vest 556. The thread which passes through the punctures formed in the layers of vest 556 by the associated needle of the stitching operation does not completely fill the needle punctures such that the needle punctures provide the passageways to the ambient surroundings. Additionally or alternatively, other discrete holes may be formed in the outer layer through which pressurized air is expelled from vest 556 to the ambient surrounding. The convective movement or flow of pressurized air through vest 556 enhances the evaporation of the moisture wicked through the interior layer of vest 556.

As shown in FIG. 33, an inner layer 660 of a low air loss vest 558 has a number of perforations 672 through which pressurized air is expelled to improve evaporation of moisture, such as perspiration, during HFCWO therapy. The inner and outer layers of vest 558 may also be tacked together at intermittent locations, such as midway between various ones of perforations 522, in any of the manners described above in connection with wrap 500, in order to prevent ballooning of vest 558 during inflation. In some embodiments, the spacing between perforations 672 may vary such that the number of perforations in any given area (e.g., number of perforations per square inch or square foot or square centimeter) is different. For example, there may be a greater density of perforations adjacent to neck, arm, and waist holes of vest 558 than in the middle region of vest 558, or vice versa. In some embodiments, a greater density of perforations may be provided in the back region and/or side regions of vest 558 than in the front region, or vice versa.

Referring now to FIG. 34, a vest 560 has one or more conduits or channels 620 through which cooling fluid is circulated to promote patient cooling. The cooling fluid may be either a cooled liquid or a cooled gas. In the illustrated embodiment, the cooling fluid is supplied by a cooling system 622, such as the Medi-Therm Hyper/Hypothermia System marketed by Gaymar Industries Inc. of Orchard Park, N.Y. The illustrative vest 560 shown in FIG. 34 has multiple bladders 624 defining chambers that receive oscillatory pressure for HFCWO therapy. In other embodiments, vest 560 has only a single inflatable chamber defined by inner and outer layers of vest material or defined by a single bladder situated between the inner and outer layers of vest material, although multiple chambers are not necessary for patient cooling. Vest 560 shown in FIG. 34 is similar to vest 552 shown in FIG. 30, in that vest 560 also has fittings 593 and hoses 592 for pneumatically coupling upper and lower bladders 624 to each other. Illustrative vest 560 does not have any flow regulators coupled to hoses 592 but, of course, flow regulators may be coupled to hoses 592 in other embodiments of vest 560 if desired.

Conduits 620 are routed through vest 560 along generally serpentine patterns with generally straight segments of the channels being oriented vertically (assuming the patient is standing as shown in FIG. 34) and with loops or curves of the conduits 620 being situated near the bottom and top of the vest 560. In other embodiments, conduits 620 may be routed through vest 560 along some other pattern, including a side-to-side serpentine pattern rather than the illustrative up-and-down serpentine pattern. Conduits 620 may be coupled to the exterior of vest 560 as shown in FIG. 34, or may be coupled to the interior of vest 560 or embedded between layers of vest material in other embodiments.

Conduits 620 may be separated into a left and a right conduit 620 with the right conduit 620 extending over the front and back of vest 560 on the right side thereof and the left conduit 620 extending over the front and back of vest 560 on the left side thereof. Each of conduits 620 may have a port which is configured to couple to ends of hoses 621 which extend from system 622. In the illustrative example of FIG. 34, two hoses 621 are shown with one hose 621 coupling to the right conduit 620 and the other hose coupling to the left conduit 620. Each conduit 620 may comprise dual lumens or passageways therethrough which interconnect adjacent terminal ends of respective conduits 620. Thus, cooling fluid from system 622 travels down one of the lumens of each conduit 620 toward the terminal end 623 thereof and then returns back to system 622 through the other of the lumens of conduit 620. In such embodiments, hoses 621 also have dual lumens with one lumen being a fluid delivery lumen and the other being a fluid return lumen.

In other embodiments, the left and right conduits 620 may have only a single lumen or passage therethrough with a connection port being provided at each end of such single-lumen conduits 620 such that one of the hose connection ports is an entry port that receives fluid from system 622 and the other of the hose connection ports is an exit port through which fluid is returned to system 622. In still other embodiments, vest 560 has a only a single conduit 620. For example, if a hose connection port for connection of hoses 621 is provided at each terminal end 623, then a fluid delivery hose 621 could be attached to one of the ports at the associated end 623 of conduit 620 and a fluid return hose 621 could be attached to the other of the ports at the other end 623 of conduit 620. In such embodiments, the roles of the fluid delivery and fluid exit ports may be reversed periodically, such that the direction of flow of cooling fluid through hoses 621 and conduit 620 is reversed periodically, so as to compensate for the fact that the cooling fluid heats up while traveling through conduit 620 and reversing which end 623 of conduit 620 initially receives the cooling fluid from system 622 results in alternating, from time to time, which side of the patient is exposed to the cooler fluid. Such a reversal of the direction of travel of the cooling fluid through conduit 620 is controlled by valves and other components internal to system 622 in these embodiments.

Backless apron-like configurations of garments 562, 564, 566 are shown in FIGS. 35-39 and are designed to enhance the ease with which these garments are placed on a patient. Garments 562, 564, 566 are sometimes referred to herein as aprons 562, 564, 566. Garments 562, 564, 566 can be secured to the patient by a single caregiver while the patient remains supine and relatively undisturbed, although some movement of the patient may be required. If desired, garments 562, 564, 566 may remain on a patient even when the patient is not undergoing HFCWO therapy. In the illustrative examples, no ports or slits for connection to hoses of systems 100, 200, 300 are shown, but it is to be understood that each of aprons 562, 564, 566 has such ports or slits through which oscillatory pressure is communicated to one or more inflatable bladders of each of aprons 562, 564, 566. Such one or more bladders of each of aprons 562, 564, 566 may be defined between layers of material of the respective apron or may be a separate bladder that is retained between the layers of material of the respective apron. Bladders that attach to a single apron layer (or a single wrap layer or a single vest layer), such as with snaps or the like, are also contemplated by this disclosure.

Referring to FIG. 35, apron 562 has a vest-like front appearance but is missing a back and a portion of each of the sides. Thus, unlike wrap 508, apron 562 has a portion that extends up and around the patient's neck and an inflatable bladder of apron 562 covers more of the front of the patient's torso than the inflatable bladder of wrap 508. On the opposite sides of apron 562 in the region of apron 562 between the patient's armpits and waist, a pair of straps or tethers 631 extend therefrom and a clamp 632 is coupled to each of straps 631. The discussion above of straps 529 of wrap 508, including the manner of attachment to the associated garment and the manner of attachment to the associated clamp, is equally applicable to straps 631 of apron 562. In addition, the discussion above clamps 530 of wrap 508 is equally applicable to clamps 632 of apron 562. Thus, straps 631 may be coupled to the material layers of apron 562 in any suitable manner such as stitching or riveting or RF welding, for example. In such embodiments, the proximal end regions of straps 631 may be situated between the inner and outer layers of apron 562 and fastened thereto during the same fastening procedure, such as stitching or welding, that the layers of apron 562 are fastened to each other. In some embodiments, buckles or other releasable fasteners may couple straps 631 to the bladder containing portion of apron 562 thereby providing adjustably to the amount that straps 631 extend away from the sides of apron 562 so that patients of different sizes may be accommodated.

Clamp 632 is coupled to each of straps 631 and each clamp 632 is configured to grip a sheet 630 which underlies the patient. The straps 631 and/or clamps 632 are adjustable so that garment 562 may be held tightly against the patient. In some embodiments, therefore, free ends of straps 631 extend beyond clamps 632 and may be pulled by a caregiver to tighten garment 562 in place relative to the patient. In other embodiments, straps 631 are elastic and are stretched before clamps 632 are coupled to the sheet 630 underlying the patient such that the elasticity of the straps 631 stretched in this manner exerts a force on the bladder-containing portion garment 562 which retains garment 562 in place on the patient. The sides of sheet 630 may be bunched up prior to coupling clamps 632 to the bunched up portion of the sheet 630. In addition, clamps 632 each have members, such as jaws, clam shell members, cams, or the like, that are manipulatable between a gripping position to firmly grip the sheet 630 between such members of the associated clamp 632 and a releasing positions to allow the sheet 630 to be inserted into or removed from the associated clamp 632.

Referring now to FIGS. 36 and 37, apron 564 has a front panel 647 including a generally straight bottom edge 649, a pair of shoulder flaps or coverings 648 that extend up and over the top of the patient's shoulders, and a concave upper edge 645 that dips downwardly relative to the upper most portion of shoulder flaps 648 to accommodate a patient's neck area. A pair of shoulder straps 640 each have an upper end coupled to a respective one of the shoulder flaps 648 and each have a lower end coupled to respective side region of front panel 647 below, and in spaced relation from, the associated upper end.

Thus, straps 640 cooperate with front panel 647 to form loops through which a patient's arms are passed to secure garment 564 on the patient.

In some embodiments, one of the ends, either the upper end or lower end, of each strap 640 are permanently fastened to front panel 647, such as by stitching, bonding, riveting, gluing, adhering, welding (sonic, RF, or heat), or the like, and the other end of each strap 640 is releasably fastened to front panel 647 by a suitable coupling mechanism such as, for example, buckles, clips, clasps, hook-and-loop fasteners, buttons, snaps, and the like. In other embodiments, both ends of straps 640 are permanently fastened to panel 647 or both ends of straps 640 are releasably fastened to front panel 646. Additionally or alternatively, the length of straps 640 may be adjusted via suitable adjusters, such as buckles, eyelets, or the like. For example, straps 640 may be permanently coupled to the sides of panel 647 at their lower ends and loop through an eyelet coupled to shoulder flaps 648 and then doubled back on themselves so that hook-and-loop patches on the straps 640 can intermesh to retain garment 564 on a patient.

When the one or more bladders of garment 564 are inflatably pulsed during HFCWO therapy of the associated patient, it will be appreciated that the shoulder straps 640 in cooperation with shoulder flaps 648 prevent the upper region of front panel 647 from expanding, in any appreciable sense, away from the patient, thereby enhancing and concentrating the oscillatory forces imparted on the patient in the upper chest area as compared to the lower chest area in which front panel 647 is able to move away from the patient to a greater extent. In other embodiments, a back or waist strap may extend around the patient's waist from one side of the bottom region of front panel 647 to the other to prevent or reduce the movement of the bottom region of front panel 647 away from the patient during HFCWO therapy. Such a waist strap may be coupled to front panel 647 in any of the manners described above in connection with straps 640 and therefore, may have any of the above-described permanent fasteners, releasable fasteners, and length adjusters. In some embodiments, the shoulder straps 640 and/or waist straps used for securing garment 564 on a patient may be provided with graduated markings to aid in repeated fittings of apron 564 on the same patient.

Figure 38:
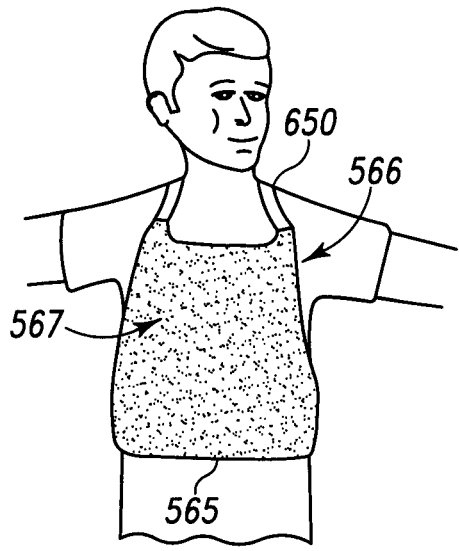
FIG. 38 is a front perspective views showing an apron-like garment.
Figure 39:
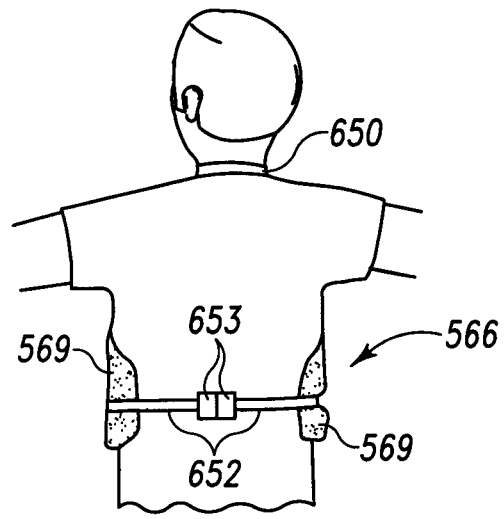
FIG. 39 is a rear perspective view of the garment of FIG. 37 showing a neck strap and a torso strap.

Referring now to FIGS. 38 and 39, apron 566 comprises a front panel 567 with a generally straight bottom edge 565, a neck strap 650 extending from one side of an upper region of panel 567 to another to form a loop through which the patient's head is passed, and a pair of back straps 652 which couple together to secure apron 566 on the patient. Furthermore, front panel 567 has side flaps 569 that extend around the sides of the torso of the patient beneath the patient's armpits. Both ends of strap 650 are permanently fastened to panel 567 in any of the manners described above in connection with straps 640 of garment 564. Similarly, one end of each back strap 652 is permanently fastened to a respective one of side flaps 569. Suitable couplers 653 are mounted to each strap 653 and are configured to mate together. Such couplers 653 may comprise, for example, buckles having interlocking members, such as flexible fingers received in pockets, or the like. In some embodiments, one or both straps are routed through couplers 653 such that a free end of one or both straps 652 may be pulled to tighten straps 652 and panel 567 on the patient. In some embodiments of apron 566, the back straps 652 may be provided with graduated markings to aid in repeated fittings of garment 566 on the same patient.

Figure 40:
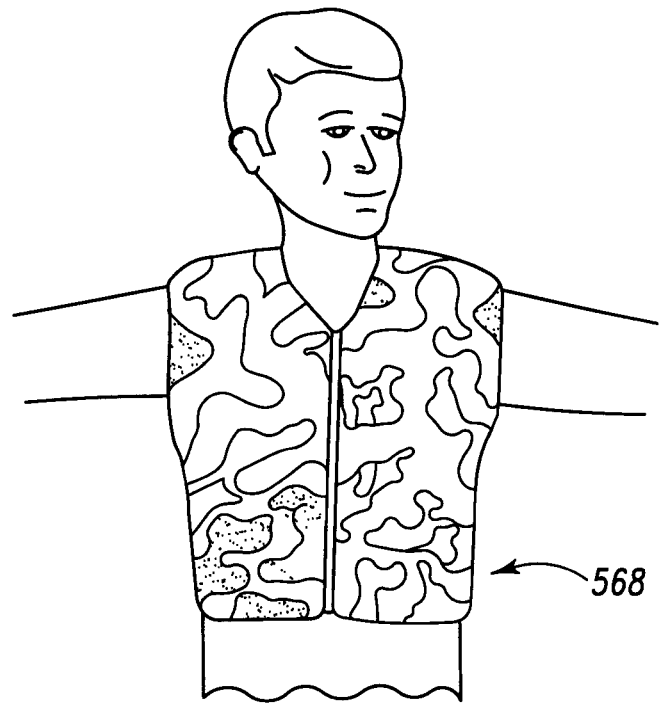
FIG. 40 is a perspective view showing a vest made from clinical camouflage material.

Referring now to FIG. 40, a vest 568 is manufactured from clinical camouflage fabric which hides stains. The clinical camouflage fabric is impregnated with activated charcoal and/or antimicrobial agent to inhibit odors and/or bacterial growth. The interior and exterior layers of vest 568 may comprise such clinical camouflage fabric. Additional layers of material of other types may be laminated to each of the clinical camouflage layers included in vest 568, if desired. It should be understood that any of the garments disclosed herein (i.e., the wraps 500, 502, 504, 506, 508, vests 550, 552, 554, 556, 558, 560, 568, and aprons 562, 564, 566 discussed above) may have one or more layers comprising a clinical camouflage material, if desired.

All permutations and variations of features described above in each garment embodiment are intended to be applicable to each of the other garment embodiments, such that features may be mixed and matched to create additional embodiments in accordance with this disclosure. For example, aprons 562, 564, 566 may include multiple bladders with associated flow regulators of the type included in vests 550, 552, 554; wraps 500, 502, 504, 506, 508 may have an interior layer made from wicking material of the type included in vest 556; wraps 500, 502, 504, 506, 508 and aprons 562, 564, 566 may have cooling conduits for receipt of a cooling fluid from a cooling system similar to the manner in which conduits 620 of vest 560 receive cooling fluid from system 622; vests 550, 552, 554, 556, 558, 560, 568 and aprons 562, 564, 566 may have flat tubes integrated therewith similar to the manner in which flat tubes 526 are integrated with wrap 506. These are but a few examples of the possibilities for mixing and matching garment features within the scope of this disclosure. In addition, one or more of the layers of material of each of the garment described herein may comprise any suitable materials such as polyethylene, polystyrene, polycarbonate, or even a polyester material, such as Hydra-tuff 600 denier polyester with a 7 ounce per square yard PVC laminate.

Figure 52:
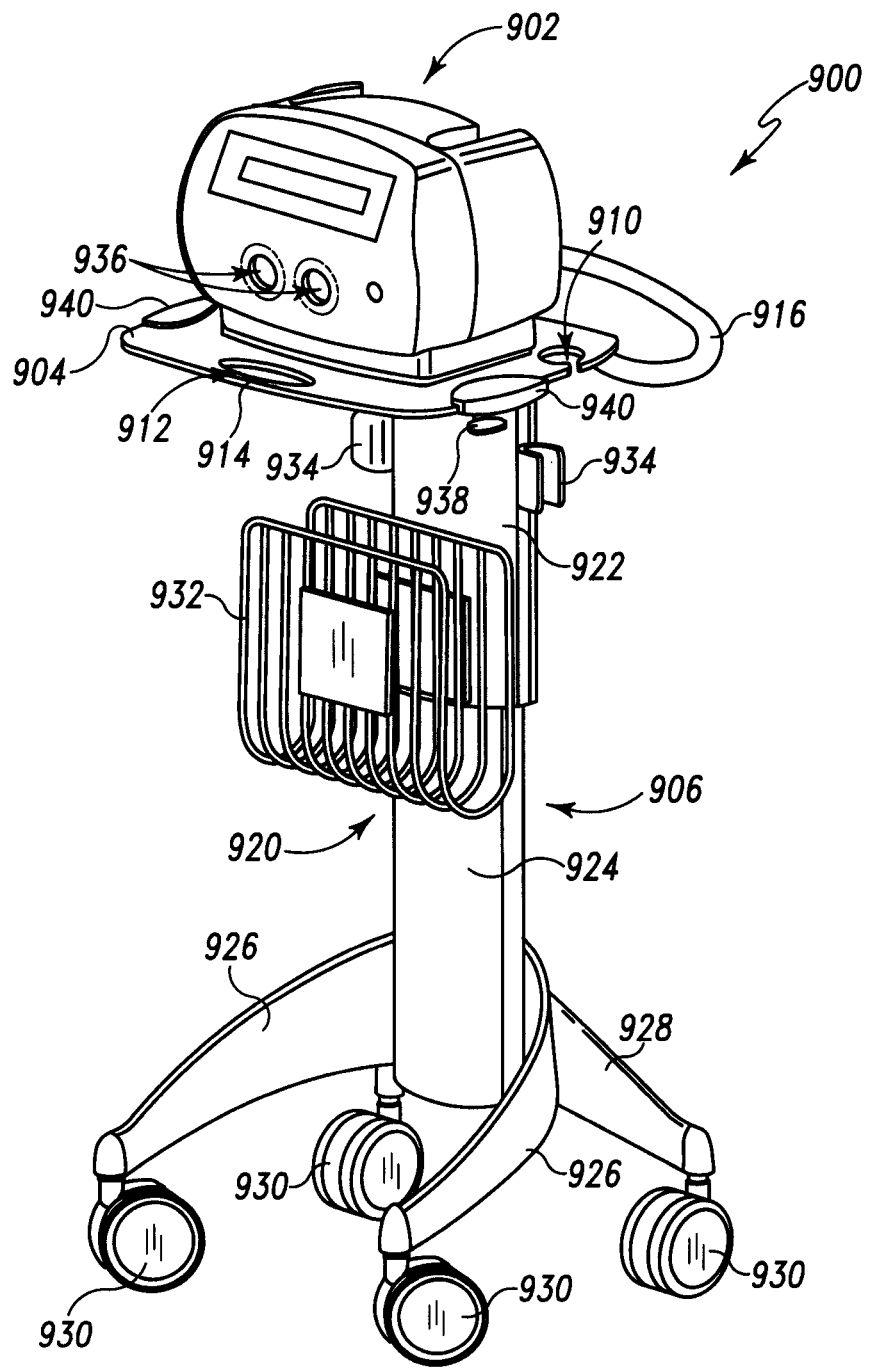
FIG. 52 is a perspective view of another embodiment of a HFCWO therapy system showing an air pulse generator supported on a shelf of a wheeled pedestal, the wheeled pedestal having a vertically oriented telescopic column, a chart holder coupled to a front of an upper segment of the telescopic column, hose clips coupled to the sides of the upper segment of the telescopic column, casters coupled to a set of legs extending from a bottom segment of the telescopic column, a push handle extending rearwardly from the shelf, and a release handle situated just below a side region of the shelf for unlocking an elevation adjustment mechanism situated in an interior region of the telescopic column to permit the upper segment of the column to be raised and lowered relative to the lower segment.
Figure 53:
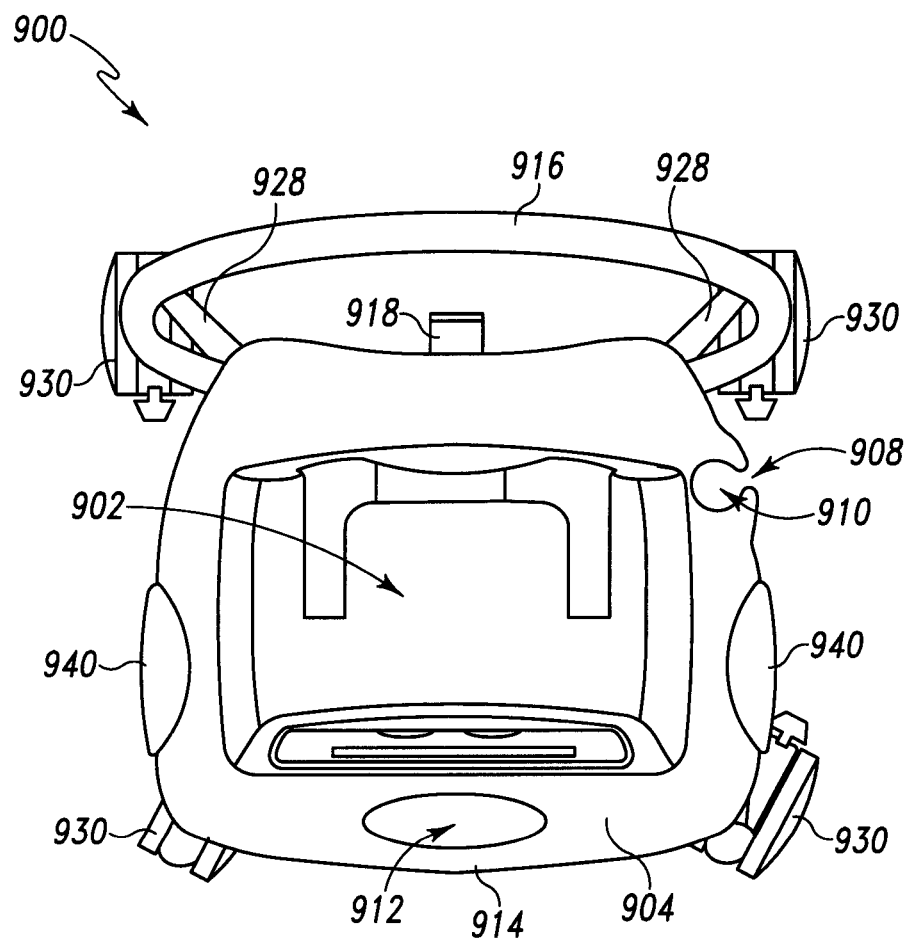
FIG. 53 is a top plan view of the HFCWO therapy system of FIG. 52 showing the shelf having a larger footprint than the air pulse generator such that the shelf has portions extending beyond the front, back, and sides of the air pulse generator, and showing one of the sides regions of the shelf having a notch which opens into a circular aperture which is sized and configured to receive a mouthpiece or other piece of auxiliary equipment which is used with the air pulse generator during HFCWO therapy.

Referring now to FIGS. 52 and 53, a HFCWO therapy system 900 includes an air pulse generator 902 coupled to a shelf 904 of a wheeled pedestal 906. Fasteners, such as screws or bolts (not shown) are used to couple air pulse generator 902 to shelf 904 in some embodiments. Other types of fasteners, such as tabs, fingers, brackets, clips, and the like may be used to couple air pulse generator 902 to shelf 904 in other embodiments, if desired. Shelf 904 has a larger footprint than the air pulse generator 902 of system 900 such that the shelf 904 has portions extending beyond the front, back, and sides of the air pulse generator 902 as shown best in FIG. 53. In the illustrative embodiment, air pulse generator 902 is a Model 104 system which is marketed by Advanced Respiratory, Inc. of St. Paul, Minn. and which is disclosed in U.S. patent application Ser. No. 10/295,782 which published as US Patent Application Publication No. US 2004/0097842 and which is already incorporated by reference herein. In other embodiments, air pulse generator 902 has additional functions such as those discussed above in connection with FIGS. 5-23 and 41-51. Thus, a spirometry mouthpiece and/or nebulizer mouthpiece, such as any of those described herein, may be coupled to air pulse generator 902.

One side of shelf 904 has a notch 908 opening into an aperture 910 that extends between the top and bottom surfaces of shelf 904 as shown in FIG. 53. Notch 908 permits hoses or electrical lines to pass therethrough such that an item associated with the hose or electrical line can be stored within or above aperture 910 on shelf 904. The item may be, for example, a controller (e.g., hand pendant or foot switch) for controlling air pulse generator 902 or a mouthpiece. In the illustrative example, aperture 910 is circular, but apertures 910 of other shapes are within the scope of this disclosure. A hand aperture 912 is provided in a front region of shelf 904 such that a front section 914 of shelf 904 serves has a grip handle. Aperture is oval-shaped in the illustrative example and is long enough to accommodate a portion of a caregiver's hand therein so as to enable the caregiver to grip section 914 when maneuvering system 900 along a floor. In other embodiments, aperture 912 may have shapes other than oval.

A push handle 916 is coupled to the bottom surface of shelf 904 and extends rearwardly therefrom as shown in FIGS. 52 and 53. Push handle 916 is a tubular bar formed as a loop, with the loop extending laterally by about the same among as the lateral distance between the sides of shelf 904. A caregiver may grasp handle 916 to maneuver system 900 along a floor, such as when pushing the system 900 from behind. A hook 918 is also coupled to the bottom of shelf 904 and extends rearwardly therefrom as shown in FIG. 53. Items, such as any of the garments described above, may be hung on hook 918 for storage or while system 900 is being transported from one place to another in a healthcare facility.

Pedestal 906 comprises a vertically oriented telescopic column 920 having an upper segment 922 and a lower segment 924 as shown in FIG. 52. Upper segment 922 may be raised and lowered relative to lower segment 924 to adjust the elevation at which shelf 904 supports air pulse generator 902. Pedestal 906 also has a pair of front legs 926 and a pair of rear legs 928, with each of these legs 926, 928 being coupled to lower segment 924 of column 920. Casters 930 are coupled to distal ends of legs 926, 928 for swiveling movement about substantially vertical axes. Wheels of casters are rotatable about substantially horizontal axes. In the illustrative example, legs 926 are curved such that they initially protrude from lower segment 924 in a laterally extending direction and then curve forwardly such that the distal end regions of legs 926 extend in a forward direction. In addition, the width of each of legs 926 is relative thin and uniform along the curvature thereof, but legs 926 are tapered in vertical height from the proximal ends to the distal ends thereof.

Rear legs 928 are generally straight but angle laterally outwardly and rearwardly from segment 924 to which they are coupled. In addition, rear legs 928 are tapered in vertical height from the proximal ends to the distal ends thereof. Legs 928 are shorter in length than legs 926. This compensates for the fact that, in the illustrative example, column 920 is coupled to shelf 904 closer to the rear edge of shelf 904 than to the front edge. As can be seen in the top plan view of FIG. 52, legs 926, 928 are sized and configured so that the two front casters are situated substantially vertically beneath the front corner regions of shelf 904 and the two rear casters are situated substantially vertically beneath the more sharply curved lateral side portions of handle 916.

A chart holder 932, in the form of a wire basket in the illustrative example, is coupled to a front of upper segment 922 of telescopic column 920 as shown in FIG. 52. A pair of hose clips 934 are also provide on pedestal 906 and are coupled to the sides of upper segment 922 of telescopic column 920 in the illustrative embodiment. Hoses, such as any of those described above, for coupling ports 936 of air pulse generator 902 to an associated garment, may be releasably gripped by hose clips 934 during storage or transport. Thus, chart holder 932 and hose clips 934, as well as any items carried thereby, raise and lower along with segment 922 as segment 922 is raised and lowered relative to segment 924.

Any of the elevation adjustment mechanisms and/or locking mechanisms described above in connection with system 200 of FIGS. 5-11 may be included in pedestal 906 for controlling the telescopic raising and lowering of segment 922 relative to segment 924. A pair of release handles 938 are situated just below respective side regions of shelf 904 and are moveable toward the shelf 904 from a locking position to a releasing position to unlock the elevation adjustment mechanism situated in the interior region of telescopic column 920, thereby to permit the upper segment 922 of the column to be raised and lowered relative to the lower segment 924. In FIG. 52, only one of handles 938 can be seen. Handles 938 are normally biased toward the locking position having the associated elevation adjustment mechanism looked.

In some embodiments, the elevation adjustment mechanism comprises a locking gas spring that, when unlocked, provides an upward force that assists the user in overcoming the weight of segment 922 and all of the equipment carried thereon, during raising of segment 922 relative to segment 924. In the illustrative embodiment, a pair of hand grips 940 are coupled to the side regions of shelf 904 to provide any increased thickness gripping area for a caregiver actuating handles 938 to change the elevation of air pulse generator 902. Hand grips 940 also provide a visual indicia as to the relative location of handles 938 beneath shelf 904 to a caregiver that otherwise may not be able to see handles 938 directly. For example, a caregiver standing behind system 900 and pushing system 900 using handle 916 might not be able to see handles 938. Hand grips 940 include portions that are above, below and alongside shelf 904. Each hand grip 940 has a slot that receives a portion of shelf 904 therein. In some embodiments, hand grips 940 are made of a material, such as rubber, having a greater resiliency than the material from which shelf 904 is made to enhance the comfort of the caregiver grasping hand grips 940 and manipulating release handles 938.

Although certain illustrative embodiments have been described in detail above, variations and modifications exist within the scope and spirit of this disclosure as described and as defined in the following claims.

The invention claimed is:

1. An apparatus for use with a patient, the apparatus comprising:
    a housing,
    a therapy system carried by the housing and operable to deliver a plurality of respiratory therapies to the patient, a first therapy of the plurality of respiratory therapies being a high frequency chest wall oscillation (HFCWO) therapy having a steady state pressure component and an oscillating pressure component, a second therapy of the plurality of respiratory therapies being a therapy other than HFCWO therapy,
    an assessment system carried by the housing and operable to assess the efficacy of at least one of the respiratory therapies based on a measured breath volume, an electronic display on which is shown information regarding the first respiratory therapy, the second respiratory therapy, and the assessment system, the housing being vertically elongated such that its height is greater than both its width and its depth, the therapy system having pneumatic components including at least one of a compressor and a blower carried in a lower portion of the housing and the electronic display being coupled to an upper portion of the housing, and
    a set of wheels coupled to the lower portion of the housing to allow the housing to be transported along a floor, the upper portion of the housing having at least one port through which the HFCWO therapy is delivered to the patient, the at least one port being situated below the display, the pneumatic components being located in a lower part of the lower portion and below the port providing a low center of gravity for the apparatus.

2. The apparatus of claim 1, wherein the second therapy comprises any two or more of the following therapies: a positive expiratory pressure (PEP) therapy, a nebulizer therapy, an intermittent positive pressure breathing (IPPB) therapy, a cough assist therapy, a suction therapy, or a bronchial dilator therapy.

3. The apparatus of claim 1, wherein the assessment system comprises any one or more of the following devices: a spirometer, an electronic stethoscope, a tympanic thermometer, a pulse oximeter, or a respiration rate monitor.

4. The apparatus of claim 1, wherein the electronic display carried by the housing is operable to show numerical data relating to the therapy system.

5. The apparatus of claim 4, wherein the electronic display is further operable to show graphical data relating to the assessment system.

6. The apparatus of claim 1, further comprising a controller carried by the housing and operable to provide control signals to operate at least two of the respiratory therapies.

7. The apparatus of claim 1, further comprising a controller carried by the housing and operable to provide control signals to operate the assessment system and at least one of the respiratory therapies.

8. The apparatus of claim 1, wherein data from the assessment system is used to adjust at least one of the respiratory therapies.

9. The apparatus of claim 1, wherein data from the assessment system is used to adjust the HFCWO therapy.

10. The apparatus of claim 9, wherein data from the assessment system is used to adjust the frequency and intensity of the HFCWO therapy.

11. The apparatus of claim 1, wherein the electronic display comprises a touch screen display and the electronic display is operable to display buttons that are touched to control operation of the first therapy.

12. The apparatus of claim 11, further comprising a controller carried by the housing and operable to control an amplitude of the steady state pressure component, a frequency of the oscillating pressure component and a duration of the HFCWO therapy.

13. The apparatus of claim 12, wherein the electronic display carried by the housing is operable to show operating parameter data relating to the HFCWO therapy.

14. The apparatus of claim 13, wherein the assessment system comprises a spirometer, and the controller is configured to analyze data from the spirometer and show the data on the electronic display.

15. The apparatus of claim 14, wherein data from the spirometer is used to adjust the amplitude of the steady state pressure component and the frequency of the oscillating pressure component.

16. The apparatus of claim 11, further comprising a nebulizer coupled to a pressurized air source carried by the housing.

17. The apparatus of claim 16, wherein the therapy system includes a blower separate from the pressurized air source coupled to the nebulizer.

18. The apparatus of claim 16, wherein the pressurized air source is a compressor.

19. The apparatus of claim 11, wherein the therapy system is configured to be coupled to a vest positioned on the patient.

20. An apparatus comprising: a housing, an air pulse generator including at least one of a compressor and a blower operable to deliver a high frequency chest wall oscillation (HFCWO) therapy to a patient, the air pulse generator including a first pressure source carried by the housing, an assessment system carried by the housing and operable to assess the efficacy of the HFCWO therapy based on a measured breath volume, a second pressure source carried by the housing and configured to be coupled to a nebulizer, and an electronic display on which is shown information regarding the HFCWO therapy, the nebulizer, and the assessment system, the housing being vertically elongated such that its height is greater than both its width and its depth, the air pulse generator being carried in a lower portion of the housing and the electronic display being coupled to an upper portion of the housing, and a set of wheels coupled to the lower portion of the housing to allow the housing to be transported along a floor, the upper portion of the housing having at least one port through which the HFCWO therapy is delivered to the patient, the at least one port being situated below the display, the air pulse generator being located in a lower part of the lower portion and below the port providing a low center of gravity for the apparatus.

* * * * *